United States Patent [19]

Yanagisawa et al.

[11] Patent Number: 5,002,942
[45] Date of Patent: Mar. 26, 1991

[54] 1,5-BENZOTHIAZEPINE DERIVATIVES, THEIR PREPARATION AND THEIR USE IN THE TREATMENT OF CARDIOVASCULAR DISORDERS

[75] Inventors: Hiroaki Yanagisawa; Koichi Fujimoto; Yasuo Shimoji; Takuro Kanazaki; Hiroyuki Koike; Hiroshi Nishino, all of Tokyo, Japan

[73] Assignee: Sankyo Company, Limited, Tokyo, Japan

[21] Appl. No.: 384,261

[22] Filed: Jul. 21, 1989

[30] Foreign Application Priority Data

| Jul. 25, 1988 | [JP] | Japan | 63-185097 |
| Oct. 24, 1988 | [JP] | Japan | 63-267540 |
| Feb. 21, 1989 | [JP] | Japan | 1-41024 |

[51] Int. Cl.$^5$ .................. A61K 31/55; C07D 417/12
[52] U.S. Cl. ...................................... 514/211; 540/491
[58] Field of Search .......................... 540/491; 514/211

[56] References Cited

U.S. PATENT DOCUMENTS

| 4,370,340 | 1/1983 | Ueda et al. | 548/170 |
| 4,438,126 | 3/1984 | Ueda et al. | 548/170 |
| 4,567,175 | 1/1986 | Takeda et al. | 540/491 |
| 4,590,188 | 5/1986 | Takeda et al. | 540/491 |
| 4,594,342 | 6/1986 | Takeda et al. | 540/491 |

FOREIGN PATENT DOCUMENTS

46-43785 12/1971 Japan ................................. 540/491

*Primary Examiner*—Robert T. Bond
*Attorney, Agent, or Firm*—Frishauf, Holtz, Goodman & Woodward

[57] ABSTRACT

Compounds of formula (I):

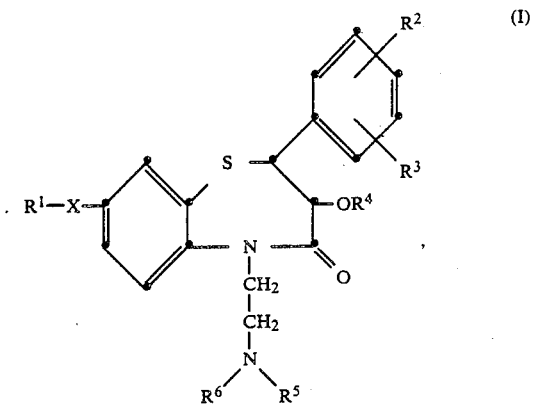

in which: $R^1$ is aryl or aromatic heterocyclic; $R^2$ and $R^3$ are hydrogen, alkyl, alkoxy, halogen, phenyl, phenoxy, $C_1-C_6$ alkylthio, phenylthio, $C_1-C_6$ haloalkyl, cyano or nitro, or together are alkylene optionally containing oxygen; $R^4$ is hydrogen, aliphatic acyl, cycloalkylcarbonyl, cycloalkoxycarbonyl, aromatic acyl, alkoxycarbonyl or benzyloxycarbonyl; $R^5$ and $R^6$ are alkyl; and X is oxygen, sulfur or methylene, have calcium channel blocking activity and can serve for the treatment or prophylaxis of cardiovascular diseases and disorders. They may be prepared by reacting a corresponding compound where $R^4$ is hydrogen and the aminoethyl group is replaced by hydrogen with a compound providing the aminoethyl group and the, if required, acylating the product.

42 Claims, No Drawings

1,5-BENZOTHIAZEPINE DERIVATIVES, THEIR PREPARATION AND THEIR USE IN THE TREATMENT OF CARDIOVASCULAR DISORDERS

BACKGROUND TO THE INVENTION

The present invention relates to a series of new 1.5-benzothiazepine derivatives which are useful in the treatment and prophylaxis of cardiovascular disorders. The invention also provides methods and compositions using these compounds as well as processes for their preparation.

It is now well established that the influx of calcium ions into certain cells in the mammalian body. including the vascular smooth muscle cells and miocardial cells, participates in the activity of such cells and that the administration of calcium channel blockers (also known as calcium antagonists), which inhibit such influx, would suppress myocardial contractile force and rate and cause Vasodilation. The calcium channel blockers are, therefore, useful in the treatment of a variety of diseases and disorders of the heart and vascular system, such as angina pectoris, myocardial infarction, arrhythmia, hypertension, cerebrovascular spasm and other ischemic disease.

A number of compounds having calcium channel blocking activity is known, for example certain dihydropyridine derivatives, such as nifedipine and nicardipine, and other compounds such as verapamil, diltiazem and flunarizine. Of these, nifedipine and nicardipine are widely used, but are structurally unrelated to the compounds of the present invention. Verapamil and flunarizine are also structurally unrelated to the compounds of the present invention. Diltiazem, whose systematic name is (2, 3S)-cis-3-acetoxy-2,3-dihydro-5-(2-dimethylaminoethyl)-2-(4-methoxyphenyl)-1,5-benzothiazepin-4(5H)-one is structurally related to the compounds of the present invention and is widely used for the amelioration of angina pectoris and for the therapy of essential hypertension; it is disclosed in Japanese Patent Publication Kokoku (i.e. published for opposition) No. 43785/1971 which also discloses other related compounds including some having a halo9en substituent on the benzene ring forming part of the benzothiazepine system. Subsequently, derivatives of diltiazem having a substituent for example a chlorine atom, at the 8-position, for example cis-3-acetoxy-8-chloro-2,3-dihydro-5-(2-dimethylaminoethyl)-2-(4-methoxyphenyl)-1,5-benzothiazepin-4(5E,uns/H/ )-one (8-chloro-diltiazem) were U.S. Pat. Specification No. 4 590 188 discloses a number of other derivatives including, for example, cis-3-acetoxy-8-methoxy-2,3-dihydro-5-(2-dimethylaminoethyl)-2-(4-methoxyphenyl)-1,5-benzotbiazepin-4(5E,uns/H/ )-one (8-methoxy-diltiazem), cis-3-acetoxy-8-benzyloxy-2,3-dihydro-5-(2-dimethylaminoethyl)-2-(4-methoxyphenyl)-1,5-benzothiazepin-4(5H)-one (8-benzyloxy-diltiazem), and so on. These derivatives were said to have a stronger action and/or persistency than diltiazem.

We have now discovered a series of new 3-acyloxy-8-substituted-2,3-dihydro-5-(2-dimethylaminoethyl)-2-(optionally substituted phenyl)-5-benzothiazepin-4(5H)-one derivatives which have a potent calcium channel blocking activity and which have a better duration of activity than do the compounds of the prior art. The compounds of the present invention differ from the prior art benzothiazepine compounds in the nature of the substituent at the 8-position of the 1,5-benzothiazepin group.

BRIEF SUMMARY OF INVENTION

The compounds of the present invention are those compounds of formula (I);

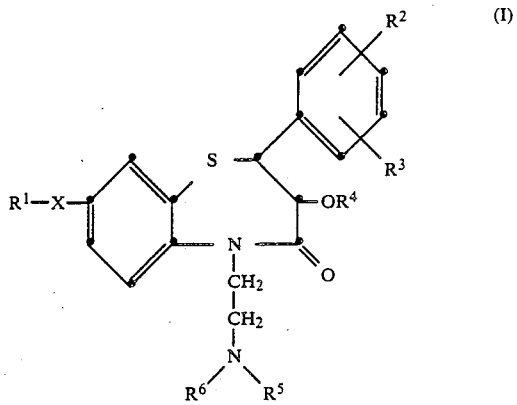

in which:

$R^1$ represents a $C_6$–$C_{10}$ carbocyclic aryl group, a substituted $C_6$–$C_{10}$ carbocyclic aryl group having at least one substituent selected from the group consisting of substituents (a). defined below, an aromatic heterocyclic group having 5 or 6 ring atoms, of which from 1 to 3 are hetero-atoms selected from the group consisting of nitrogen, oxygen and sulfur hetero-atoms, or a substituted aromatic heterocyclic group havinq 5 or 6 ring atoms, of which from 1 to 3 are hetero-atoms selected from the group consisting of nitrogen, oxygen and sulfur hetero-atoms and having at least one substituent selected from the group consisting of substituents (a), defined below, or said heterocyclic group or substituted heterocyclic group fused to a benzene ring;

substituents (a):

$C_1$–$C_6$ alkyl groups, $C_1$–$C_6$ alkoxy groups, halogen atoms, phenyl groups, phenoxy groups, $C_1$–$C_6$ alkylthio groups, phenylthio groups, $C_1$–$C_6$ haloalkyl groups, hydroxy groups, cyano groups, nitro groups and aliphatic chains containing from 1 to 3 carbon atoms and 0, 1 or 2 oxygen atoms;

$R^2$ and $R^3$ are independently selected from the group consisting of hydrogen atoms, $C_1$–$C_6$ alkyl groups, $C_1$–$C_6$ alkoxy groups, halogen atoms, phenyl groups, phenoxy groups, $C_1$–$C_6$ alkylthio groups, phenylthio groups, $C_1$–$C_6$ haloalkyl groups, cyano groups and nitro groups, or $R^2$ and $R^3$ together represent an aliphatic chain containing from 1 to 3 carbon atoms and 0, 1 or 2 oxygen atoms:

$R^4$ represents a hydrogen atom, a $C_1$–$C_6$ aliphatic carboxylic acyl group, a ($C_3$–$C_6$ cycloalkyl)carbonyl group, a ($C_3$–$C_6$ cycloalkoxy)carbonyl group, a $C_7$–$C_{11}$ carbocyclic aromatic carboxylic acyl group, a $C_7$–$C_{11}$ carbocyclic aromatic carboxylic acyl group having at least one substituent selected from the group consisting of $C_1$–$C_6$ alkyl groups, $C_1$–$C_6$ alkoxy groups and halogen atoms, a $C_2$–$C_7$ alkoxycarbonyl group or a benzyloxycarbonyl group;

$R^5$ and $R^6$ are independently selected from the group consisting of $C_1$–$C_6$ alkyl groups; and X represents an oxygen atom, a sulfur atom or a methylene (—$CH_2$—) group;

and pharmaceutically acceptable salts thereof.

The invention also provides a pharmaceutical composition for the treatment or prophylaxis of cardiovascular diseases and disorders which comprises an effective amount of a calcium channel blocker in admixture with a pharmaceutically acceptable carrier or diluent, wherein the calcium channel blocker is at least one compound selected from the group consisting of compounds of formula (I) and pharmaceutically acceptable salts thereof.

The invention still further provides a method for the treatment or prophylaxis of cardiovascular diseases and disorders, which comprises administering to a susceptible animal, especially mammal, including human, an effective amount of a calcium channel blocker, wherein the calcium channel blocker is at least one compound selected from the group consisting of compounds of formula (I) and pharmaceutically acceptable salts thereof.

DETAILED DESCRIPTION OF INVENTION

In the compounds of the present invention, where $R^1$ represents an aryl group, this is a carbocyclic aryl group having from 6 to 10 ring carbon atoms and it may be unsubstituted or it may have at least one substituent selected from the group consisting of substituents (a), defined above and exemplified below. Preferred aryl groups are the phenyl and naphthyl (1-and 2- naphthyl) groups, of which the phenyl group is more preferred.

Where $R^1$ represents an aromatic heterocyclic group this has 5 or 6 ring atoms, of which from 1 to 3 are hetero-atoms selected from the group consisting of nitrogen, oxygen and sulfur hetero-atoms. More preferably the group has from 0 to 3 such nitrogen atoms, 0,1 or 2 such oxygen atoms and 0,1 or 2 such sulfur atoms provided that the total number of hetero-atoms does not exceed 3 and that the resulting group remains aromatic in character. Optionally, the heterocyclic group defined above may be fused to a benzene ring. EXamples of such groups include the thienyl, furyl, benzofuranyl, isobenzofuranyl, pyrrolyl, pyrazolyl, oxazolyl, thiazolyl, isothiazolyl, isoxazolyl, triazolyl, imidazolyl, thiadiazolyl, pyridyl, pyrazinyl, pyrimidyl, pyridazinyl, indolyl, isoindolyl quinolyl isoquinolyl phthalazinyl, quinoxalinyl and cinnolinyl groups, of which the thienyl, furyl, isoxazolyl, oxazolyl, thiazolyl and thiadiazolyl groups are preferred, and the thienyl, furyl, oxazolyl, thiazolyl and thiadiazolyl groups are more preferred.

Especially preferred groups which may be represented by $R^1$ include the phenyl, naphthyl, thiazolyl, furyl, thienyl, oxazolyl, isoxazolyl and thiadiazolyl groups, of which the phenyl, 4-thiazolyl, 2-furyl, 2-thienyl, 4-oxazolyl and 1,3,4-thiadiazol-2-yl groups are more preferred and the phenyl group is the most preferred. Such groups may be unsubstituted or substituted as defined above and exemplified below.

Where $R^2$, $R^3$, $R^5$ or $R^6$, substituent (a) or the substituent on the aromatic acyl group which may be represented by $R^4$ represents an alkyl group, this has from 1 to 6 carbon atoms, and may he a straight or branched chain group for eXample the methyl, ethyl, propyl, isopropyl, butyl, isobutyl, sec-butyl, t-butyl, pentyl, isopentyl, neopentyl, t-pentyl, hexyl, 1-methylpentyl, 2-methylpentyl, 3-methylpentyl and isohexyl groups, of which those groups having from 1 to 4 carbon atoms, for example the methyl, ethyl, propyl, isopropyl, butyl, sec-butyl and isobutyl groups are preferred, and the methyl and ethyl groups are most preferred.

Where $R^2$, $R^3$, substituent (a) or the substituent on the aromatic acyl group which may be represented by $R^4$ represents an alkoxy group, this has from 1 to 6 carbon atoms, and may be a straight or branched chain group, for example the methoxy, ethoxy, propoxy, isopropoxy, butoxy, isobutoxy, sec-butoxy, t-butoxy, pentyloxy, isopentyloxy, neopentyloxy, t-pentyloxy, hexyloxy, 1-methylpentyloxy, 2-methylpentyloxy, 3-methylpentyloxy and isohexyloxy groups, of which those groups having from 1 to 4 carbon atoms, for example the methoxy, ethoxy, propoxy, isopropoxy, butoXy, sec-butoxy and isobutoxy groups are preferred, and the methoxy and ethoxy groups are most preferred.

Where $R^2$, $R^3$, substituent (a) or the substituent on the aromatic acyl group which may be represented by $R^4$ represents a halogen atom, this may be for example, a tluorine, chlorine, bromine or iodine atom, of which the fluorine, chlorine and bromine atoms are preferred and the fluorine and chlorine atoms are more preferred.

Where $R^2$, $R^3$ or substituent (a) represents an alkylthio group, this has from 1 to 6 carbon atoms, and may be a straight or branched chain group, for example the methylthio ethylthio, propylthio isopropylthio, butylthio, isobutylthio, sec-butylthio, t-butylthio, pentylthio, isopentylthio, neopentylthio, t-pentylthio, hexylthio, 1-methylpentylthio, 2-methylpentylthio, 3-methylpentylthio and isohexylthio groups, of which those groups having from 1 to 4 carbon atoms, for example the methylthio, ethylthio, propylthio, isopropylthio, butylthio, .sec-butylthio and isobutylthio groups are preferred and the methylthio and ethylthio groups are most preferred.

Where $R^2$, $R^3$ or substituent (a) represents a $C_1$–$C_6$, preferably $C_1$–$C_4$, haloalkyl group, examples include the trifluoromethyl, 2,2,2-trichloroethyl, 2-haloethyl (e.g. 2-chloroethyl, 2-fluoroethyl, 2-bromoethyl or 2-iodoethyl), 2,2-dibromoethyl, 2,2,2-tribromoethyl, 5-chloropentyl, 5-bromopentyl, 5-fluoropentyl, 6-chlorohexyl, 6-bromohexyl and 6-fluorohexyl groups.

Where substituent (a) or $R^2$ and $R^3$ together represent an aliphatic chain containing from 1 to 3 carbon atoms and 0,1 or 2 oxygen atoms, this may be a $C_1$–$C_3$ alkylene group or an analog thereof having a carbon-carbon double or triple bond, preferably a double bond, or such a group having 1 or 2 oxygen atoms in and/or at either or both ends of the carbon chain. Examples include the methylene, ethylene, trimethylene, oxyethylene (—OCH$_2$CH$_2$—), methyleneoxymethylene (—CH$_2$OCH$_2$—), oxypropylene (—O—CH$_2$CH$_2$CH$_2$—), methyleneoxyethylene (—CH$_2$—O—CH$_2$—CH$_2$—), methylenedioxy (—O—CH$_2$—O—), ethylenedioxy (—OCH$_2$—CH$_2$—O—) and oxyvinylene (—OCH=CH—), groups, of which the methylenedioxy group is preferred.

Where $R^4$ represents a $C_1$–$C_6$ aliphatic carboxylic acyl group, this may be a straight or branched chain group, for example the formyl, acetyl, propionyl, butyryl, isobutyryl, valeryl, isovaleryl, pivaloyl or hexanoyl group, of which the acetyl, propionyl, butyryl and isobutyryl groups are preferred, the acetyl and propionyl groups being most preferred.

Where $R^4$ represents a ($C_3$–$C_6$ cycloalkyl)-carbonyl group, this may be a cyclopropanecarbonyl, cyclobutanecarbonyl, cyclopentanecarbonyl or cyclohexanecarbonyl group, of which the cyclopropanecarbonyl group is preferred.

Where $R^4$ represents a ($C_3$–$C_6$ cycloalkoxy)-carbonyl group, this may be a cyclopropaneoxycarbonyl, cyclobutaneoxycarbonyl, cyclopentaneoxycarbonyl or cyclohexaneoxycarbonyl group, of which the cyclopropaneoxycarbonyl group is preferred.

Where $R^4$ represents a $C_7$–$C_{11}$ carbocyclic aromatic carboxylic acyl group, this is an arylcarbonyl group in which the aryl part has from 6 to 10 carbon atoms, and is preferably a phenyl or naphthyl (1- or 2-naphthyl) group, which may be unsubstituted or may have at least one substituent selected from the group consisting of $C_1$–$C_6$ alkyl groups, $C_1$–$C_6$ alkoxy groups and halogen atoms. Specific examples of such groups include the benzoyl, o-, m- or p- toluoyl, 1-naphthoyl 2-naphthoyl, o-, m- or p- anisoyl, veratroyl, o-, m- or p- isopropylbenzoyl and 3,4,5 -trimethoxybenzoyl groups, of which the benzoyl, toluoyl, 1-naphthoyl and 2-naphthoyl groups are preferred and the benzoyl and toluoyl groups are most preferred.

Where $R^4$ represents a $C_2$–$C_7$ alkoxycarbonyl group the alkoxy part has from 1 to 6 carbon atoms and may be any of the $C_1$–$C_6$ alkoxy groups exemplified above. Specific examples of such alkoxycarbonyl groups include the methoxycarbonyl, ethoxyoarbonyl, propoxycarbonyl, isopropoXycarbonyl, butoxycarbonyl isobutoxycarbonyl, pentyloxycarbonyl and hexyloxycarbonyl groups, of which the methoxycarbonyl, ethoxycarbonyl, propoxycarbonyl and isopropoxycarbonyl groups are more preferred and the methoxycarbonyl and ethoxycarbonyl groups are most preferred.

Especially preferred groups Which may be represented by $R^1$ include the phenyl, p-chlorophenyl, p-methoxyphenyl, p-fluorophenyl, p-methylphenyl, m-fluorophenyl, o-fluorophenyl, m-methylphenyl, m-methoXyphenyl, 3,4- methylenedioxyphenyl, 1-naphthyl, 2-naphthyl, 4-thiazolyl, 2-furyl, 2-thienyl, 5-methyl-2-thienyl, 5-chloro-2-thienyl, 4-oxazolyl, 4-isoxazolyl and 1,3,4-thiadiazol-2-yl groups, the phenyl, p-fluorophenyl and 2-thienyl groups being more preferred and the phenyl and p-fluorophenyl groups being most preferred.

Especially preferred groups and atoms which may be represented by $R^2$ include the hydrogen, fluorine and chlorine atoms, and the methyl and methoxy groups.

Especially preferred groups and atoms which may be represented by $R^3$ include the hydrogen, fluorine and chlorine atoms, and the methoxy and ethoxy groups. Especially preferred groups which may be represented by $R^2$ and $R^3$ together include the methylenedioxy group.

Especially preferred groups and atoms which may be represented by $R^4$ include the hydrogen atom, and the acetyl, propionyl, butyryl, isobutyryl, cyclopropylcarbonyl, cyclobutylcarbonyl, cyclopentylcarbonyl, cyclohexylcarbonyl, cyclopropoxycarbonyl, benzoyl, toluoyl methoxycarbonyl ethoxycarbonyl propoxycarbonyl, isopropoxycarbonyl, valeryl, cyclopentyloxycarbonyl, cyclohexyloxycarbonyl and formyl groups, the hydrogen atom and the acetyl propionyl, cyclopropylcarbonycarbonyl, cyclopropoxycarbonyl, benzoyl, toluoyl, methoxycarbonyl and ethoxycarbonyl groups beinq more preferred.

Especially preferred groups which may be represented by $R^5$ include the methyl and ethyl groups.

Especially preferred groups which may be represented by $R^6$ include the methyl, ethyl, propyl and butyl group.

X preferably represents an oxygen atom or a methylene group, more preferably the oxygen atom.

A preferred class of compounds of the present invention are those compounds of formula (I) in which:

$R^1$ represents a phenyl group, a substituted phenyl group having at least one substituent selected from the group consisting of substituents ($a^1$), defined below, an aromatic heterocyclic group having from 5 to 6 ring atoms of which from 1 to 3 are hetero-atoms selected from the group consisting of nitrogen, oxygen and sulfur hetero-atoms or a substituted aromatic heterocyclic group having from 5 to 6 ring atoms of which from 1 to 3 are hetero-atoms selected from the group consisting of nitrogen, oxygen and sulfur hetero-atoms and having at least one substituent selected from the group consisting of substituents ($a^2$);

substituents ($a^1$):
$C_1$–$C_4$ alkyl groups, $C_1$–$C_4$ alkoxy groups and halogen atoms;

substituents ($a^2$):
$C_1$–$C_4$ alkyl groups and halogen atoms;
and pharmaceutically acceptable salts thereof.

Also preferred are those compounds of formula (I) in which:

$R^2$ and $R^3$ are independently selected from the group consisting of hydrogen atoms, $C_1$–$C_4$ alkyl groups, $C_1$–$C_4$ alkoxy groups and halogen atoms, or $R^2$ and $R^3$ together represent an aliphatic chain containing from 1 to 3 carbon atoms and 1 or 2 oxygen atoms;
and pharmaceutically acceptable salts thereof.

Also preferred are those compounds of formula (I) in which:

$R^4$ represents a hydrogen atom, a $C_2$–$C_6$ aliphatic carboxylic acyl group, a ($C_3$–$C_6$ cycloalkyl)carbonyl group, a ($C_3$–$C_6$ cycloalkoxy)carbonyl group, a $C_7$–$C_{11}$ arylcarbonyl group, a substituted $C_7$–$C_{11}$ arylcarbonyl group having at least one $C_1$–$C_4$ alkyl substituent, or a $C_2$–$C_5$ alkoxycarbonyl group:
and pharmaceutically acceptable salts thereof.

Also preferred are those compounds of formula (I) in which:

$R^5$ and $R^6$ are independently selected from the group consisting of $C_1$–$C_4$ alkyl groups;
and pharmaceutically acceptable salts thereof.

Especially preferred are those compounds of formula (I) in which $R^1$, $R^2$, $R^3$, $R^4$, $R^5$ and $R^6$ are all as defined above as preferred, and X represents an oxygen atom, a sulfur atom or a methylene group; and pharmaceutically acceptable salts thereof.

A more preferred class of compounds of the present invention are those compounds of formula (I) in which:

$R^1$ represents:
 a phenyl group,
 a substituted phenyl group having at least one substituent selected from the group consisting of substituents ($a^1$), defined above, or
 an aromatic heterocyclic group selected from the group consisting of thienyl, furyl, isoxazolyl, oxazolyl, thiazolyl and thiadiazolyl groups, said heterocyclic group being unsubstituted or having at least one $C_1$–$C_4$ alkyl substituent;

$R^2$ and $R^3$ are independently selected from the group consisting of hydrogen atoms, $C_1$–$C_4$ alkyl groups, $C_1$–$C_4$ alkoxy groups and halogen atoms, or $R^2$ and $R^3$ together represent an aliphatic chain containing from 1 to 3 carbon atoms and 1 or 2 oxygen atoms;

$R^4$ represents a hydrogen atom, a $C_2$–$C_6$ aliphatic carboxylic acyl group a ($C_3$–$C_6$ cycloalkyl)carbonyl group, a ($C_3$-$C_6$ cycloalkoxy)carbonyl group, a benzoyl group, a substituted benzoyl group having at least one $C_1$-$C_4$ alkyl substituent, or a $C_2$-$C_5$ alkoxycarbonyl group;

$R^5$ and $R^6$ are independently selected from the group consisting of $C_1$-$C_4$ alkyl groups; and X represents an oxygen atom, a sulfur atom or a methylene group;

and pharmaceutically acceptable salts thereof.

A most preferred class of compounds of the present invention are those compounds of formula (I) in which:

$R^1$ represents:
  a phenyl group,
  a substituted phenyl group having at least one substituent selected from the group consisting of substituents ($a^3$), defined below, or
  an aromatic heterocyclic group selected from the group consisting of thienyl, furyl, oxazolyl, thiazolyl and thiadiazolyl groups, said heterocyclic group being unsubstituted or having at least one methyl substituent;

substituents ($a^3$):
  methyl groups, methoxy groups, fluoro atoms and chloro atoms;

$R^2$ and $R^3$ are independently selected from the group consisting of hydrogen atoms, methyl groups, methoxy groups, ethoxy groups, fluorine atoms and chlorine atoms, or $R^2$ and $R^3$ together represent an group of formula —O—$CH_2$—O—;

$R^4$ represents a hydrogen atom, an acetyl group a propionyl group, a cyclopropanecarbonyl group, a cyclopropoxycarbonyl group, a benzoyl group, a toluoyl group, a methoxycarbonyl group or an ethoxycarbonyl group;

$R^5$ and $R^6$ are independently selected from the group consisting of methyl and ethyl groups; and X represents an oXygen atom or a methylene group;

and Pharmaceutically acceptable salts thereof.

The compounds of formula (I) have two asymmetric carbon atoms at the 2-position and at the 3-position on the benzothiazepine ring accordingly, two kinds of stereoisomers (cis and trans isomers) and 4 kinds of optical isomers [(2S, 3S), (2R, 3R), (2S, 3R) and (2R, 3S) isomers] can exist. The present invention embraces all of these isomers, whether isolated or present as mixtures. Of the isomers, the cis isomers are preferred and the (2S, 3S) isomers are most preferred.

Examples of specific compounds of the invention are given in the following formulae (I-1) to (I-3), in which the substituents are as defined in the corresponding one of Tables 1 to 3, respectively [i.e Table 1 relates to formula (I-1), Table 2 relates to formula (I-2) and so on]. In the Tables, the following abbreviations are used:

| Ac | acetyl |
| Boz | benzoyl |
| Bu | butyl |
| cBu | cyclobutyl |
| Byr | butyryl |
| iByr | isobutyryl |
| Et | ethyl |
| Etc | ethoxycarbonyl |
| Fur | furyl |
| cHx | cyclohexyl |
| Isox | isoxazolyl |
| Me | methyl |
| Mec | methoxycarbonyl |
| Np | naphthyl |
| Oxa | oxazolyl |
| cPn | cyclopentyl |

-continued

| Pr | propyl |
| cPr | cyclopropyl |
| Prc | propoxycarbonyl |
| iPrc | isopropoxycarbonyl |
| Prn | propionyl |
| Thaz | 1,3,4-thiadiazolyl |
| Thi | thienyl |
| Thiz | thiazolyl |
| Tly | toluoyl |
| Va | valeryl |

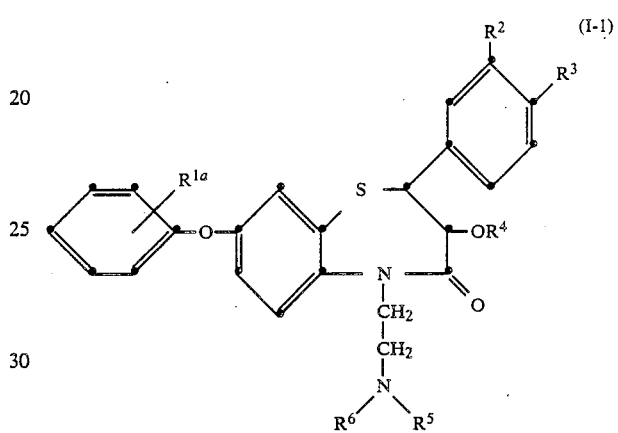

(I-1)

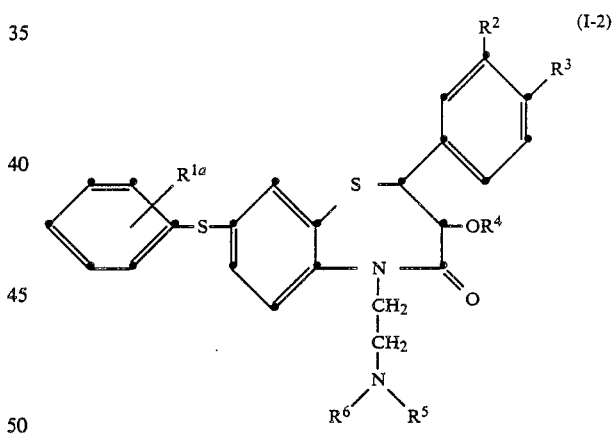

(I-2)

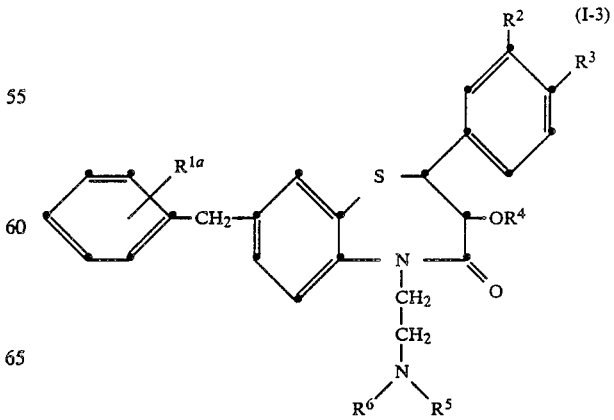

(I-3)

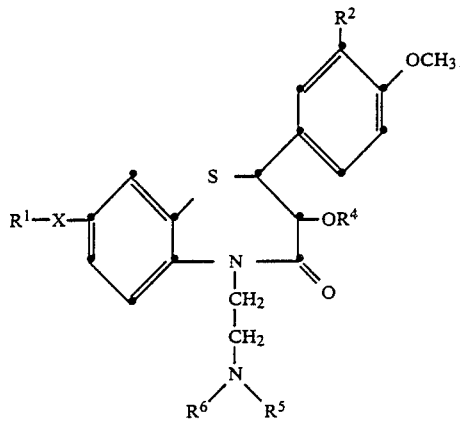

(I-4)

TABLE 1

| Cpd No. | $R^{1a}$ | $R^2$ | $R^3$ | $R^4$ | $R^5$ | $R^6$ |
|---|---|---|---|---|---|---|
| 1-1 | H | H | OMe | H | Me | Me |
| 1-2 | H | H | OMe | Ac | Me | Me |
| 1-3 | H | H | OMe | Prn | Me | Me |
| 1-4 | H | H | OMe | Byr | Me | Me |
| 1-5 | H | H | OMe | iByr | Me | Me |
| 1-6 | H | H | OMe | cPrCO | Me | Me |
| 1-7 | H | H | OMe | cBuCO | Me | Me |
| 1-8 | H | H | OMe | cPnCO | Me | Me |
| 1-9 | H | H | OMe | cHxCO | Me | Me |
| 1-10 | H | H | OMe | Mec | Me | Me |
| 1-11 | H | H | OMe | Etc | Me | Me |
| 1-12 | H | H | OMe | Prc | Me | Me |
| 1-13 | H | H | OMe | iPrc | Me | Me |
| 1-14 | H | F | OMe | H | Me | Me |
| 1-15 | H | F | OMe | Ac | Me | Me |
| 1-16 | H | Cl | OMe | H | Me | Me |
| 1-17 | H | Cl | OMe | Ac | Me | Me |
| 1-18 | H | Me | OMe | Ac | Me | Me |
| 1-19 | H | | 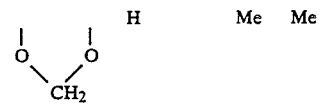 | H | Me | Me |
| 1-20 | H | | 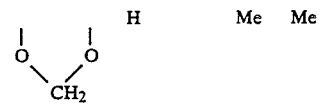 | Ac | Me | Me |
| 1-21 | H | | 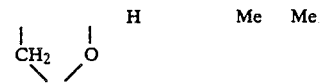 | H | Me | Me |
| 1-22 | H | |  | Ac | Me | Me |
| 1-23 | H | |  | Ac | Me | Me |
| 1-24 | H | | 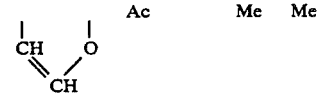 | Ac | Me | Me |
| 1-25 | H | H | OMe | Ac | Me | Et |
| 1-26 | H | H | OMe | Ac | Me | Pr |
| 1-27 | H | H | OMe | Ac | Et | Et |
| 1-28 | p-Cl | H | OMe | Ac | Me | Me |

TABLE 1-continued

| Cpd No. | $R^{1a}$ | $R^2$ | $R^3$ | $R^4$ | $R^5$ | $R^6$ |
|---|---|---|---|---|---|---|
| 1-29 | p-OMe | H | OMe | Ac | Me | Me |
| 1-30 | p-F | H | OMe | Ac | Me | Me |
| 1-31 | p-Me | H | OMe | Ac | Me | Me |
| 1-32 | H | Me | OMe | Ac | Me | Me |
| 1-33 | H | OMe | OMe | Ac | Me | Me |
| 1-34 | H | H | OMe | Va | Me | Me |
| 1-35 | H | H | OMe | Ac | Me | Bu |
| 1-36 | p-F | H | OMe | H | Me | Me |
| 1-37 | p-Cl | H | OMe | H | Me | Me |
| 1-38 | p-OMe | H | OMe | H | Me | Me |
| 1-39 | p-Me | H | OMe | H | Me | Me |
| 1-40 | p-F | F | OMe | H | Me | Me |
| 1-41 | p-F | F | OMe | Ac | Me | Me |
| 1-42 | H | H | OMe | cPnOCO— | Me | Me |
| 1-43 | H | H | OMe | cHxOCO— | Me | Me |
| 1-44 | H | H | OMe | CHO | Me | Me |
| 1-45 | H | F | OMe | CHO | Me | Me |
| 1-46 | H | OMe | H | H | Me | Me |
| 1-47 | H | OMe | H | Ac | Me | Me |
| 1-48 | H | OMe | F | H | Me | Me |
| 1-49 | H | OMe | F | Ac | Me | Me |
| 1-50 | H | OMe | Cl | Ac | Me | Me |
| 1-51 | H | H | OEt | H | Me | Me |
| 1-52 | H | H | OEt | Ac | Me | Me |
| 1-53 | H | F | OEt | Ac | Me | Me |
| 1-54 | m-F | H | OMe | H | Me | Me |
| 1-55 | m-F | H | OMe | Ac | Me | Me |
| 1-56 | m-F | F | OMe | Ac | Me | Me |
| 1-57 | o-F | H | OMe | H | Me | Me |
| 1-58 | o-F | H | OMe | Ac | Me | Me |
| 1-59 | o-F | F | OMe | Ac | Me | Me |
| 1-60 | m-Me | H | OMe | H | Me | Me |
| 1-61 | m-Me | H | OMe | Ac | Me | Me |
| 1-62 | m-MeO | H | OMe | Ac | Me | Me |
| 1-63 | H | H | OMe | H | Et | Et |
| 1-64 | 3,4-(—OCH$_2$O—) | H | OMe | H | Me | Me |
| 1-65 | 3,4-(—OCH$_2$O—) | H | OMe | Ac | Me | Me |
| 1-66 | H | H | OMe | Boz | Me | Me |
| 1-67 | F | H | OMe | Boz | Me | Me |
| 1-68 | H | H | OMe | Tly | Me | Me |
| 1-69 | F | H | OMe | Tly | Me | Me |

TABLE 2

| Cpd No. | $R^{1a}$ | $R^2$ | $R^3$ | $R^4$ | $R^5$ | $R^6$ |
|---|---|---|---|---|---|---|
| 2-1 | H | H | OMe | H | Me | Me |
| 2-2 | H | H | OMe | Ac | Me | Me |
| 2-3 | H | F | OMe | Ac | Me | Me |

TABLE 3

| Cpd No. | $R^{1a}$ | $R^2$ | $R^3$ | $R^4$ | $R^5$ | $R^6$ |
|---|---|---|---|---|---|---|
| 3-1 | H | H | OMe | H | Me | Me |
| 3-2 | H | H | OMe | Ac | Me | Me |
| 3-3 | H | H | OMe | cPrCO | Me | Me |
| 3-4 | H | H | OMe | Mec | Me | Me |
| 3-5 | H | F | OMe | H | Me | Me |
| 3-6 | H | F | OMe | Ac | Me | Me |
| 3-7 | H | Cl | OMe | H | Me | Me |
| 3-8 | H | Cl | OMe | Ac | Me | Me |
| 3-9 | H | H | OMe | H | Et | Et |
| 3-10 | H | H | OMe | Ac | Et | Et |
| 3-11 | p-Me | H | OMe | Ac | Me | Me |
| 3-12 | m-Me | H | OMe | Ac | Me | Me |
| 3-13 | p-OMe | H | OMe | Ac | Me | Me |
| 3-14 | p-Cl | H | OMe | Ac | Me | Me |
| 3-15 | p-F | H | OMe | Ac | Me | Me |
| 3-16 | H | H | OMe | Etc | Me | Me |
| 3-17 | H | H | OMe | CHO | Me | Me |
| 3-18 | H | OMe | H | Ac | Me | Me |
| 3-19 | H | H | OEt | Ac | Me | Me |
| 3-20 | m-F | H | OEt | Ac | Me | Me |
| 3-21 | o-F | H | OEt | Ac | Me | Me |
| 3-22 | m-F | H | OMe | Ac | Me | Me |

TABLE 3-continued

| Cpd No. | R$^{1a}$ | R$^2$ | R$^3$ | R$^4$ | R$^5$ | R$^6$ |
|---|---|---|---|---|---|---|
| 3-23 | o-F | H | | OMe | Ac | Me | Me |
| 3-24 | p-F | H | | OMe | H | Me | Me |

TABLE 4

| Cpd No. | R$^1$ | R$^2$ | R$^4$ | R$^5$ | R$^6$ | X |
|---|---|---|---|---|---|---|
| 4-1 | 2-Thi | H | H | Me | Me | —CH$_2$— |
| 4-2 | 2-Thi | H | Ac | Me | Me | —CH$_2$— |
| 4-3 | 2-Fur | H | H | Me | Me | —CH$_2$— |
| 4-4 | 2-Fur | H | Ac | Me | Me | —CH$_2$— |
| 4-5 | 4-Thiz | H | H | Me | Me | —CH$_2$— |
| 4-6 | 4-Thiz | H | Ac | Me | Me | —CH$_2$— |
| 4-7 | 4-Oxa | H | H | Me | Me | —CH$_2$— |
| 4-8 | 4-Oxa | H | Ac | Me | Me | —CH$_2$— |
| 4-9 | 4-Isox | H | H | Me | Me | —CH$_2$— |
| 4-10 | 4-Isox | H | Ac | Me | Me | —CH$_2$— |
| 4-11 | 2-Thaz | H | H | Me | Me | —CH$_2$— |
| 4-12 | 2-Thaz | H | Ac | Me | Me | —CH$_2$— |
| 4-13 | 1-Np | H | H | Me | Me | —CH$_2$— |
| 4-14 | 1-Np | F | H | Me | Me | —CH$_2$— |
| 4-15 | 1-Np | H | Ac | Me | Me | —CH$_2$— |
| 4-16 | 1-Np | H | H | Me | Me | —O— |
| 4-17 | 1-Np | H | Ac | Me | Me | —O— |
| 4-18 | 2-Np | H | Ac | Me | Me | —O— |
| 4-19 | 2-Thi | F | Ac | Me | Me | —CH$_2$— |
| 4-20 | 5-Me-2-Thi | H | Ac | Me | Me | —CH$_2$— |
| 4-21 | 5-Cl-2-Thi | H | Ac | Me | Me | —CH$_2$— |
| 4-22 | 5-Me-2-Thi | H | H | Me | Me | —CH$_2$— |

Of the compounds listed above, the following are preferred, that is to say Compounds Nos. 1-1, 1-2, 1-3, 1-4, 1-5, 1-6, 1-8, 1-10, 1-11, 1-14, 1-15, 1-16, 1-17, 1-19, 1-20, 1-21, 1-22, 1-23, 1-24, 1-25, 1-27, 1-28, 1-29, 1-30, 1-31, 1-36, 1-40, 1-41, 1-42, 1-43, 1-44, 1-46, 1-47, 1-54, 1-55, 1-57, 1-58, 3-1, 3-2, 3-3, 3-4, 3-5, 3-6, 3-7, 3-8, 3-9, 3-10, 3-15, 3-16, 3-17, 3-24, 4-1, 4-2, 4-3, 4-4, 4-5, 4-6, 4-7, 4-8, 4-11, 4-12, 4-13, 4-15, 4-16, 4-17, 4-18 and 4-19, and the following are more preferred, that is to say Compounds Nos. 1-1, 1-2, 1-14, 1-15, 1-17, 1-19, 1-20, 1-22, 1-23, 1-27, 1-30, 1-36, 1-40, 1-41, 3-1, 3-2, 3-5, 3-6, 3-15, 3-24, 4-1, 4-2, 4-3, 4-4, 4-5, 4-6 and 4-19, The following are the most preferred compounds:

1-1. 5-(2-dimethylaminoethyl)-2,3-dihydro-3-hydroxy-2-(4-methoxyphenyl)-8-phenoxy-1,5-benzothiazepin-4(5H)-one, especially the (2S, 3S)-5-(2-dimethylaminoethyl)-2,3-dihydro-3-hydroxy-2-(4-methoxyphenyl)-8-phenoxy-1,5-benzothiazepin-4(5H)-one isomer;

1-2. 3-acetoxy-5-(2-dimethylaminoethyl)-2,3-dihydro-2-(4-methoxyphenyl)-8-phenoxy-1,5-benzothiazepin-4(5H)-one, especially the (2S, 3S)-3-acetoxy-5-(2-dimethylaminoethyl)-2,3-dihydro-2-(4-methoxyphenyl)-8-phenoxy-1,5-benzothiazepin-4(5H)-one isomer; 1-14. 5-(2-dimethylaminoethyl)-2-(3-fluoro-4-methoxyphenyl))-2,3-dihydro-3-hydroxy-8-phenoxy-1,5-benzothiazepin-4(5H)-one, especially the (2S, 3S)-5-(2-dimethylaminoethyl)-2-(3-fluoro-4-methoxyphenyl)-2,3-dihydro-3-hydroxy-8-phenoxy-1,5-benzothiazepin-4(5H)-one isomer;

1-15. 3-acetoxy-5-(2-dimethylaminoethyl)-2-(3-fluoro-4-methyoxyphenyl)-2,3-dihydro-8-phenoxy-1,5-benzothiazepin-4(5H)-one, especially the (2S, 3S)-3-acetoxy-5-(2-dimethylaminoethyl)-2-(3-fluoro-4-methoxyphenyl) 2,3-dihydro-8-phenoxy-1,5-benzothiazepin-4(5H)-one isomer;

1-19. 5-(2-dimethylaminoethyl)-2,3-dihydro-3-hydroxy-2-(3,4-methylenedioxyphenyl)-8-phenoxy-1,5-benzothiazepin-4(5H)-one, especially the (2S, 3S)-5-(2-dimethylaminoethyl)-2,3-dihydro-3-hydroxy-2-(3,4-methylenedioxyphenyl)-8-phenoxy-1,5-benzothiazepin-4(5H)-one isomer;

1-20. 3-acetoxy-5-(2-dimethylaminoethyl)-2.3-dihydro-2-(3,4-methylenedioxyphenyl)-8-phenoxy-1,5-benzothiazepin-(5H)-one, especially the (2S, 3S)-3-acetoxy-5-(2-dimethylaminoethyl)-2,3-dihydro-2-(3,4-methylenedioxy-phenyl)-8-phenoxy-1,5-benzothiazepin-(5H)-one isomer; 4-1. 4-2, 4-3, 4-4, 4-5, 4-6, 4-7, 4-8, 4-11, 4-1, 4-2, 4-3, 4-4, 4-5, 4-6, 4-7, 4-8, 4-11, phenoxy)-2,3-dihydro-2-(4-methoxyphenyl)-1,5-benphenoxy)-2,3-dihydro-2-(4-methoxyphenyl)-1,5-benzothiazepin-4(5H)-one, especially the (2S, 3S)-3-acetoxy-5-(2-dimethylaminoethyl)-8-(4-fluorophenoxy)-2,3-dihydro-2-(4-methoxyphenyl)-1,5-benzothiazepin-4(5H)-one isomer;

1-36. 5-(2-dimethylaminoethyl)-8-(4-fluorophenoxy)-2,3-dihydro-3-hydroxy-2-(4-methoxyphenyl)-1,5-benzothiazepin-4(5H)-one, especially the (2S, 3S)-5-(2-dimethylaminoethyl)-8-(4-fluorophenoxy)-2,3-dihydro-3-hydroxy-2-(4-methoxyphenyl)-1,5-benzothiazepin-4(5H)-one isomer;

1-40. 5-(2-dimethylaminoethyl)-2-(3-fluoro-4-methoxyphenyl)- 8-(4-fluorophenoxy)-2,3-dihydro-3-hydroxy-1,5- benzothiazepin-4(5H)-one, especially the (2S, 3S)-5-(2- dimethylaminoethyl)-2-(3-fluoro-4-methoxyphenyl)-8-(4- fluorophenoxy)-2,3-dihydro-3-hydroxy-1,5-benzothiazepin-4(5H)-one isomer;

1-41. 3-acetoxy-5-(2-dimethylaminoethyl)-2-(3-fluoro-4-methoxyphenyl)-8-(4-fluorophenoxy)-2,3-dihydro-1,5-benzothlazepin-4(5H)-one, especially the (2S, 3S)-3- acetoxy-5-(2-dimethylaminoethyl)-2- (3-fluoro-4-methoxyphenyl)-8-(4-fluorophenoxy)-2,3-dihydro-1,5-benzothiazepin-4(5H)-one isomer;

3-1. 8-benzyl-5-(2-dimethylaminoethyl)-2,3-dihydro-3-hydroxy-2-(4-methoxyphenyl)-1,5-benzothiazepin-4(5H)-one, especiallY the (2S, 3S)-8-benzyl-5-(2-dimethylaminoethyl)-2,3-dihydro-3-hydroxy-2-(4-methoxyphenyl)-1,5-benzothiazepin-4(5H)-one isomer;

3-2. 3-acetoxy-8-benzyl-5-(2-dimethylaminoethyl)-2,3-dihydro-2-(4-methoxyphenyl)-1,5-benzothiazepin-4(5H)-one, especially the (2S, 3S)-3-acetoxy-8-benzyl-5-(2- dimethylaminoethyl)-2,3-dihydro-2-(4-methoxyphenyl)-1,5- benzothiazepin-4(5H)-one isomer;

3-5. 8-benzyl-5-(2-dimethylaminoethyl)-2-(3-fluoro- 4-methoxyphenyl)-2,3-dihydro-3-hydroxy-1,5-benzothiazepin-4(5H)-one, especially the (2S, 3S)-s-benzyl-5- (2-dimethylaminoethyl)-2-(3-fluoro-4-methoxyphenyl)-2,3-dihydro-3-hydroxy-1,5-benzothiazepin-4(5H)-one isomer;

3-6. 3-acetoxy-8-benzyl-5-(2-dimethylaminoethyl)-2-(3-fluoro-4-methoxyphenyl)-2,3-dihydro-1,5-benzothiazepin-4(5H)-one, especially the (2S, 3S)-3-acetoxY-8-benzyl- 5-(2-dimethylaminoethyl)-2-(3-fluoro-4-methoxyphenyl)- 2,3-dihydro-1,5-benzothiazepin-4(5H)-one isomer;

3-15. 3-acetoxy-8-(4-fluorobenzyl)-5-(2-dimethylaminoethyl)-2-(4-methoxyphenyl)-2,3-dihydro-1,5-benzothiaz- epin-4(5H)-one, especially the (2S, 3S)-3-acetoxy-8- (4-fluorobenzyl)-5-(2-dimethylaminoethyl)-2-(4-methoxy- phenyl)-2,3-dihydro-1,5-benzothiazepin-4(5H)-one isomer;

3-24. 5-(2-dimethylaminoethyl)-8-(4-fluorobenzyl)-2,3-dihydro-3-hydroxy-2-(4-methoxyphenyl)-1,5-benzothiazepin-4(5H)-one, especially the (2S, 3S)-5-(2- dimethylamaminoethyl)-8-(4-fluorobenzyl)-2,3-dihydro-2-(4-methoxyphenyl)-1.5-benzothiazepin-4(5H)-one isomer:

4-1. 5-(2-dimethylaminoethyl)-2,3-dihydro-3-hydroxy-2-(4-methoxyphenyl)-8-(2-thienylmethyl)-1,5-benzothiaz- epin-4(5H)-one, especially the (2S, 3S)-5-(2-dimethyl- aminoethyl)-2,3-dihydro-3-hydroxy-2-(4-methoxyphenyl)-8- (2-thienylmethyl)-1,5-benzothiazepin-4(5H)-one, isomer;

4-2. 3-acetoxy-5-(2-dimethylaminoethyl)-2,3-dihydro-2-(4-methoxyphenyl)-8-(2-thienylmethyl)-1,5-benzothiaz- epin-4(5H)-one, especially the (2S, 3S)-3-acetoxy-5-(2- dimethylaminoethyl)-2,3-dihydro-2-(4-methoxyphenyl)-8- (2-thienylmethyl)-1,5-benzothiazepin-4(5H)-one, isomer;

4-3. 5-(2-dimethylaminoethyl)-8-(2-furylmethyl)-2-(4-methoxyphenyl)-2,3-dihydro-3-hydroxy-1,5-benzothiaz-epin- 4(5H)-one, especially the (2S, 3S)-5-(2-dimethylaminoethyl)- 8-(2-furylmethyl)-2-(4-methoxyphenyl)- 2,3-dihydro-3-hydroxy-1,5-benzochiazepin-4(5H)-one isomer;

4-4. 3-acetoxy-5-(2-dimethylaminoethyl)-8-(2-furyl- methyl)-2-(4-methoxyphenyl)-2,3-dihydro-1,5-benzothiaz- epin-4(5H)-one, especially the (2S, 3S)-3-acetoxy-5-(2- dimethylaminoethyl)-8-(2-furylmethyl)-2-(4-methoxy- phenyl)-2,3-dihydro-1,5-benzothiazepin-4(5H)-one isomer;

The compounds of the present invention may, in general terms, be prepared by reacting a compound of formula (VI):

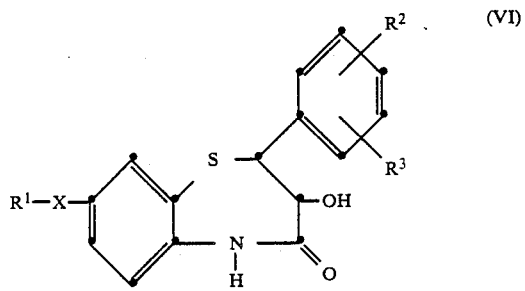

(in which $R^1$, $R^2$, $R^3$ and X are as defined above) with a compound of formula (VIII):

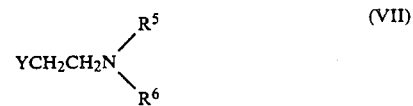

(in which $R^5$ and $R^6$ are as defined above, and Y represents a halogen atom or a sulfonyloxy group, as exemplified below), to give a compound of formula ($I^1$):

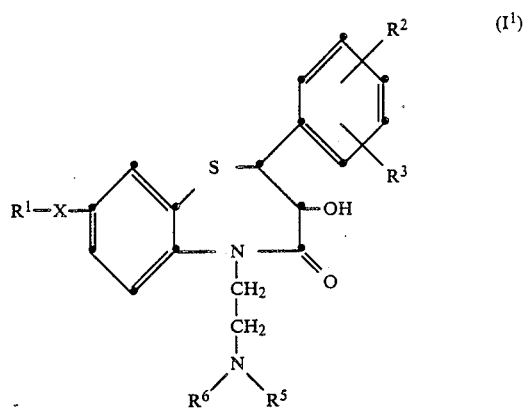

(in which $R^1$, $R^2$, $R^3$, $R^5$, $R^6$ and X are as defined above). and then, if required, reacting said compound of formula ($I^1$) With an acylating agent, to prepare a compound of formula (I) in which $R^4$ represents said aliphatic carboxylic acyl group, said cycloalkylcarbonyl group, said cycloalkoxycarbonyl group, said carbocyclic aromatic carboxylic acyl group, said substituted carbocyclic aromatic carboxylic acyl group, said alkoxycarbonyl group or said benzyloxycarbonyl group.

In more detail, the compounds of the present invention may be prepared as illustrated by the following Reaction Schemes A and B:

Reaction Scheme A:

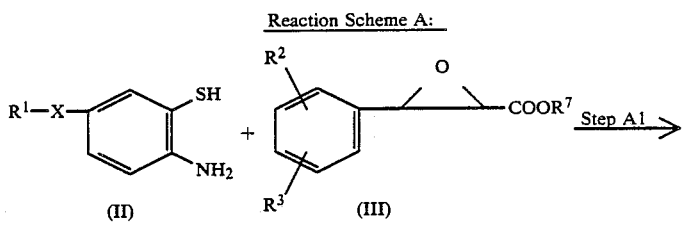

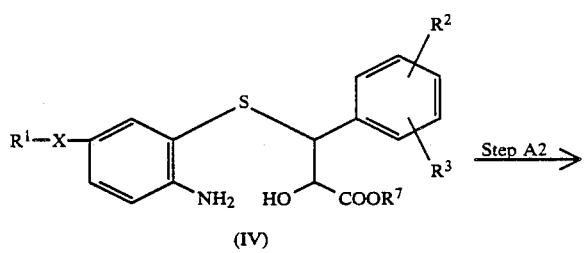

Reaction Scheme A:
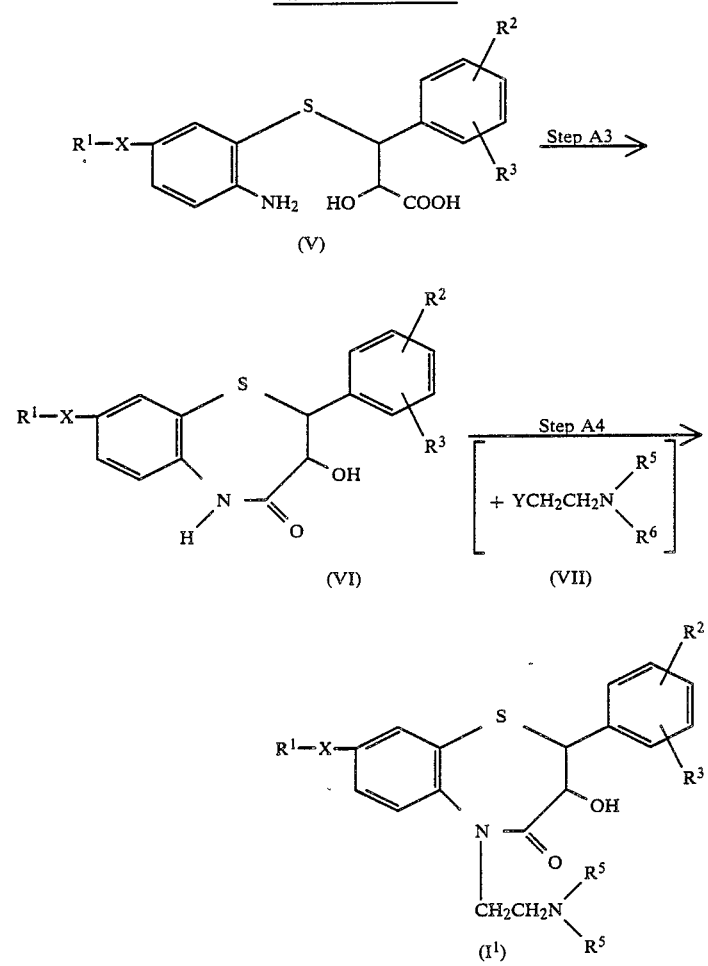
Reaction Scheme B:
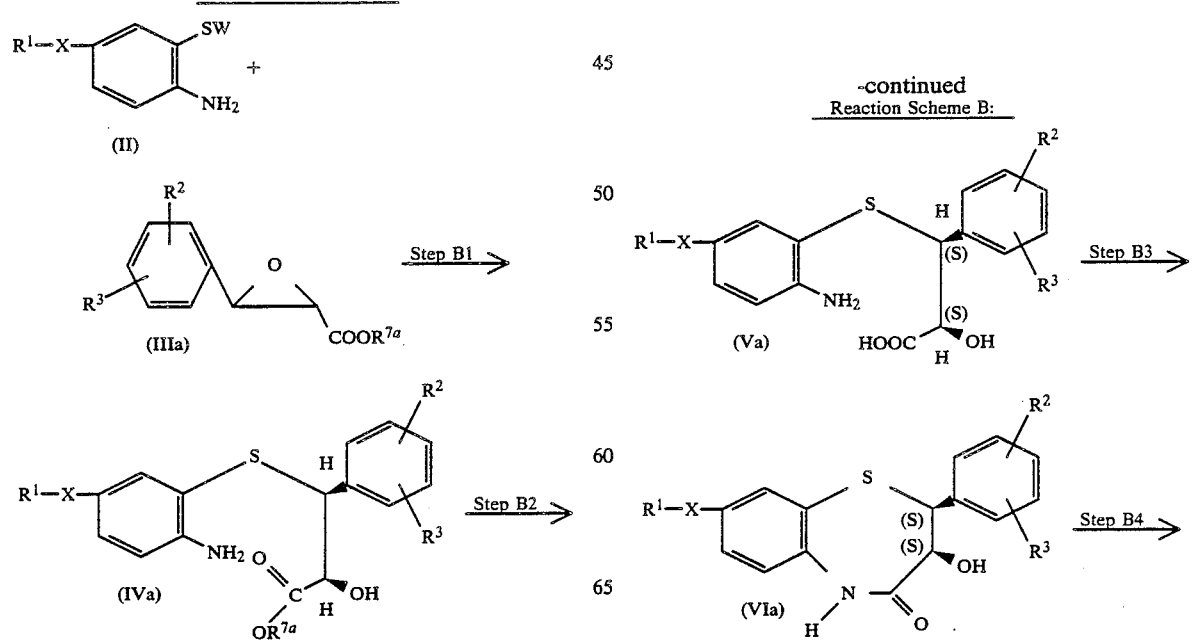

-continued
Reaction Scheme B:

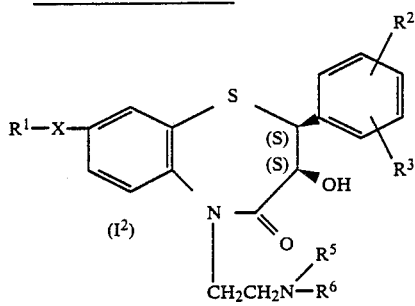

In the above formulae, $R^1$, $R^2$, $R^3$, $R^5$, $R^6$ and X are as defined above;

$R^7$ represents a carboxy-protecting group;

$R^{7a}$ represents an optically active carboxy-protecting group; and

Y represents a halogen atom, such as a chlorine, bromine, iodine or fluorine atom, preferably a chlorine or bromine atom, or a sulfonyloxy group, such as a $C_1-C_4$ alkanesulfonyloxy group (e.g. a methanesulfonyloxy group) or an arylsulfonyloxy group (e.g. a benzenesulfonyloxy or p-toluenesulfonyloxy group).

The nature of the carboxy-protecting group represented by $R^7$ in these reactions is not particularly restricted, as it is eliminated in the course of the reaction, and does not form part of the final product. Examples include: $C_1-C_4$ alkyl groups, such as the methyl, ethyl, propyl and t-butyl groups; and optically active groups, i.e. those which may be represented by $R^{7a}$ including cyclic terpenyl groups and others such as the menthyl (e.g. l-menthyl and isomenthyl), bornyl and α-methylbenzyl groups; preferably the l-menthyl group.

The reactions in the two Reaction Schemes shown above are essentially the same and may be discussed together. In the following discussion, what is said applies to both Reaction Schemes, except where otherwise specifically stated.

In Steps A1 and B1, an aminobenzenethiol compound of formula (II) is reacted with an epoxy compound of formula (III) or (IIIa) to give a hydroxy ester of formula (IV) or (IVa). The reaction is normally and preferably effected in the presence of a solvent, the nature of which is not critical, provided that it has no adverse effect upon the reaction. Examples of suitable solvents include; hydrocarbons, including aliphatic, cycloaliphatic and aromatic hydrocarbons, such as hexane, heptane, cyclohexane, benzene, toluene and xylene; halogenated hydrocarbons. especially halogenated aliphatic hydrocarbons. such as methylene chloride, 1,2-dichloroethane and chloroform; ethers, such as diethyl ether, tetrahydrofuran and dioxane; esters, such as ethyl acetate: and nitriles, such as acetonitrile. Of these, we prefer the hydrocarbons such as benzene and toluene and the halogenated hydrocarbons such as 1,2-dichloroethane.

The reaction will take place over a wide range of temperatures, and the precise reaction temperature chosen is not critical to the invention. In general, we find it convenient to carry out the reaction at a temperature in the range of from room temperature to 130° C. (preferably from 70 to 130° C.) for both Reaction Scheme A and Reaction Scheme B. The time required for the reaction may likewise vary widely, depending on many factors notably the reaction temperature and the nature of the reagents. However, in most cases, a period of from 4 to 48 hours (preferably from 4 to 24 hours) will suffice for Reaction Scheme A and from 4 to 48 hours (preferably from 10 to 40 hours) for Reaction Scheme B.

The compounds of formulae (II). (III) and (IIIa) may be known compounds or may easily be prepared by knoWn methods (for example as described in Japanese Patent Application Kokai No. 268663/1986).

After completion of the reaction, the desired product of formula (IV) or (IVa) may be recovered from the reaction mixture by conventional means, for example simply by evaporation of the solvent. Alternatively, another suitable recovery scheme comprises; adding an aliphatic hydrocarbon such as hexane to the reaction mixture and collecting by filtration the crystals precipitated; or adding water to the reaction mixture and subjecting the resulting mixture to extraction with a water-insoluble organic solvent, followed by evaporation of the solvent. It can, if required, be further purified by conventional methods such as recrystallization or the various chromatography techniques, notably column chromatography or preparative thin layer chromatography.

Furthermore, if $R^7$ represents an optically active carboxy-protecting group. e.g. as shown in Reaction Scheme B. the compound of formula (IV) or (IVa) thus obtainer can be isolated as an optically pure single isomer by means of fractional recrystallization and column chromatography.

In Step B1 of Reaction Scheme B, ring cleavage of the epoxy ring occurs stereospecifically and, forexample, the (2S, 3S)-isomer and the (2R, 3R)-1somer of the compound of formula (IVa) are formed from the (2R, 3S)-epoxy compound of formula (IIIa) and from the (2S, 3R)-epoxy compound of formula (IIIa), respectively. Therefore, when the trans-epoxide of formula (IIIa) [a mixture of the (2R, 3S)-isomer and the (2S, 3R)-isomer is used as the starting material, a mixture of the (2S, 3S)-isomer and the (2R, 3R)-isomer of the compound of formula (IVa) can be obtained. Separation of these isomers can easily be carried out by conventional methods, for example, by recrystallization (preferably using toluene, toluene/hexane or diisopropyl ether as the solvent). thin layer chromatography (preferably using ethyl acetate/hexane or methylene chloride as the deVeloping solvent) or column chromatography. In particular, the desired (2S, 3S)-isomer of the compound of formula (IVa) can be separated efficiently by recrystallization.

In Steps A2 and B2, a compound of formula (V) or (Va) is Prepared by hydrolyzing the compound of formula (IV) or (IVa). When R7 is an alkyl group (other than a t-butyl group) or an optically active menthyl, bornyl or α-methylbenzyl group, this can be accomplished by hydrolysis with an alkali, for example: an alkali metal hydroxide, such as lithium hydroxide, sodium hydroxide or potassium hydroxide; or an alkali metal carbonate, such as sodium carbonate or potassium carbonate. When $R^7$ represents a t-butyl group, this can be accomplished by hydrolysis with a mineral acid, such as hydrochloric acid. The reaction is normally and preferably effected in the presence of a solvent, the nature of which is not critical, proVided that it has no adverse effect upon the reaction. Examples of suitable solvents include: water; alcohols, such as methanol or ethanol; ethers, such as dioxane: and mixtures of water with one or more of these organic solvents. The reaction will take place over a wide range of temperatures, and the precise reaction temperature chosen is not critical to the invention. In general, we find it convenient to carry out the reaction at a temperature in the range of from room temperature to 80° C. (preferably from room temperature to 60° C.). The time required for the reaction may likewise vary widely, depending on many factors, notably the reaction temperature and the nature of the reagents. However, in most cases, a period of from 30 minutes to 24 hours (preferably from 1 hour to 16 hours) will normally suffice.

After completion of the reaction, the reaction product can be obtained as a precipitate in water or in an aqueous alcohol by adjusting the pH to a value of from 2.5 to 4 by the addition of hydrochloric acid or sodium bicarbonate; alternatively, if desired, it can be extracted with an organic solvent, such as ethyl acetate. If necessary, it may be further Purified by conventional methods such as recrystallization or the various chromatography techniques, notably column chromatography or preparative thin layer chromatography.

In Step A3 or B3, a compound of formula (VI) or (VIa) is prepared by the intramolecular condensation of the amino acid of formula (V) or (Va). This reaction may, for example, be effected by heating the amino acid of formula (V) or (Va) at a suitable temperature. e.g. from 100 to 200° C. (preferably from 120 to 160° C.). The reaction is preferably effected in the presence of a solvent, the nature of which is not critical, provided that it has no adverse effect upon the reaction. Examples of suitable solvents include: hydrocarbons, such as toluene, xylene and mesitylene. The time required for the reaction may vary widely, depending on many factors, notably the reaction temperature. However, in most cases, a period of from 6 to 20 hours will normally suffice.

The product of formula (VI) or (VIa) can usually be obtained as a precipitate by cooling the reaction solution, and it can then be isolated by filtration.

Alternatively, the reaction may be carried out in the presence of a dehydrating agent, such as N,N'-dicyclohexylcarbodiimide, carbonyldiimidazole, diphenylphosphorylazide, diethyl cyanophosphate or phosphorus pentachloride. When a dehydrating agent of the carbodiimide type is used, a reagent for forming an active ester, such as 1-hydroxybenzotriazole or N-hydroxysuccinimide, can be added to the reaction system to accelerate the reaction. Also, the reaction can be carried out in the presence of a base, which may be an organic base, such as pyridine, picoline. triethylamine or p-methylmorpholine, or an inorganic base, especially an alkali metal carbonate or bicarbonate, such as sodium carbonate or sodium bicarbonate. The reaction is normally and preferably effected in the presence of a solvent, the nature of which is not critical, provided that it has no adverse effect upon the reaction. Examples of suitable solvents include: amides, such as dimethylformamide, dimethylacetamide, N-methyl-2-pyrrolidone and hexamethylphosphoric triamide; ethers, such as tetrahydrofuran and dioxane; nitrites, such as acetonitrile; alcohols, such as methanol and ethanol: ketones, such as acetone; halogenated hydrocarbons, especially halogenated aliphatic hydrocarbons, such as methylene chloride and chloroform; esters, such as ethyl acetate; and hydrocarbons, which may be aliphatic, cycloaliphatic or aromatic, such as benzene, toluene, hexane and cyclohexane. Of these, we prefer amides such as dimethylformamide. halogenated hydrocarbons such as dichloromethane, hydrocarbons such as toluene and esters such as ethyl acetate.

The reaction will take place over a wide range of temperatures, and the precise reaction temperature chosen is not critical to the invention. In general, we find it convenient to carry out the reaction at a temperature in the range of from 0 to 100° C. (preferably from 0 to 50° C.). The time required for the reaction may likewise vary widely depending on many factors, notably the reaction temperature and the nature of the reagents, especially the dehydratinq agent. However, in most cases, a period of from 3 hours to 24 hours (preferably from 6 to 16 hours) will normally suffice.

The product may sometimes be isolated as crystals from the reaction system, but it can also be obtained by evaporating off the solvent and then purifying the residue by conventional methods such as recrystallization or the various chromatography techniques, notably column chromatography or preparative thin layer chromatography.

In Steps A4 and B4, a compound of formula ($I^1$) or ($I^2$) is prepared by reacting the compound of formula (VI) or (VIa) with a 2-aminoethyl compound of formula (VII) in the presence of a base and in a solvent, the nature of which is not critical, provided that it has no adverse effect upon the reaction. Examples of suitable solvents include: hydrocarbons. Especially aromatic hydrocarbons such as benzene or toluene ethers, such as tetrahydro- furan or dioxane: ketones, such as acetone and methyl ethyl ketone: amides, such as dimethylformamide. dimethylacetamide or N-methyl-2-pyridone; and sulfoxides, such as dimethyl sulfoxide. Of these, we prefer ethers such as tetrahydrofuran, ketones such as acetone and methyl ethyl ketone and amides such as dimethylformamide.

There is likewise no particular limitation on the nature of the base to be used, provided that it does not adversely affect other parts of the molecule, and examples include: metal carbonates, especially alkali metal carbonates, such as sodium carbonate and potassium carbonate; alkali metal bicarbonates, such as sodium bicarbonate or potassium bicarbonate: alkali metal hydrides, such as sodium hydride or lithium hydride; and organic bases, such as 1,5-diazabicyclo[4.3.0]non-5-ene. 1 8-diazabicyclo[5.4.0]undec-7-ene. Of these, we prefer metal carbonates such as sodium carbonate and potassium carbonate and alkali metal hydrides such as sodium hydride. The reaction will take place over a wide range of temperatures, and the precise reaction temperature chosen is not critical to the invention. In general, we find it convenient to carry out the reaction at a temperature in the range of from 0 to 120° C. (preferably from 0 to 80° C.). although this depends on the kinds of the base and the solvent employed. The time required for the reaction may likewise vary widely, depending on many factors, notably the reaction temperature and the nature of the reagents. However, in most cases, a period of from 1 hour to 2 days will normally suffice.

When an inorganic base is used, the reaction may sometimes be accelerated by the addition of a catalytic amount of a pyridine, such as 4-dimethylaminopyridine. or of a crown ether, such as 18-crown-6, to the reaction system.

The desired product of formula ($I^1$) or ($I^2$) can be obtained by conventional recovery techniques. For example, one such comprises: extracting the reaction mixture with an organic solvent such as ethyl acetate; washing the extract with water; drying the product, e.g.

over anhydrous magnesium sulfate: and evaporating off the solvent. If required, the product may be further purified by conventional methods such as recrystallization or the various chromatography techniques, notably column chromatography or preparative thin layer chromatography.

The compound of formula ($I^1$) or ($I^2$) obtained as described above is a compound of formula (1) in which $R^4$ represents a hydrogen atom. Compounds in which $R^4$ represents one of the acyl groups defined above other than a formyl group may be obtained by reacting the compound of formula ($I^1$) or ($I^2$) with a compound of formula $R^8$—z, where $R^8$ represents a $C_2$-$C_6$ aliphatic carboxylic acyl group, a ($C_3$-$C_6$ cycloalkyl)carbonyl group, a ($C_3$-$C_6$ cycloalkoxy)carbonyl group, a $C_7$-$C_{11}$ carbocyclic aromatic carboxylic acyl group, a $C_7$-$C_{11}$ carbocyclic aromatic carboxylic acyl group having at least one substituent selected from the group consisting of $C_1$-$C_6$ alkyl groups, $C_1$-$C_6$ alkoxy groups and halogen atoms, a $C_2$-$C_7$ alkoxycarbonyl group or a benzyloxycarbonyl group: and z represents a halogen atom, e g. a fluorlne, chlorine, bromine or iodine atom, or a group of formula —O—$R^8$.

This reaction is preferably effected in the presence of a base and normally and preferably in the presence of a solvent.

Compounds in which $R^4$ represents a formyl group may be obtained by reacting the compound of formula ($I^1$) or ($I^2$) with formic acid in the presence of a carboxylic acid anhydride, such as acetic anhydride, normally and preferably in the presence of a solvent.

In either case, the nature of the solvent employed is not critical, provided that it has no adverse effect upon the reaction. Examples of suitable solvents include: hydrocarbons, including aliphatic and aromatic hydrocarbons, such as hexane, benzene and toluene; halogenated hydrocarbons, especially halogenated aliphatic hydrocarbons, such as methylene chloride and chloroform: ethers, such as diethyl ether and tetrahydrofuran: and esters, such as ethyl acetate. Of these, we prefer halogenated hydrocarbons such as methylene chloride.

The nature of the base is likewise not critical, provided that it does not adversely affect other parts of the molecule, and examples include: organic bases such as triethylamine, pyridine and N-methylmorpholine. Such organic bases may also be used as the reaction solvent, in which case, they are preferably used in a large excess.

The reaction will take place over a wide range of temperatures, and the precise reaction temperature chosen is not critical to the invention. In general, we find it convenient to carry out the reaction at a temperature in the range of from 0 to 80° C. (preferably from 0 to 50° C.). The time required for the reaction may likewise vary widely, depending on many factors, notably the reaction temperature and the nature of the reagents. However, in most cases, a period of from 1 to 24 hours (preferably from 3 to 20 hours) will normally suffice.

The desired product can be obtained from the reaction mixture by conventional techniques. For example, one suitable recovery technique comprises: extracting the reaction mixture with an organic solvent such as ethyl acetate; washing the extract with water; drying it, e.g. over anhydrous magnesium sulfate; and then evaporating off the solvent. If required, the product may be further purified by conventional methods such as recrystallization of the various chromatography techniques, notably column chromatography or preparative thin layer chromatography.

The compounds of formula (I) of the present invention can be converted to pharmaceutically acceptable salts by treatment with an acid, as is well known in the art. For example, salts can be prepared by dissolving the compound of formula (I) in an organic solvent (for example: an ester, such as ethyl acetate; an alcohol, such as methanol or ethanol; or a halogenated hydrocarbon, such as methylene chloride), adding an equimolar or excess amount of an acid (such as hydrogen chloride in dioxane, fumaric acid in methanol or tartaric acid in methanol), evaporating off the solvent and effecting crystallization or solidification from an organlc liquid such as diethyl ether or isopropyl ether.

Examples of such acid addition salts include: salts with inorganic acids, such as hydrochloric acid, hydrobromic acid, sulfuric acid, nitric acid and phosphoric acid: and salts with organic acids, including organic carboxylic acids and organic sulfonic acids, such as maleic acid, fumaric acid, oxalic acid citric acid, tartaric acid, methanesulfonic acid, p-toluenesulfonic acid and benzenesulfonic acid.

The compounds of the present invention have exhibited excellent calcium channel blocking action and hypotensive activity with a high persistency in spontaneously hypertensive rats (SMR), as shown below, which indicates that they may be very useful for the prophylaxi and therapy of diseases of the circulatory organ system.

The benzothizepine derivatives of the present invention can be used for the prophylaxis and therapy of diseases of the circulatory organ system of animals, especially mammals, including humans. The compounds may be administered by any suitable route, for example the parenteral route (e.g. by intravenous, subcutaneous or intramuscular injection) or by suppository, or by the oral route (for example in the form of a tablet, capsule, powder or granule).

If desired, the compound of the invention may be administered as such, but it is preferably employed in association with a conventional pharmaceutically acceptable carrier, excipient or diluent, appropriate to the particular route of administration.

For example, the composition may contain suspending agents, stabilizing agents or dispersing agents and it may be provided as a powder which, prior to administration, is dissolved in a suitable solvent, for example a pyrogen-free sterilized aqueous solvent. Compositions for oral use may be provided as tablets, capsules, powders, granules or syrups containing an appropriate amount of the compound of the invention. Compositions for injection are preferably provided as an ampoule containing a unlt dose or as a vial containing multiple doses.

The dosage of the compounds of the invention will vary, depending upon the severity and nature of the disease, as well as the route, frequency and period of administration. However, a suitable dose for an adult human would be in the range of from 1 to 1000 mg per day, especially from 1 to 100 mg per day, for oral administration, or 0.1 to 100 mg per day, especially from 0.5 to 30 mg per day, for intravenous injection, which may be administered in a single dose or in divided doses, e.g. once or twice a day.

The preparation of the compounds of the present invention is further illustrated by the following nonlimiting Examples. The preparation of certain starting materials used in the preparation of the compounds of the invention is illustrated by the subsequent preparations.

EXAMPLE 1

(±)-Cis-5-(2-dimethylaminoethyl)-2,3-dihydro-3-hydroxy-2-(4-methoxyphenyl)-8-phenoxy-1,5-benzothiazepin-4(5H)-one

1(a) Ethyl 3-(2-amino-5-phenoxyphenyl)thio-2-hydroxy-3-(4-methoxyphenyl)propionate 5.5 g of 2-amino-5-phenoxybenzenthiol (prepared as described in Preparation 2) and 1.86 g of (±)-ethyl 3-(4-methoxyphenyl)glycidate were stirred in 50 ml of toluene at 90° C. for 14 hours. At the end of this time, the reaction mixture was cooled: it was then purified by chromatography through a silica gel column using a 3 : 1 by volume mixture of cyclohexane and ethyl acetate as the eluent, to obtain 3.28 g of the title compound as a viscous oil.

Nuclear Magnetic Resonance Spectrum (CDCl$_3$) δ ppm:
 1.19, (3H, triplet, J=7 Hz);
 3.72, (3H, singlet);
 3.7–4.7, (7H, multiplet);
 6.5–7.6. (12H, multiplet).

1(b) 3-(2-Amino-5-phenoxyphenyl)thio-2-hydroxy-3-(4-methoxyphenyl)propionic acid 3.28 g of ethyl 3-(2-amino-5-phenoxyphenyl)thio-2-hydroxy-3-(4-methoxyphenyl)propionate [prepared as described in step (a) above] were dissolved in 20 ml of ethanol, and a solution of 615 mg of 85% (by weight purity) caustic potash dissolved in 5 ml of water were added to the resulting solution. The solution was then stirred at room temperature for 2 hours, after which 50 ml of water and 70 ml of ethyl acetate Were added thereto, followed by an aqueous solution of potassium hydrogen sulfate sufficient to adjust the pH to a value of 3. The precipitate which formed was collected by filtration, to give 1.44 g of the title compound. The filtrate was separated, and the ethyl acetate layer was recovered, washed, dried over anhydrous magnesium sulfate, and concentrated by evaporation under reduced pressure. The residue was triturated in diethyl ether and then filtered to give a further 0.76 9 of the title compound. This substance was used in the subsequent step without purification.

1(c) (±)-Cis-2,3-dihydro-3-hydroxy-2-(4-methoxyphenyl)-8-phenoxy-1,5-benzothiazepin-4(5H)-one 2.2 g of 3-(2-amino-5-phenoxyphenyl)thio-2-hydroxy-3-4-methoxyphenyl)propionic acid [prepared as described in step (b) above] were dissolved in 11 ml of dimethylformamide, and 1.38 ml of diphenylphosphorylazide was added, whilst ice-cooling, the mixture was then stirred for 30 minutes. At the end to this time, 1.38 ml of N-methylmorpholine was added to the mixture, which was then stirred at the same temperature for 30 minutes, and then at room temperature for 2 hours. After this, an aqueous solution of sodium chloride was added and the mixture was extracted twice with ethyl acetate. The extracts were combined, washed with an aqueous solution of sodium chloride, dried over anhydrous magnesium sulfate and concentrated by evaporation under reduced pressure. The residue was triturated in diethyl ether, filtered and washed with diethyl ether, to give 1.13 g of the title compound.

Nuclear Magnetic Resonance Spectrum (hexadeuterated dimethyl sulfoxide) δ ppm:
 3.79, (3H, singlet);
 3.80, (1H, doublet, J=7 Hz);
 4.41, (1H, triplet. J=7 Hz);
 5.01, (1H, doublet, J=7 Hz);
 6.6–7.7, (12H, multiplet);
 10.29, (1H, broad singlet).

1(d) (±)-Cis-5-(2-dimethylaminoethyl)-2,3-dihydro-3-hydroxy-2-(4-methoxyphenyl)-8-1,5-benzothiazepin-4(5H)-one 787 mg of (±)-cis-2,3-dihydro-3-hydroxy-2-(4-methoxyphenyl)-8-phenoxy-1,5-benzoihiazepin-4(5H)-one [prepared as described in step (c) above]were dissolved in 30 ml of acetone, and 432 mg of dimethylaminoethyl chloride hydrochloride, 415 mg of potassium carbonate and small amounts of 4-dimethylaminopyridine and of 18-crown-6 were added to the resulting solution. The mixture was then heated under reflux for 24 hours. At the end of this time the reaction mixture was poured into an aqueous solution of sodium chloride, and extracted twice with ethyl acetate. The extracts were combined, washed with an aqueous solution of sodium chloride, dehydrated over anhydrous magnesium sulfate, and then concentrated by evaporation under reduced pressure. The composition was purified by chromatography through a silica gel column, using a 20 : 1 by volume mixture of methylene chloride and methanol as the eluent, to give 773 mg of the title compound as a gum.

Nuclear Magnetic Resonance Spectrum (CDCl$_3$) δ ppm:
 2.1–3.1, (2H, multiplet);
 2,30, (6H, singlet);
 3.3–4.0, (1H, multiplet);
 3.80, (3H, singlet);
 4.0–4.8, (2H, multiplet);
 4.91, (1H, doublet, J=7 Hz);
 6.8–7.7, (12H, multiplet).

EXAMPLE 2

(±)-Cis-3-acetoxy-5-(2-dimethylaminoethyl)-2,3-dihydro-2-(4-methoxyphenyl)-8-phenoxy-1,5-benzothiazepin-4(5H)-one 773 mg of (±)-cis-5-(2-dimethylaminoethyl)-2,3-dihydro-3-hydroxy-2-(4-methoxyphenyl)-8-phenoxy-1 5- benzothiazepin-4(5H)-one (prepared as described in Example 1) were dissolved in 5 ml of pyridine, and 1 ml of acetic anhydride was added at room temperature to the resulting solution. The mixture was then left to stand for 14 hours. At the end of this time, 2 ml of ethanol were added to the reaction mixture, and after the mixture had been left to stand for 30 minutes, 30 ml of ethyl acetate were added. The mixture was then washed with an aqueous solution of sodium bicarbonate and with an aqueous solution of sodium chloride in that order, after which it was dried over anhydrous magnesium sulfate, and concentrated by evaporation under reduced pressure to obtain a concentrate. This concentrate was purified by chromatography through a silica gel column, using a 20 : 1 by volume mixture of methylene chloride and methanol as the eluent, to give the title compound as a solid.

A portion of this title compound was dissolved in 50 ml of diethyl ether and, whilst stirring, 1 ml of a 4N solution of hydrogen chloride in dioxane was added thereto. The precipitate which formed was separated by filtration, washed with diethyl ether and then dried to give 887 mg of the hydrochloride of the title compound.

Title compound

Nuclear Magnetic Resonance Spectrum (CDCl$_3$) δ ppm:
1.88, (3H, singlet);
2.27, (6H, singlet);
2.1–3.1, (2H, multiplet);
3.2–4.0, (1H, multiplet);
3.75, (3H, singlet);
4.0–4.7, (1H, multiplet);
4.96, (1H, doublet, J=7 Hz);
5.20, (1H doublet, J=7 Hz);
6.6–7.7, (12H, multiplet).

Hydrochloride of the title compound m.p. 119–124° C.
Nuclear Magnetic Resonance Spectrum (hexadeuterated dimethyl sulfoxide) δ ppm:
1.84 (3H, singlet);
2.84 (6H, singlet);
2.5–3.8 (2H, multiplet);
3.79 (3H, singlet);
3.8–4.8 (2H, multiplet);
4.9–5.4 (2H, multiplet);
6.6–7.9 (12H, multiplet).
Infrared Absorption Spectrum (Nujol - trade mark) $\nu_{max}$cm$^{-1}$: 745. 1675.

EXAMPLE 3

(±)-Cis-5-(2-dimethylaminoethyl)-2-(3-fluoro-4-methoxy-phenyl)-2,3-dihydro-3-hydroxy-8-phenoxy-1,5-benzothiazepin-4(5H)-one

3(a) Ethyl 3-(2-amino-5-phenoxyphenyl)thio-3-(3-fluoro-4-methoxyphenyl)- 2-hydroxypropionate Following a procedure similar to that described in Example 1(a), 4.8 g of 2-amino-5-phenoxybenzenethiol (prepared as described in preparation 2) and 2.5 g of (±)-ethyl 3-(3-fluoro-4-methoxyphenyl)glycidate were reacted in 50 ml of toluene, and the product was purified by silica gel column chromatography, to give 1.85 g of the title compound viscous liquid.
Nuclear Magnetic Resonance Spectrum (CDCl$_3$) δ ppm:
1.20, (3H, triplet);
3.80, (3H, singlet);
3.5–5.0, (7H, multiplet);
6.4–7.7, (11H, multiplet).

3(b) 3-(2-Amino-5-phenoxyphenyl)thio-3-(3-fluoro-4-methoxyphenyl)-2-hydroxypropionic acid Following a procedure similar to that described in Example 1(b), 1.85 g of ethyl 3-(2-amino-5-phenoxyphenyl)thio-3-(3-fluoro-4-methoxyphenyl)-2-hydroxypropionate [prepared as described in step (a) above] was hydrolyzed in ethanol using an aqueous solution prepared from 334 mg of 85% caustic potash. After water and ethyl acetate had been added to the reaction mixture, its pH was adjusted to a value of 3 by the addition of an aqueous solution of potassium hydrogen sulfate. The mixture was then extracted with ethyl acetate. The extract was washed with an aqueous solution of sodium chloride, dried over anhydrous magnesium sulfate and then concentrated by evaporation under reduced pressure. The residue Was triturated in diethyl ether, filtered and dried to give 922 mg of the title compound.

3(c) (±)-Cis-2-(3-fluoro-4-methoxyphenyl)-2,3-dihydro-3-hydroxy-8-phenoxy-1,5-benzothiazepin-4(5H)-one 922 mg of 3-(2-amino-5-phenoxyphenyl)thio-3-(3-fluoro-4-methoxyphenyl)-2-hydroxypropionic acid [prepared as described in step (b) above] were subjected to ring closure in the same manner as described in Example 1(c) using 0.59 ml of diphenylphosphorylazide and 0.59 ml of N-methylmorpholine The product was then extracted and purified as described in Example 1(c), to give 432 mg of the title compound as a powder, melting at 246–247° C.
Nuclear Magnetic Resonance Spectrum (hexadeuterated dimethyl sulfoxide) δ ppm:
3.84, (3H, singlet);
4.35, (1H, triplet, J=7 Hz);
4.75, (1H, doublet, J=7 Hz);
5.06, (1H, doublet J=7 Hz);
6.7–7.6, (11H, multiplet);
10.32, (1H, broad singlet).

3(d) (±)-Cis-5-(2-dimethylaminoethyl)-2-(3-fluoro-4-methoxyphenyl)-2,3-dihydro-3-hydroxy-8-phenoxy-1,5- benzothiazepin-4(5H)-one 400 mg of (±)-cis-2-(3-fluoro-4-methoxyphenyl)-2,3-dihydro-3-hydroxy-8-phenoxy-1,5-benzothiazepin-4(5H)-one [prepared as described in step (c) above] were alkylated with 210 mg of dimethylaminoethyl hydrochloride hydrochloride, 202 mg of potassium carbonate and small amounts of 4-dimethylaminopyridine and 18-crown-6 in 30 ml of acetone in the same manner as described in Example 1(d). The product was then extracted and purified as described in Example 1(d), to give 230 mg of the title compound as a gum.
Nuclear Magnetic Resonance Spectrum (CDCl$_3$) δ ppm:
2.28, (6H, singlet);
2.1–3.0, (2H, multiplet);
2.98, (1H, broad singlet);
3.2–4.0, (1H, multiplet);
3.83, (3H, singlet);
4.2–4.9, (1H, multiplet);
4.30, (1H, doublet, J=7 Hz);
4.82, (1H, doublet J=7 Hz);
6.6–7.7, (11H, multiplet).

EXAMPLE 4

(±)-Cis-3-acetoxy-5-(2-dimethylaminoethyl)-2-(3-fluoro-4-methoxyphenyl)-2,3-dihydro-8-phenoxy-1,5-benzothiazepin-4(5H)-one 455 mg of (±)-cis-5-(2-dimethylaminoethyl)-2-(3-fluoro-4-methoxyphenyl)-2,3-dihydro-3-hydroxy-8-phenoxy-1,5-benzothiazepin-4(5H)-one (prepared as described in Example 3) were acetylated in the same manner as described in Example 2 in 2 ml of pyridine using 1 ml of acetic anhydride and the product was isolated and purified also as described in Example 2, to give 480 mg of the title compound as a gum.

Nuclear Magnetic Resonance Spectrum (CDCl$_3$) δ ppm:
  1.91, (3H, singlet);
  2.28, (6H, singlet);
  2.1–3.2, (2H, multiplet);
  3.3–4.1, (1H, multiplet);
  3.87, (3H, singlet);
  4.2–4.8, (1H, multiplet);
  4.98, (1H, doublet J=7 Hz);
  5.22, (1H doublet J=7 Hz);
  6.7–7.7, (11H multiplet).

The whole of the (±)-cis-3-acetoxy-5-(2-dimethylaminoethyl-2-(3-fluoro-4-methoxyphenyl)-2,3-dihydro-8- phenoxy-1,5-benzothiazepin-4(5H)-one prepared as described above was dissolved in 20 ml of diethyl ether, and 0.26 ml of a 4N solution of hydrogen chloride in dioxane was added to the solution, whilst stirring. The precipitate which formed was filtered off and dried to give 504 of the hydrochloride of the title compound, melting at 116–122° C.

Infrared Absorption Spectrum (Nujol) $v_{max}$ cm$^1$: 1745, 1675.

EXAMPLE 5

(±)-Cis-5-(2-dimethylaminoethyl)-2,3-dihydro-3-hydroxy-2-(3,4-methylenedioxyphenyl)-8-phenoxy-1,5-benzothiazepin-4(5H)-one

5(a) Ethyl 3-(2-amino-5-phenoxyphenyl)thio-2-hydroxy-3-(3,4-methylenedioxyphenyl)propionate Following a procedure similar to that described in Example 1(a), but using 9.2 g of 2-amino-5-phenoxybenzenethiol (prepared as described in preparation 2) and 10.0 g of (±)-ethyl 3-(3,4-methylenedioxyphenyl)glycidate, 15.2 g of the title compound were obtained as a syrup.

Nuclear Magnetic Resonance Spectrum (CDCl$_3$) δ ppm:
  1.20, (3H, triplet, J=7.5 Hz);
  3.82, (3H, broad singlet);
  4.14, (2H, quartet, J=7.5 Hz);
  4.42, (1H, doublet J=3.5 Hz);
  4.50, (1H, doublet J=3.5 Hz);
  5.90 (2H, singlet);
  6.5–7.4, (11H, multiplet).

5(b) 3-(2-Amino-5-phenoxyphenyl)thio-2-hydroxy-3-(3,4-methylenedioxyphenyl)propionic acid Following a procedure similar to that described in Example 1(b), 15.2 g of ethyl 3-(2-amino-5-phenoxyphenyl)thio-2-hydroxy-3-(3,4-methylenedioxyphenyl)-propionate [prepared as described in step (a) above] were hydrolyzed with caustic potash to give 7.84 g of the title compound as a powder, melting at 158–159° C. This product was used in the next step without further purification.

5(c) (±)-Cis-2,3-dihydro-3-hydroxy-2-(3,4-methylenedioxyphenyl)- -8-phenoxy-1,5-benzothiazepin-4(5H)-one Following a procedure similar to that described in Example 1(c), but using 7.34 g of 3-(2-amino-5-phenoxyphenyl)thio-2-hydroxy-3-(3,4-methylenedioxyphenyl)-propionic acid [prepared as described in step (b) above], 4.5 g of the title compound were obtained as crystals, melting at 227.5–229.5° C.

Nuclear Magnetic Resonance Spectrum (hexadeuterated dimethyl sulfoxide) δ ppm:
  4.36, (1H, triplet, J=6.5 Hz);
  4.76, (1H, doublet, J=6.5 Hz);
  5.06, (1H, doublet, J=6.5 Hz); 6.01, (2H, singlet);
  6.78–7.59, (11H, multiplet); 10.27, (1H, singlet).

5(d) (±)-Cis-5-(2-dimethylaminoethyl)-2,3-dihydro-3-hydroxy-2-(3,4-methylenedioxyphenyl)-8-phenoxy-1,5-benzothiazepin-4(5H)-one Following a procedure similar to that described in Example 1(d), but using 0.50 g of (±)-cis-2,3-dihydro-3-hydroxy-2-(3,4-methylenedioxyphenyl)-8-phenoxy-1,5-benzothiazepin-4(5H)-one [prepared as described in step (c) above], 0.58 g of the title compound was obtained as an amorphous powder.

Nuclear Magnetic Resonance Spectrum (CDCl$_3$) δ ppm:
  2.27, (6H, singlet);
  2.10–3.05, (3H, multiplet);
  3.38–3.90, (1H, multiplet);
  4.31, (1H, doublet J=7.5 Hz);
  4.25–4.90, (1H, multiplet);
  4.84, (1H, doublet J=7.5 Hz);
  5.95, (2H, singlet);
  6.66–7.65, (11H, multiplet).

EXAMPLE 6

(±)-Cis-3-acetoxy-5-(2-dimethylaminoethyl)-2,3-dihydro- 2-(3,4-methylenedioxyphenyl)-8-phenoxy-1,5-benzothiazepin-(5H)-one Following a procedure similar to that described in Example 2, but using 0.58 g of (±)-cis-5-(2-dimethylaminoethyl)-2,3-dihydro-3-hydroxy-2-(3,4-methylenedioxy- phenyl)-8-phanoxy-1,5-benzothiazepin-4(5H)-one (prepared as described in Example 5). 0.58 g of the title compound was obtained as an amorphous powder.

Nuclear Magnetic Resonance Spectrum (CDCl$_3$) δ ppm:
  1.91, (3H, singlet);
  2.29, (6H, singlet);
  2.10–3.10, (2H, multiplet);
  3.30–3.90, (1H, multiplet);
  4.20–4.80, (1H, multiplet);
  4.96, (1H, doublet, J=1 Hz);
  5.21 (1H, doublet, J=1 Hz);
  5.98, (2H, singlet);
  6.66–7.65, (11H, multiplet).

This compound was treated with a 4N solution of hydrogen chloride in dioxane in the same manner as described in Example 2 to give the hydrochloride of the title compound as crystals, melting at 144–146° C.

Infrared Absorption Spectrum (Nujol) $v_{max}$ cm$^{-1}$: 1745, 1670.

EXAMPLE 7

(±)-Cis-2-(3-chloro-4-methoxyphenyl)-5-(2-dimethyl- aminoethyl)-2,3-dihydro-3-hydroxy-8-phenoxy-1,5-benzo- thiazepin-4(5H)-one

7(a) Ethyl 3-(2-amino-5-phenoxyphenyl)thio-3-(3-chloro-4-methoxyphenyl)-2-hydroxypropionate Following a procedure similar to that described in Example 1(a), but using 6.7 g of 2-amino-5-phenoxybenzenethiol (prepared as described in Preparation 2) and 7.83 g of (±)-ethyl 3-(4-nethoxyphenyl) glycidate 13.4 g of the title compound were obtained as a gum.

Nuclear Magnetic Resonance Spectrum (CDCl$_3$) δ ppm:
1.20, (3M, triplet, J=7 Hz);
3.79, (3H, singlet);
3.7–4.6, (7M, multiplet);
6.55–7.4, (11H, multiplet).

7(b) 3-(2-Amino-5-phenoxyphenyl)thio-3-(3-chloro-4-methoxyphenyl)-2-hydroxypropionic acid Following a procedure similar to that described in Example 1(b), but using 13.4 g of ethyl 3-(2 amino-5-phenoxyphenyl)thio-3-(3-chloro-4-methoxyphenyl)-2-hydroxypropionate [prepared as described in step (a) above], 10.6 g of the title compound were obtained as a powder, melting at 168–170° C.

This compound was used in the next step without further purification.

7(c) (±)-Cis-2-(3-chloro-4-methoxyphenyl)-2,3-dihydro-3-hydroxy-8-phenoxy-1,5-benzothiazepin-4(5H)-one Following a procedure similar to that described in Example 1(c), but using 10.11 g of 3-(2-amino-5-phenoxy- phenyl)thio-3-(3-chloro-4-methoxyphenyl)-2-hydroxypropionic acid [prepared as described in step (b) above], 6.00 g of the title compound were obtained as crystals, melting at 262–264° C.

Nuclear Magnetic Resonance Spectrum (hexadeuterated dimethyl sulfoxide) δ ppm:
3.86, (3H, singlet);
4.40, (1H, multiplet);
4.83, (1H, multiplet);
5.09, (1H, doublet, J=7 Hz);
7.0–7.6, (11H, multiplet); 10.35 (1H, singlet).

7(d) (±)-Cis-2-(3-chloro-4-methoxyphenyl)-5-(2-dimethylaminoethyl)-2,3-dihydro-3-hydroxy-8-phenoxy-1,5-benzothiazepin-4(5H)-one Following a procedure similar to that described in Example 1(d), but using 0.50 g of (±)-cis-2-(3-chloro-4-methoxyphenyl)-2,3-dihydro-3-hydroxy-8-phenoxy-1,5-benZothiazepin-4(5H)-one [prepared as described in step above], 0.63 g of the title compound was obtained as a gum.

Nuclear Magnetic Resonance Spectrum (CDCl$_3$) δ ppm:
2.26, (6H, singlet);
2.1–2.75, (2H, multiplet);
3.08, (1H, singlet);
3.3–3.8, (1H, multiplet;
3.83, (3H, singlet);
4.28, (1H, doublet, J=7 Hz);
4.2–4.8, (1H, multiplet);
4.78, (1H, doublet, J=7 Hz);
6.75–7.6, (11H, multiplet).

EXAMPLE 8

(±)-Cis-3-acetoxy-2-(3-chloro-4-methoxyphenyl)-5-(2-dimethylaminoethyl)-2,3-dihydro-8-phenoxy-1,5-benzothiazepin-4(5H)-one Following a procedure similar to that described in Example 2, but using 0.61 g of (±)-cis-2-(3-chloro-4-methoxyphenyl)-5-(2-dimethylaminoethyl)-2,3-dihydro-3-hydroxy-8-phenoxy-1,5-benzothiazepin-4(5H)-one (prepared as described in Example 7). 0.63 g of the title compound was obtained as a gum.

Nuclear Magnetic Resonance Spectrum (CDCl$_3$) δ ppm:
1.90, (3H, singlet);
2,31, (6H, singlet);
2.2–3.0, (2H, multiplet);
3.3–3.9, (1H, multiplet);
3.84, (3H, singlet);
4.1–4.6, (1H, multiplet);
4.88, (1H, doublet, J=7 Hz);
5.14, (1H, doublet, J=7 Hz);
8.8–7.55 (11H, multiplet).

This compound was treated with a 4N solution of hydrogen chloride in dioxane in the same manner as described in Example 2 to give the hydrochloride of the title compound as an amorphous powder, melting at 142–145° C.

Infrared Absorption Spectrum (Nujol) $v_{max}$ cm$^{-1}$: 1745, 1670.

EXAMPLE 9

(±)-Cis-5-(2-dimethylaminoethyl)-2,3-dihydro-3-hydroxy-2-(4-methoxyphenyl)-8-phenylthio-1,5-benzothiazepin-4(5H)-one

9(a) Methyl 3-(2-amino-5-phenylthiophenyl)thio-2-hydroxy-3-(4-methoxyphenyl) propionate Following a procedure similar to that described in Example 1(a), but using 4 g of 2-amino-5-phenylthiobenzenethiol (prepared as described in Preparation 4) and 4.06 g of (±)-methyl 3-(4-methoxyphenyl)glycidate, 5.59 g of the title compound were obtained as a colorless powder, melting at 103–105° C.

Nuclear Magnetic Resonance Spectrum (CDCl$_3$) δ ppm:
3.61, (3H, singlet);
3.65, (3H, singlet);
3.5–3.85, (3H, broad peak);
4.41, (1H, doublet J=3 Hz);
4.51, (1H, doublet, J=3 Hz);
6.5–7.4, (12H, multiplet).

9(b) 3-(2-Amino-5-phenylthiophenyl)thio-2-hydroxy-3-(4-methoxyphenyl)propionic acid Following a procedure similar to that described in Example 1(b), but using 5.50 g of methyl 3-(2-amino-5-phenylthiophenyl)thio-2-hydroxy-3-(4-methoxyphenyl)propionate [prepared as described in step (a) above], 4.43 g of the title compound were obtained as a powder. melting at 147–149° C.

Nuclear Magnetic Resonance Spectrum (hexadeuterated dimethyl sulfoxide) δ ppm:
3.65, (3H, singlet);
4.25–4.50, (2H, multiplet);

6.5–7.4, (16H, multiplet).

9(c)
(±)-Cis-2,3-dihydro-3-hydroxy-2-(4-methoxyphenyl)-8-phenylthio-1,5-benzothiazepin-4(5H)-one Following a procedure similar to that described in Example 1(c), but using 4.40 g of 3-(2-amino-5-phenylthiophenyl)thio-2-hydroxy-3-(4-methoxyphenyl)propionic acid [prepared as described in step (b) above], 0.68 g of the title compound was obtained as crystals, melting at 195–198° C.

Nuclear Magnetic Resonance Spectrum (mixture of hexadeuterated dimethyl sulfoxide and CDCl$_3$) δ ppm:
- 3.72, (3H, singlet);
- 3.79, (1H, singlet);
- 4.38, (1H, doublet, J=6.5 Hz);
- 5.03, (1H, doublet J=6.5 Hz);
- 6.75–7.55 (12H, multiplet).

9(d) (±)-Cis-5-(2-dimethylaminoethyl)-2,3-dihydro-3-hydroxy-2-(4-methoxyphenyl)-8-phenylthio-1,5-benzothiazepin-4(5H)-one Following a procedure similar to that described in Example 1(d), but using 0.30 g of (±)-cis-2,3-dihydro-3-hydroxy-2-(4-methoxyphenyl)-8-phenylthio-1,5-benzo-thiazepin-4(5H)-one [prepared as described in step (c) above]. 0.25 g of the title compound was obtained as a gum.

Nuclear Magnetic Resonance Spectrum (CDCl$_3$) δ ppm:
- 2.30, (6H, singlet);
- 2.4–2.9, (2H, multiplet);
- 2.84, (1H broad singlet);
- 3.78, (3H, singlet);
- 3.4–3.9, (1H, multiplet);
- 4.30, (1H, doublet, J=7 Hz);
- 4.15–4.7, (1H, multiplet);
- 4.88, (1H, doublet, J=7 Hz);
- 6.8–7.6, (12H, multiplet).

EXAMPLE 10
(±)-Cis-3-acetoxy-5-(2-dimethylaminoethyl)-2,3-dihydro-2-(4-methoxyphenyl)-8-phenylthio-1,5-benzothiazepin-4(5H)-one Following a procedure similar to that described in Example 2, but using 0.25 g of (±)-cis-2,3-dihydro-5-(2-dimethylaminoethyl)-3-hydroxy-2-(4-methoxyphenyl)-8-phenylthio-1,5-benzothiazepin-4(5H)-one (prepared as described in Example 9), 0.16 g of the title compound was obtained as a gum.

Nuclear Magnetic Resonance Spectrum (CDCl$_3$) δ ppm:
- 1.88, (3H, singlet);
- 2.25, (6H, singlet);
- 2.2–3.0, (2H, multiplet);
- 3.4–3.9, (1H, multiplet);
- 3.77, (3H, singlet); 4.1–4.6, (1H, multiplet);
- 4.95, (1H, doublet, J=7 Hz);
- 5.14, (1H, doublet, J=7 Hz);
- 6.85–7.6, (12H, multiplet).

This compound was treated with a 4N solution of hydrogen chloride in dioxane in the same manner as described in Example 2 to give the hydrochloride of the title compound as an amorphous solid.

Infrared Absorption Spectrum (Nujol) $\nu_{max}$ cm$^{-1}$: 1740, 1670

EXAMPLE 11
(2S, 3S)-5-(2-Dimethylaminoethyl)-2,3-dihydro-3-hydroxy-2-(4-methoxyphenyl)-8-phenoxy-1,5-benzothiazepin-4(5H)-one

11(a) l-Menthyl (2S, 3S)-3-(2-amino-5-phenoxyphenyl)thio-2-hydroxy-3-(4-methoxyphenyl)propionate A solution of 5.4 g of l-menthyl trans-2,3-epoxy-3-(4-methoxyphenyl)propionate (prepared as described in preparation 5) and 4.2 g to 2-amino-5-phenoxybenzenethiol in 60 ml of toluene was stirred at 90° C. for 16 hours. At the end of this time, 60 ml of hexane were added to the reaction mixture, and the resulting mixture was cooled. The crystals which precipitated were collected by filtration and washed with a 1 : 1 by volume mixture of ethyl acetate and hexane, to give 2.94 g of the title compound as crystals, melting at 142 –143° C.

Optical rotation: $[\alpha]_D^{25}$ = +12.8° (c<1,CHCl$_3$).

Nuclear Magnetic Resonance Spectrum (CDCl$_3$) δ ppm:
- 0.6 –2.15 (18H, multiplet);
- 3.81 (3H, singlet);
- 3.6–4.2 (3H, broad singlet);
- 4.42 (1H, doublet, J=5 Hz);
- 4.53 (1H, doublet, J=5 Hz);
- 4.75 (1H, multiplet);
- 6.65–7.4 (12H, multiplet).;

11(b) (2S, 3S)-3-(2-Amino-5-phenoxyphenyl)thio-2-hydroxy-3-(4-methoxyphenyl)propionic acid 4.2 g of l-menthyl (2S, 3S)-3-(2-amino-5-phenoxyphenyl)thio-2-hydroxy-3-(4- methoxyphenyl)propionate [prepared as described in step (a) above] were suspended in 42 ml of methanol, and a solution of 0.89 g of caustic potash dissolved in 5 ml of water was added to the resulting suspension. The resulting mixture was then stirred under reflux for 1 hour. At the end of this time, the methanol was removed by evaporation under reduced pressure, and 60 ml of Water and 60 ml of diethyl ether were added to the residue. The resulting mixture was stirred, and the ethereal layer was then removed. Ethyl acetate was added to the aqueous layer. after which 14.5 ml of 1N aqueous hydrochloric acid were added to neutralize the mixture. The ethyl acetate layer was then separated and dried over anhydrous anhydrous magnesium sulfate. The solvent was removed by evaporation under reduced pressure, and the residual gum Was crystallized using diethyl ether and diisopropyl ether. The crystals obtained were collected by filtration to afford 2.05 g of the title compound. melting at 151–152° C.

Optical rotation: $[\alpha]_D^{25}$ = +319° (c=1, ethanol).

Nuclear Magnetic Resonance Spectrum (hexadeuterated dimethyl sulfoxide) δ ppm:
- 3.66 (3H, singlet);
- 4.27 (1H, doublet, J=5.5 Hz);
- 4.42 (1H, doublet, J=5.5 Hz);
- 6.5–7.4 (12H, multiplet).

11(c) (2S, 3S)-2,3-Dihydro-3-hydroxy-2-(4-methoxyphenyl)-8-phenoxy-1,5-benzothiazepin-4(5H)-one 1,5 ml of N-methylmorpholine was added, whilst ice-cooling, to a solution of 1.74 g of (2S, 3S)-3-(2-amino-5-phenoxyphenyl)thio-2-hydroxy-3-(4-methoxyphenyl)propionic acid [prepared as described in step (b)

above] and 1,5 g of diphenylphosphorylazide dissolved in 19 ml of dimethylformamide, and the mixture was stirred at room temperature for 16 hours. At the end of this time, ethyl acetate and water were added to the reaction mixture, and the resulting mixture was shaken to mix it thoroughly The ethyl acetate layer was then separated and dried over anhydrous magnesium sulfate, and the solvent was removed by evaporation under reduced pressure. The crystalline residue was collected by filtration using diethyl ether and diisopropyl ether to afford 0.90 g of the title compound melting at 181-183° C.

Optical rotation: $[\alpha]_D^{25} = +98.0°$ (c=1, dimethylformamide).

Nuclear Magnetic Resonance Spectrum (hexadeuterated dimethyl sulfoxide) δ ppm:
3.79 (3H, singlet);
3.80 (1H, doublet, J=7 Hz);
4.41 (1H, triplet, J=7 Hz);
5.01 (1H, doublet, J=7 Hz);
6.6-7.1 (12H, multiplet);
10.29 (1H, broad singlet).

10.46 g of the title compound were also prepared by suspending 11 9 g of (2S, 3S)-(2-amino-5-phenoxyphenyl)- thio-2-hydroxy-3-(4-methoxyphenyl)propionic acid [prepared as described in step (b)] in 500 ml of xylene, heating the mixture on an oil bath kept at 140° C., whilst stirring, then cooling the mixture and collecting the resulting precipitate by filtration.

11(d) (2S, 3S)-5-(2-Dimethylaminoethyl)-2,3-dihydro-3- hydroxy-2-(4-methoxyphenyl)-8-phenoxy-1,5-benzothiazepin-4(5H)-one A mixture of 0.50 g of (2S, 3S)-2,3-dihydro-3- hydroxy-2-(4-methoxyphenyl)-8-phenoxy-1,5-benzothiazepin-45H)-one [prepared as described in step (c) above], 0.38 g of 2-dimethylaminoethyl chloride hydrochloride, 0.52 g of potassium carbonate and 0.05 g of 4-dimethylaminopyridine and 0.05 g of 18-crown-6 dissolved in 30 ml of acetone was stirred whilst heating under reflux for 18 hours. At the end of this time, the acetone was removed by evaporation under reduced pressure, and the residue was dissolved in ethyl acetate and water. The ethyl acetate layer was separated, washed with water and dried over anhydrous anhydrous magnesium sulfate. The solvent Was then removed by evaporation under reduced pressure. The residue was purified by column chromatography using a 1 : 20 by volume mixture of methanol and methylene chloride as the eluent, to afford 0.53 g of the title compound as a syrup.

Nuclear Magnetic Resonance Spectrum (CDCl₃) δ ppm:
2.1-3.1 (3H, multiplet);
2.30 (6H, singlet);
3.3-4.0 (1H, multiplet);
3.80 (3H, singlet); 4.0-4.8 (2H, multiplet); 4.91 (1H, doublet, J=7 Hz); 6.8-7.7 (12H, multiplet).

EXAMPLE 12

(2S, 3S)-3-Acetoxy-5-(2-dimethylaminoethyl)-2,3-dihydro-2-(4-methoxyphenyl}-8-phenoxy-1,5-benzothiazepin-4(5H)-one 0.60 g of (2S, 3S)-5-(2-dimethylaminoethyl)-2,3- dihydro-3-hydroxy-2-(4-methoxyphenyl)-8-phenoxy-1,5-benzothiazepin-4(5H)-one (prepared as described in Example 11) was dissolved in 8 ml of pyridine and 5 ml of acetic anhydride, and the resulting mixture was left to stand at room temperature for 16 hours. At the end of this time, the reaction mixture was concentrated by evaporation under reduced pressure, and the pyridine in the residue was evaporated by azeotropy with toluene. The residue was purified by silica gel column chromatography using a 1 : 20 by volume mixture of methanol and methylene chloride as the eluent, to afford the title compound as a gum. This was dissolved in 5 ml of ethyl acetate, and 1 ml of a 4N solution of hydrogen chloride in dioxane was added to the resulting solution. which was then concentrated by evaporation under reduced pressure. A small amount of water was added to the residue and, while the resulting mixture was stirred, fine crystalline powders separated. These were collected by filtration and washed with water and with diisopropyl ether, to give 0.55 g of the hydrochloride of the title compound melting at 121-123° C. (softening).

Optical rotation: $[\alpha]_D^{25} = +84.4°$ (c=1, dimethylformamide).

Nuclear Magnetic Resonance Spectrum (hexadeuterated dimethyl sulfoxide) δ ppm:
1.83 (3H, singlet);
2.79 (6H, singlet);
3.0-3.6 (2H, multiplet); 3.76 (3H, singlet); 4.0-4.6 (2H, multiplet); 5.03 (1H, doublet, J=7 Hz); 5.17 (1H doublet, J=7 Hz); 6.8-7.8 (12H, multiplet).

The fumarate and L-tartarate of the title compound were also prepared by concentrating a mixture of a molar equivalent each of the title compound and either fumaric acid or tartaric acid in methanol under reduced pressure and then triturating the product with a mixture of ethyl acetate and a small amount of diethyl ether.

Fumarate:

m.p.: softening near 95° C.

Optical rotation: $[\alpha]_D^{25} = +68.0°$ (c=1, dimethylformamide).

Nuclear Magnetic Resonance Spectrum (hexadeuterated dimethyl sulfoxide) δ ppm:
1.82 (3H, singlet);
2.34 (6H, singlet);
2.2-2.9 (2H, multiplet);
3.76 (3H singlet);
3.5-4.6 (2H, multiplet);
5.09 (2H, singlet);
6.60 (2H, singlet);
6 8-7.8 (12H, multiplet).

L-Tartarate m.p.: 146-148° C.

Optical rotation: $[\alpha]_D^{25} + 66.6°$ (c=1, dimethylformamide).

Nuclear Magnetic Resonance Spectrum (hexadeuterated dimethyl sulfoxide) δ ppm:
1.82 (3H, singlet);
2.38 (6H, singlet);
2.3-3.1 (2H, multiplet);
3.83 (3H, singlet);
3 4-4.4 (2H, multiplet);
4.15 (2H, singlet);
5.06 (2H, AB-quartet, Δδ=0.13 ppm, J=7 Hz);
6.8-7.8 (12H, multiplet).

EXAMPLE 13

(2S, 3S)-5-(2-Dimethylaminoethyl)-8-(4-fluorophenoxy)-2,3-dihydro-3-hydroxy-2-(4-methoxyphenyl)-1,5-benzothiazepin-4(5H)-one

13(a) l-Menthyl (2S, 3S)-3-[2-amino-5-(4-fluorophenoxy)phenyl]thio-2-hydroxy-3-(4-methoxyphenyl)propionate Following a procedure similar to that described in Example 11(a), 21 g of l-menthyl trans-2,3-epoxy-3-(4-methoxyphenyl)propionate (prepared as described in Preparation 5) and 14.1 g of 2-amino-5-(4-fluorophenoxy)benzenethiol (prepared as described in Preparation 8) were reacted in 100 ml of toluene to give 13.8 g of the title compound as a crystalline product, melting at 127–129° C. Optical rotation: $[\alpha]_D^{25} = +7.0°$ (c=1, CHCl₃).

Nuclear Magnetic Resonance Spectrum (CDCl₃) δ ppm:
0.6–2.2 (18H, multiplet); 3.72 (3H, singlet); 4.10 (3H, broad singlet); 4.40 (1H, doublet, J=5 Hz); 4.52 (1H, doublet, J=5 Hz); 4.72 (1H, multiplet); 6.5–7.3 (11H, multiplet).

13(b) (2S, 3S)-3-[2-Amino-5-(4-fluorophenoxy)phenyl]thio-2-hydroxy-3-(4-methoxyphenyl)propionic acid Following a procedure similar to that described in Example 11(b), 13.3 g of l-menthyl (2S, 3S)-3-[2-amino-5-(4-fluorophenoxy)phenyl]thio-2-hydroxy-3-(4-methoxyphenyl)propionate [prepared as described in step (a) above] were hydrolyzed to give 5.8 g of the title compound as crystals, melting at 167° C.

Optical rotation: $[\alpha]_D^{25} = +346°$ c=1, dimethylformamide).

Nuclear Magnetic Resonance Spectrum (hexadeuterated dimethyl sulfoxide) δ ppm:
3.70 (3H, singlet);
4.30 (1H, doublet, J=5.5 Hz);
4.42 (1H, doublet, J=5.5 Hz);
6.45–7.3 (11H, multiplet).

13(c) (2S, 3S)-8-(4-Fluorophenoxy)-2,3-dihydro-3-hydroxy-2-(4-methoxyphenyl)-1,5-benzothiazepin-4(5H)-one Following a procedure similar to that described in Example 11(c), 5.45 g of (2S, 3S)-3-[2-amino-5-(4-fluorophenoxy)phenyl]thio-2-hydroxy-3-(4-methoxyphenyl)propionic acid [prepared as described in step (b) above] were subjected to ring closure to give 3.69 g of the title compound as crystals, melting at 198–200° C.

Optical rotation: $[\alpha]_D^{25} = +87.6°$ (c=1, dimethylformamide).

Nuclear Magnetic Resonance Spectrum (hexadeuterated dimethyl sulfoxide) δ ppm:
3.75 (3H, singlet);
4.34 (1H, triplet, J=7 Hz);
4.61 (1H, doublet, J=7 Hz);
5.05 (1H, doublet, J=7 Hz);
6.8–7.45 (11H, multiplet);
10.26 (1H, broad singlet).

(d) (2S, 3S)-5-(2-Dimethylaminoethyl)-8-(4-fluorophenoxy)-2,3-dihydro-3-hydroxy-2-(4-methoxyphenyl)-1,5-benZothiazepin-4(5H)-one Following a procedure similar to that described in Example 11(d), 3,4 g of (2S, 3S)-2,3-dihydro-8-(4-fluorophenoxy)-3-hydroxy-2-(4-methoxyphenyl)-1,5-benzothiazepin-4(5H)-one [prepared as described in step (c) above] were alkylated with dimethylaminoethyl chloride hydrochloride to give 3.63 g of the title compound as a syrup.

Nuclear Magnetic Resonance Spectrum (CDCl₃) δ ppm:
2.26 (6H, singlet);
2.2–3.0 (3H, multiplet);
3.78 (3H, singlet);
3.4–3.9 (1H, multiplet);
4.2–4.55 (2H, multiplet);
4.88 (1H, doublet, J=7 Hz);
6.8–7.55 (11H, multiplet).

EXAMPLE 14

(2S, 3S)-3-Acetoxy-5-(2-dimethylaminoethyl)-8-(4-fluorophenoxy)-2,3-dihydro-2-(4-methoxyphenyl)-1,5-benzothiazpin-4(5H)-one Following a procedure similar to that described in Example 12, 3.63 g of (2S, 3S)-5-(2-dimethylaminoethyl)-8-(4-fluorophenoxy)-2,3-dihydro-3-hydroxy-2-(4-methoxyphenyl)-1,5-benZothiazepin-4(5H)-one (prepared as described in Example 13) were acetylated to give 3.8 g of the title compound as a caramel-like substance.

Nuclear Magnetic Resonance Spectrum (CDCl₃) δ ppm:
1.89 (3H, singlet);
2.29 (6H, singlet);
2.1–3.0 (2H, multiplet);
3.5–3.9 (1H, multiplet);
3.80 (3H singlet);
4.1–4.6 (1H, multiplet);
4.97 (1H, doublet J=7 Hz);
5.20 (1H, doublet J=7 Hz);
6.75–7.6 (11H, multiplet).

3.8 g of this compound was dissolved in ethyl acetate, and 8 ml of a 4N solution of hydrogen chloride in dioxane was added to the solution. The mixture was then concentrated by evaporation under reduced pressure. The concentrate was then triturated in diisopropyl ether to give 3.8 g of the hydrochloride of the title compound as an amorphous powder.

Optical rotation: $[\alpha]_D^{25} = +81.2°$ (c=1, dimethylformamide). Nuclear Magnetic Resonance Spectrum (hexadeuterated dimethyl sulfoxide) δ ppm:
1.84 (3H, singlet);
2.81 (6H, singlet);
3.05–3.2 (1H, multiplet);
3.4–3.55 (1H, multiplet);
3.77 (3H, singlet);
4.0–4.1 (1H, multiplet);
4.4–4.5 (1H, multiplet);
5.05 (1H, doublet J=8 Hz);
5.17 (1H, doublet, J=8 Hz);
6.9–7.7 (11H, multiplet).

Following a procedure similar to that described in Example 12 but employing a mixture of diethyl ether and diisopropyl ether for trituration the fumarate of the title compound was prepared.

m.p.: softening near 105° C.

Optical rotation: $[\alpha]_D^{25} = +60.3°$ (c=1, dimethylformamide).

Nuclear Magnetic Resonance Spectrum (hexadeuterated dimethyl sulfoxide+CDCl₃) δ ppm:

1.85 (3H, singlet);
2.37 (6H, singlet);
2.2–3.0 (2H, multiplet);
3.77 (3H, singlet); 3.3–4.5 (2H, multiplet);
5.08 (2H, singlet);
6.60 (2H, singlet);
6.8–7.75 (11H, multiplet).

EXAMPLE 15

(2S, 3S)-5-(2-Dimethylaminoethyl)-2-(3-fluoro-4-methoxyphenyl)-2,3-dihydro-3-hydroxy-8-phenoxy-1,5-benzothiazepin-4(5H)-one 15(a) l-Menthyl (2S, 3S)-3-(2-amino-5-phenoxyphenyl)-thio-3-(3-fluoro-4-methoxyphenyl)-2-hydroxypropionate Following a procedure similar to that described in Example 11(a), 28.3 g of l-menthyl trans-2,3-epoxy-3-(3-fluoro-4-methoxyphenyl)propionate (prepared as described in Preparation 6) and 17.2 g of 2-amino-5-phenoxybenzenethiol (prepared as described in Preparation 2) were reacted in 200 ml of toluene, after which the reaction mixture was concentrated by evaporation under reduced pressure. The viscous liquid obtained as a residue was subjected to column chromatography through silica gel using methylene chloride as the eluent to afford 5.8 g of a solid containing the title compound. Furthermore, 13.6 g of the l-menthyl trans-2,3-epoxy-3-(3-fluoro-4-methoxyphenyl)propionate starting material were recovered. The crudely purified product (5.8 g) was recrystallized from diisopropyl ether to afford 4 g of the title compound, melting at 138–140° C.

Optical rotation: $[\alpha]_D^{25} = +3.9°$ (c=1, CHCl$_3$).

Nuclear Magnetic Resonance Spectrum (CDCl$_3$) δ ppm:
0.6–2.2 (18H, multiplet);
3.80 (3H, singlet);
4.20 (3H, broad singlet);
4.39 (1H, doublet, J=5 Hz);
4.51 (1H, doublet, J=5 Hz);
4.5–5.1 (1H, multiplet);
6.5–7.4 (11H, multiplet).

15(b) (2S, 3S)-3-(2-Amino-5-phenoxyphenyl)thio-3-(3-fluoro-4-methoxyphenyl)-2-hydroxypropionic acid Following a procedure similar to that described in Example 11(b), 4 g of l-menthyl (2S, 3S)-3-(2-amino-5-phenoxyphenyl)thio-3-(3-fluoro-4-methoxyphenyl)-2-hydroxypropionate [prepared as described in step (a) above] was hydrolyzed to give 1,58 g of a yellow amorphous solid. This compound was used for the next reaction without further purification.

15(c) (2S, 3S)-2-(3-Fluoro-4-methoxyphenyl)-2 3-dihydro-3-hydroxy-8-phenoxy-1,5-benzothiazepin-4(5H)-one Following a procedure similar to that described in Example 11(c), 1.58 g of (2S, 3S)-3-(2-amino-5-phenoxy- phenyl)thio-3-(3-fluoro-4-methoxyphenyl)-2-hydroxypropionic acid [prepared as described in step (b) above] was subjected to ring closure to afford 0.98 g of the title compound as crystals, melting at 209–210° C.

Optical rotation: $[\alpha]_D^{25} = +84.8°$ (c=1, dimethylformamide).

Nuclear Magnetic Resonance Spectrum (hexadeuterated dimethyl sulfoxide+tetradeuterated methanol) δ ppm:

3.85 (3H, singlet);
4.44 (1H, doublet, J=7 Hz);
5.09 (1H, doublet, J=7 Hz);
6.8–7.7 (11H, multiplet).

15(d) (2S, 3S)-5-(2-Dimethylaminoethyl)-2-(3-fluoro-4-methoxyphenvl)-2,3-dihydro-3-hydroxy-8-phenoxy-1,5-benzothiazepin-4(5H)-one Following a procedure similar to that described in Example 11(d), 400 mg of (2S, 3S)-2-(3-fluoro-4-methoxyphenyl)-2,3-dihydro-3-hydroxy- 8-phenoxy-1,5-benzothiazepin-4(5H)-one [prepared as described in step (c) aboVe] were alkylated with 2-dimethylaminoethyl chloride hydrochloride to afford 500 mg of the title compound as a syrup.

Nuclear Magnetic Resonance Spectrum (CDCl$_3$) δ ppm:
2.28 (6H, singlet);
2.1–3.0 (2H, multiplet);
2.99 (1H, broad singlet);
3.2–4.0 (1H, multiplet);
3.83 (3H, singlet);
4.2–4.9 (1H, multiplet);
4.30 (1H, doublet, J=7 Hz);
6.6–7.7 (1H, multiplet).

EXAMPLE 16

(2S, 3S)-3-Acetoxy-5-(2-dimethylaminoethyl)-2-(3-fluoro-4-methoxyphenvl)-2,3-dihydro-8-phenoxy-1,5-benzothiazepin-4(5H)-one Following a procedure similar to that described in Example 12, 500 mg of (2S, 3S)-5-(2-dimethylaminoethyl)-2-(3-fluoro-4-methoxyphenyl)-2,3-dihydro-3-hydroxy-8-phenoxy-1,5-benzothiazepin-4(5E,uns/H/)-one (prepared as described in Example 15) was acetylated, purified by column chromatography and then crystallized from ethyl acetate to afford 424.8 mg of the title compound as colorless crystals, melting at 167–168° C.

Optical rotation: $[\alpha]_D^{25} = +75.3°$ (c=1, dimethylformamide).

Nuclear Magnetic Resonance Spectrum (hexadeuterated dimethyl sulfoxide) δ ppm:
1.92 (3H, singlet);
2.30 (6H, singlet);
2.1–3.0 (2H, multiplet);
3.4–3.9 (1H, multiplet);
3.87 (3H, singlet);
4.2–4.8 (1H, multiplet);
4.94 (1H, doublet J=7 Hz);
5.10 (1H, doublet. J=7 Hz);
6.7–7.7 (1H, multiplet).

0.22 ml of a 4N solution of hydrogen chloride in dioxane was added to a solution of 389.9 mg of the title compound dissolved in methanol and the resulting solution was concentrated by evaporation under reduced pressure. The resulting concentrate was then triturated in diethyl ether to afford 354.1 mg of the hydrochloride of the title compound as an amorphous powder, melting at 117–125° C.

Optical rotation: $[\alpha]_D^{25} = +81.1°$ (c=1, dimethylformamide).

Nuclear Magnetic Resonance Spectrum (hexadeuterated dimethyl sulfoxide) δ ppm:
1.85 (3H, singlet);
2.80 (6H, singlet);

3.0-3.8 (2H, multiplet);
3.9-4.7 (2H, multiplet);
5.02 (1H, doublet J=7 Hz);
5.29 (1H, doublet, J=7 Hz);
6.8-7.9 (11H, multiplet).

Following a procedure similar to that described in Example 12, the fumarate of the title compound melting at 156–158.5° C., was obtained by crystallization from a mixture of ethyl acetate and diethyl ether and collecting the salt by filtration.

Optical rotation: $[\alpha]_D^{25} = +64.1°$ (c=1, dimethylformamide).

Nuclear Magnetic Resonance Spectrum (hexadeuterated dimethyl sulfoxide+CDCl$_3$) δ ppm:
  1.95 (3H, singlet);
  2.32 (6H, singlet);
  2.2-3.0 (2H, multiplet);
  3.85 (3H, singlet);
  3.5-4.7 (2H, multiplet);
  5.10 (2H, singlet);
  6.62 (2H, singlet);
  7.0-7.8 (11H, multiplet).

EXAMPLE 17

(2S, 3S)-8-Benzyl-5-(2-dimethylaminoethyl)-2,3-dihydro-3-hydroxy-2-(4-methoxyphenyl)-1,5-benzothiazepin-4(5H)-one

17(a) l-Menthyl (2S, 3S)-3-(2-amino-5-benzylphenyl)-thio-2-hydroxy-3-(4-methoxyphenyl)propionate 32.5 g of l-menthyl trans-2,3-epoxy-3-(4-methoxyphenyl)propionate (prepared as described in Preparation 5) and 21.1 % of 2-amino-5-benzylbenzenethiol were stirred in 320 ml of toluene at 90° C. for 16 hours. At the end of this time, the reaction mixture was cooled, and the crystals which had precipitated were collected by filtration and washed with toluene and with hexane, in that order to give 15.9 g of the title compound.

The filtrate was concentrated by evaporation under reduced pressure, and the residue was subjected to silica gel column chromatography using a 7 : 12 : 1 by volume mixture of hexane, 1,2-dichloroethane and ethyl acetate as the eluent. The fractions containing the title compound were concentrated by evaporation under reduced pressure. The resulting crystals were collected by filtration with diethyl ether to afford a further 2.9 g of the title compound melting at 157–159° C.

Optical rotation: $[\alpha]_D^{25} = +179°$ (c=1, CHCl$_3$).

Nuclear Magnetic Resonance Spectrum (CDCl$_3$+a small amount of D$_2$O), δ ppm:
  0.6-2.1 (18H, multiplet);
  3.69 (2H, singlet);
  3.76 (3H, singlet);
  4.34 (1H, doublet, J=5 Hz);
  4.48 (1H, doublet, J=5 Hz);
  4.80 (1H, multiplet);
  6.55-7.3 (12H, multiplet).

17(b) (2S, 3S)-3-(2-Amino-5-benzylphenyl)thio-2-hydroxy-3-(4-methoxyphenyl)propionic acid 17 15 g of l-menthyl (2S, 3S)-3-(2-amino-5-benzylphenyl)thio-2-hydroxy-3-(4-methoxyphenyl)propionate [prepared as described in step (a) above] were suspended in 65 ml of ethanol, and a solution of 6.2 g of caustic potash dissolved in 20 ml of water were added to the suspension. The mixture was then stirred at 60° C. for 2 hours. At the end of this time, the ethanol was removed by evaporation under reduced pressure, and diethyl ether and water were added to the residue. The resulting mixture was stirred, and then the ethereal layer was removed. Ethyl acetate was added to the aqueous layer, and then sufficient 3N aqueous hydrochloric acid was added thereto to adjust pH to a value of 3. The ethyl acetate layer was then separated and dried over anhydrous anhydrous magnesium sulfate, and the solvent was removed by evaporation under reduced pressure. The syrup-like residue was left to stand and the crystals which formed were collected by filtration using diethyl ether to afford 7.64 g of the title compound, melting at 155–158° C.

Optical rotation: $[\alpha]_D^{25} = +304°$ (c=1, dimethylformamide).

Nuclear Magnetic Resonance Spectrum (hexadeuterated dimethyl sulfoxide) δ ppm:
  3.60 (2H, singlet);
  3.72 (3H, singlet);
  4.31 (AB quartet, Δδ=0.10 ppm, J=5 Hz);
  6.55-7.3 (12H, multiplet).

17(c) (2S, 3S)-8-benzyl-2,3-dihydro-3-hydroxy-2-(4-methoxyphenyl)-1,5-benzothiazepin-4(5H)-one A solution of 6.71 g of (2S, 3S)-3-(2-amino-5-benzylphenyl)thio-2-hydroxy-3-(4-methoxyphenyl)propionic acid [prepared as described in step (b) above] dissolved in 400 ml of xylene was heated under reflux for 8 hours whilst stirring. At the end of this time, the mixture was cooled to room temperature and the crystals which precipitated were collected by filtration and washed with xylene and hexane to give 5.8 g of the title compound, melting at 200–202° C. (with decomposition).

Optical rotation: $[\alpha]_D^{25} = +110°$ (c=1, dimethylformamide).

Nuclear Magnetic Resonance Spectrum (CDCl$_3$), δ ppm:
  2.50 (1H, broad singlet);
  3.76 (3H, singlet);
  3.97 (2H, singlet);
  4.46 (1H, doublet, J=6.6 Hz); 5.05 (1H, doublet, J=6.5 Hz); 6.77-7.57 (12H, multiplet); 8.3 (1H, broad singlet).

17(d) (2S, 3S)-8-Benzyl-2 3-dihydro-5-(2-dimethylaminoethyl)-3-hydroxy-2-(4-methoxyphenyl)-1,5-benzothiazepin-4(5H)-one A solution of a mixture of 5.3 g of (2S, 3S)-8- benzyl-2,3-dihydro-3-hydroxy-2-(4-methoxyphenyl)-1,5-benzoththiaepin-4(5H)-one [prepared as described in step (c) above], 2.34 g of 2-dimethylaminoethyl chloride hydrochloride, 5.6 9 of potassium carbonate and 0.17 g of 4-dimethylaminopyridine dissolved in 250 ml of acetone was stirred under reflux for 20 hours. At the end of this time the acetone was removed by evaporation under reduced pressure, and the residue was dissolved in ethyl acetate and water. The ethyl acetate layer was separated and washed with water, after which it was dried over anhydrous magnesium sulfate. The solvent was then removed by evaporation under reduced pressure. The residue was purified by silica gel column chromatography using a 1 : 20 by volume mixture of methanol and methylene chloride as the eluent, to give 5.93 g of the title compound as a gum.

Optical rotation: $[\alpha]_D^{25} = +110°$ (c=1, dimethylformamide).

Nuclear Magnetic Resonance Spectrum (CDCl$_3$), δ ppm:
2.24 (6H, singlet);
2.3–3.1 (3H, multiplet);
3.4–4.0 (1H, multiplet);
3.76 (3H, singlet);
3.95 (2H, singlet);
4.2–4.7 (2H, multiplet);
4.86 (1H, d, J=6.5 Hz); 6.8–7.6 (12H, multiplet).

EXAMPLE 18

(2S, 3S)-3-Acetoxy-8-benzyl-2,3-dihydro-5-(2-dimethyl-aminoethyl)-2-(4-methoxyphenyl)-1,5-benzothiazepin-4(5H)-one 5.92 g of (2S, 3S)-8-benzyl-2,3-dihydro-5-(2-methylaminoethyl)-3-hydroxy-2-(4-methoxyphenyl)-1,5-benzothiazepin-4(5H)-one (prepared as described in Example 17) were dissolved in 12 ml of pyridine and 6 ml of anhydrous acetic anhydride and the solution was left to stand at room temperature for 16 hours. At the end of this time, 10 ml of ethanol were added to the reaction mixture, and after the mixture had been left to stand for 20 minutes, the solvent was removed by evaporation under reduced pressure, and the pyridine and acetic acid in the residue were evaporated by azeotropic distillation with toluene. The residue was purified by silica gel column chromatography using a 1 : 20 by volume mixture of methanol and methylene chloride as the eluent, to afford 6.02 g of the title compound as a gum.

Optical rotation: $[\alpha]_D = +84°$ (c=1, dimethylformamide).

Nuclear Magnetic Resonance Spectrum (CDCl$_3$), δ ppm:
1.87 (3H, singlet);
2.26 (6H, singlet);
2.2–3.0 (2H, multiplet);
3.4–4.7 (2H, multiplet);
3.80 (3H, singlet);
3.98 (2H, singlet);
4.97 (1H, doublet, J=6.5 Hz);
5.18 (1H, doublet, J=6.5 Hz);
6.8–7.6 (12H, multiplet).

4.05 g of the title compound were dissolved in 20 ml of ethyl acetate, and 6 ml of a 4N solution of hydrogen chloride in ethyl acetate was added thereto. The mixture was then concentrated by evaporation under reduced pressure, after which the residue was triturated in diethyl ether, collected by filtration and dried to give 4.35 g of the hydrochloride of the title compound. melting at 115–120° C. (softening).

Optical rotation: $[\alpha]_D^{25} = +81°$ (c=1, dimethylformamide).

Nuclear Magnetic Resonance Spectrum (hexadeuterated dimethyl sulfoxide), δ ppm:
1.82 (3H, singlet);
2.77 (3H, broad singlet);
2.82 (3H, broad singlet);
3.05–3.2 (1H, multiplet);
3.3–3.5 (1H, multiplet);
3.77 (3H, singlet);
4.01 (2H, singlet);
4.0–4.15 (1H, multiplet);
4.3–4.5 (1H, multiplet);
4.98 (1H, doublet, J=7 Hz);
5.14 (1H, doublet, J=7 Hz);
6.85–7.65 (12H, multiplet).

The L-tartarate of the title compound was prepared by concentrating a mixture of a molar equivalent each of the title compound and L-tartaric acid in methanol and crystallizing the residual gum from ethyl acetate.
m.p.: softening near 95° C.

Optical rotation: $[\alpha]_D^{25} = +63.2°$ (c=1, dimethylformamide).

Nuclear Magnetic Resonance Spectrum (hexadeuterated dimethyl sulfoxide) δ ppm:
1.80 (3H, singlet);
2.37 (6H, singlet);
2.3–3.2 (2H, multiplet);
3.5–4.6 (2H, multiplet);
3.76 (3H, singlet);
3.99 (2H, singlet);
4.20 (2H, singlet);
4.96 (1H, doublet, J=6.5 Hz);
5.08 (1H, doublet, J=6.5 Hz);
6.40 (4H, broad singlet);
6.90 (2H, doublet, J=9 Hz);
7.3–7.7 (10H, multiplet).

EXAMPLE 19

(2S, 3S)-5-(2-Dimethylaminoethyl)-2,3-dihydro-3-hydroxy-2-(4-methoxyphenyl)-8-(2-thienylmethyl)-1,5-benzothiazepin-4(5H)-one 19(a) l-Menthyl (2S, 3S)-3-[2-amino-5-(2-thienyl-methyl)phenyl]thio-2-hydroxy-3-(4-methoxyphenyl)propionate Following a procedure similar to that described in Example 17(a), 14.5 g of l-menthyl trans-2,3-epoxy-3-(4-methoxyphenyl)propionate (prepared as described in Preparation 5) and 9.65 g of 2-amino-5-(2-thienyl)methylbenzenethiol were reacted in 150 ml of toluene to give 1.84 g of the title compound as crystals, melting at 147–148° C.

Optical rotation: $[\alpha]_D^{25} = +1.9°$ (c=1, CHCl$_3$).

Nuclear Magnetic Resonance Spectrum (CDCl$_3$), δ ppm:
0.6–2.2 (18H, multiplet); 3.75 (3H, singlet);
3.86 (2H, singlet);
3.90 (3H, broad singlet);
4.36 (1H, doublet, J=5 Hz);
4.52 (1H, doublet, J=5 Hz);
4.75 (1H multiplet);
6.55–7.3 (10H, multiplet).

19(b)(2S, 3S)-3-[2-Amino-5-(2-thienylmethyl)phenyl]-thio-2-hydroxy-3-(4-methoxyphenyl)propionic acid Following a procedure similar to that described in Example 17(b), 1.82 g of l-menthyl (2S, 3S)-3-[2-amino-5-(2-thienylmethyl)phenyl]thio-2-hydroxy-3-(4-methoxyphenyl)propionate [prepared as described in step (a) above] was hydrolyzed to give 0.59 g of the title compound as crystals. melting at 149–153.5° C.

Optical rotation: $[\alpha]_D^{25} = +281°$ (c=1, dimethylformamide).

Nuclear Magnetic Resonance Spectrum (hexadeuterated dimethyl sulfoxide), δ ppm:
3.72 (3H, singlet);
3.79 (2H, singlet);
4.30 (2H, broad singlet);
6.55–7.3 (10H, multiplet).

19(c) (2S, 3S)-2,3-Dihydro-3-hydroxy-2-(4-methoxyphenyl)-8-(2-thienylmethyl)-1,5-benzothiazepin-4(5H)-one Following a procedure similar to that described in Example 17(c), 537 mg of (2S, 3S)-3-[2-amino-5-(2-thienylmethyl)phenyl]thio-2-hydroxy-3-(4-methoxyphenyl)propionic acid [prepared as described in step (b) above] were subjected to ring closure to give 411 ml of the title compound as crystals, melting at 204-208° C. (with decomposition).

Optical rotation: $[\alpha]_D^{25} = +103°$ (c=1, dimethylformamide).

Nuclear Magnetic Resonance Spectrum (hexadeuterated dimethyl sulfoxide) δ ppm:
3.76 (3H, singlet);
4.16 (2H, singlet);
4.30 (1H, triplet, J=7 Hz);
4.61 (1H, doublet, J=7 Hz);
5.05 (1H, doublet, J=7 Hz);
6.85-7.6 (10H multiplet);
10.29 (1H, broad singlet).

19(d) (2S, 3S)-5-(2-Dimethylaminoethyl)-2,3-dihydro-3-hydroxy-2-(4-methoxyphenyl)-8-(2-thienylmethyl)-1,5-benzothiazepin-4(5H)-one Following a procedure similar to that described in Example 17(d), 370 mg of (2S, 3S)-2,3-dihydro-3-hydroxy- 2-(4-methoxyphenyl)-8-(2-thienylmethyl)-1,5-benzothiazepin-(5H)-one [prepared as described in step (c) above] were alkylated with 161 mg of 2-dimethylaminoethyl chloride hydrochloride to give 441 mg of the title compound as a foamy solid.

Optical rotation: $[\alpha]_D^{25} = +113°$ (c=1, CHCl₃).

Nuclear Magnetic Resonance Spectrum (CDCl₃), δ ppm:
2.27 (6H, singlet);
2.15-3.0 (3H, multiplet);
3.79 (3H, singlet);
3.4-3.9 (1H, multiplet);
4.14 (2H, singlet);
4.1-4.7 (2H, multiplet); 4.85 (1H, doublet, J=7 Hz);
6.75-7.6 (10H, multiplet).

EXAMPLE 20

(2S, 3S)-3-Acetoxy-5-(2-dimethylaminoethyl)-2,3-dihydro-2-(4-Methoxyphenyl)-8-(2-thienylmethyl)-1,5-benzothiazepin-4(5H)-one Following a procedure similar to that described in Example 18, 436 mg of (2S, 3S)-5-(2-dimethylaminoethyl)- 2,3-dihydro-3-hydroxy-2-(4-methoxyphenyl)-8-(2-thienyl- methyl)-1,5-benzothiazepin-4(5H)-one (prepared as described in Example 19) Were acetylated to give 468 mg of the title compound as a caramel-like substance.

Optical rotation: $[\alpha]_D^{25} = +67°$ (c=1, CDCl₃).

Nuclear Magnetic Resonance Spectrum (CDCl₃), δ ppm:
1.86 (3H, singlet);
2.25 (6H, singlet);
2.1-3.1 (2H, multiplet);
3.79 (3H, singlet);
3.4-4.0 (1H, multiplet);
4.1-4.7 (1H, multiplet);
4.16 (2H, singlet);
4.97 (1H doublet, J=7 Hz);
5.16 (1H, doublet, J=7 Hz);
6.8-7.6 (10H, multiplet).

468 mg of (2S, 3S)-3-acetoxy-5-(2-dimethylaminoethyl)-2,3-dihydro-2-(4-methoxyphenyl)-8-(2-thienylmethyl)-1,5-benzothiazepin-4(5H)-one (prepared as described above) were subjected to the same treatment as described in Example 18 using a solution of hydrogen chloride in ethyl acetate to give 492 mg of the hydrochloride of the title compound as an amorphous powder.

Optical rotation; $[\alpha]_D^{25} = +76°$ (c=1, dimethylformamide).

Nuclear Magnetic Resonance Spectrum (hexadeuterated dimethyl sulfoxide), δ ppm:
1.80 (3H, singlet);
2.78 (6H, singlet);
3.0-3.9 (2H, multiplet);
3.76 (3H, singlet);
4.22 (2H, singlet);
4.0-4.5 (2H, multiplet);
4.97 (1H, doublet, J=7 Hz);
5.14 (1H, doublet, J=7 Hz);
6.85-7.8 (10H, multiplet).

EXAMPLE 21

(±)-cis-5-(2-Dimethylaminoethyl)-8-(4-fluorophenoxy)-2,3-dihydro-3-hydroxy-2-(4-methoxyphenyl)-1,5-benzothiazepin-4(5H)-one

21(a) Ethyl 3-[2-amino-5-(4-fluorophenoxy)phenyl]thio-2-hydroxy-3-(4-methoxyphenyl)propionate A procedure similar to that described in Example 1(a) was repeated, except that 8.22 g of 2-amino-5-(4-fluorophenoxy)benzenethiol and 6.6 g of (±)-ethyl 3-(4-methoxyphenyl)glycidate were used, to afford 8.7 g of the title compound as a syrup.

Nuclear Magnetic Resonance Spectrum (CDCl₃) δ ppm:
1.19 (3H, triplet, J=7Hz);
3.73 (3H, singlet);
3.9-4.6 (7H, multiplet);
6.55-7.4 (11H, multiplet).

21(b) 3-[2-Amino-5-(4-fluorophenoxy)phenyl]thio-2-hydroxy-3-(4-methoxyphenyl)propionic acid A procedure similar to that described in Example 1(b) was repeated, except that 8.7 g of ethyl 3-[2-amino-5-(4-fluorophenoxy)phenyl]thio-2-hydroxy-3- (4-methoxyphenyl)propionate [prepared as described in step (a) above] were employed, to afford 5.12 g of the title compound, melting at 190-193° C.

Nuclear Magnetic Resonance Spectrum (hexadeuterated dimethyl sulfoxide) δ ppm:
3.70 (3H, singlet);
4.36 (2H, AB-guartet, Δδ=0.9 ppm, J=6Hz);
6.45-7.25 (11H, multiplet).

21(c) (±)-cis-8-(4-Fluorophenoxy)-2,3-dihydro-3-hydroxy-2-(4-methoxyphenyl)-1,5-benzothiazepin-4(5H)-one A procedure similar to that described in Example 1(c) was repeated, except that 4.82 g of 3-[2-amino-5- (4-fluorophenoxy)phenyl]thio-2-hydroxy-3-(4-methoxyphenyl)propionic acid [prepared as described in step (b) above] were employed, to afford 3.05 g of the title compound as crystals, melting at 246-248° C.

Nuclear Magnetic Resonance Spectrum (hexadeuterated dimethyl sulfoxide) δ ppm:
3.75 (3H, singlet);
4.34 (1H, triplet, J=7 Hz);
4.62 (1H, doublet, J=7 Hz);
5.05 (1H, doublet, J=7 Hz);
6.8–7.45 (11H, multiplet);
10.26 (1H, singlet).

21(d) (±)-cis-5-(2-Dimethylaminoethyl)-8-(4-fluorophenoxy)-2,3-dihydro-3-hydroxy-2-(4-methoxyphenyl)-1,5-benzothiazepin-4(5H)-one A procedure similar to that described in Example 1(d) was repeated, except that 500 mg of (±)-cis-8-(4-fluorophenoxy)-2,3-dihydro-3-hydroxy-2 (4-methoxyphenyl)-1,5-benzothiazepin-4(5H)-one [prepared as described in step (c) above] were employed, to afford 584 mg of the title compound as an amorphous solid.

Nuclear Magnetic Resonance Spectrum (CDCl$_3$) δ ppm:
2.26 (6H, singlet);
2.1–3.0 (3H, multiplet);
3.4–3.95 (1H, multiplet);
3.78 (3H, singlet);
4.2–4.7 (2H, multiplet);
4.88 (1H, doublet, J=7 Hz);
6.8–7.5 (11H, multiplet).

EXAMPLE 22

(±)-cis-3-Acetoxy-5-(2-dimethylaminoethyl)-8-(4-fluorophenoxy)-2,3-dihydro-2-(4-methoxyphenyl)-1,5-benzothiazepin-4(5H)-one A procedure similar to that described in Example 2 was repeated, except that 584 mg of (±)-cis-5-(2- dimethylaminoethyl)-8-(4-fluorophenoxy)-2,3-dihydro-3-hydroxy-2-(4-methoxyphenyl)-1,5-benzothiazepin-4(5H)-one (prepared as described in Example 21) were employed, to afford 590 mg of the hydrochloride of the title compound as an amorphous solid.

Nuclear Magnetic Resonance Spectrum (hexadeuterated dimethyl sulfoxide) δ ppm:
1.84 (3H, singlet);
2.80 (6H, singlet);
3.08–3.27 (1H, multiplet);
3.30–3.5 (1H, multiplet);
3.77 (3H, singlet);
4.03–4.10 (1H, multiplet);
4.38–4.49 (1H, multiplet);
5.05 (1H, doublet, J=7 Hz);
5.17 (1H, doublet, J=7 Hz);
6.9–7.7 (11H, multiplet);
10.59 (1H, singlet).

EXAMPLE 23

(±)-cis-5-(2-Dimethylaminoethyl)-2-(3-fluoro-4-methoxyphenyl)-8-(4-fluorophenoxy)-2,3-dihydro-3-hydroxy-1,5-benzothiazepin-4(5H)-one 23(a) Ethyl 3-[2-amino-5-(4-fluorophenoxy)phenyl]thio-3-(3-fluoro-4-methoxyphenyl]-2-hydroxypropionate A procedure similar to that described in Example 1(a) was repeated, except that 1.6 g of 2-amino-5-(4-fluorophenoxy)benzenethiol and 1.68 g of (±)-ethyl 3-(3-fluoro-4-methoxyphenyl)glycidate were employed, to afford 1.0 g of the title compound as a syrup.

Nuclear Magnetic Resonance Spectrum (CDCl$_3$) δ ppm:
1.15 (3H, triplet, J=7 Hz);
3.81 (3H, singlet);
3.6–4.6 (7H, multiplet);
6.5–7.4 (10H, multiplet).

23(b) 3-[2-Amino-5-(4-fluorophenoxy)phenyl]thio-3-(3-fluoro-4-methoxyphenyl)-2-hydroxyphenylpropionic acid A procedure similar to that described in Example 1(b) was repeated, except that 1 g of ethyl 3-[2-amino- 5-(4-fluorophenoxy)phenyl]thio-3-(3-fluoro-4-methoxyphenyl)-2-hydroxypropionate [prepared as described in step (a) above] were employed, to afford 920 mg of the title compound.

23(c) (±)-cis-2-(3-Fluoro-4-methoxyphenyl)-8-(4-fluorophenoxy)-2,3-dihydro-3-hydroxy-1,5-benzothiazepin-4(5H)-one A procedure similar to that described in Example 1(c) was repeated, except that 920 mg of 3-[2-amino- 5-(4-fluorophenoxy)phenyl]thio-3-(3-fluoro-4-methoxyphenyl)-2-hydroxypropionic acid [prepared as described in step (b) above] were employed, to afford 200 mg of the title compound as a solid.

Nuclear Magnetic Resonance Spectrum (hexadeuterated dimethyl sulfoxide) δ ppm:
3.83 (3H, singlet);
4.33 (1H, triplet, J=7 Hz);
4.77 (1H, doublet, J=7 Hz);
5.03 (1H, doublet, J=7 Hz);
6.8–7.4 (10H, multiplet).

23(d) (±)-cis-5-(2-Dimethylaminoethyl)-2-(3-fluoro-4-methoxyphenyl)-8-(4-fluorophenoxy)-2,3-dihydro-3-hydroxy-1,5-benzothiazepin-4(5H)-one A procedure similar to that described in Example 1(d) was repeated, except that 180 mg of (±)-cis-2-(3-fluoro-4-methoxyphenyl)-8-(4-fluorophenoxy)-2,3-dihydro- 3-hydroxy-1,5-benzothiazepin-4(5H)-one [prepared as described in step (c) above] were employed, to afford 80 mg of the title compound as a wax. This compound was used in the following reaction without further purification.

EXAMPLE 24

(±)-cis-3-Acetoxy-5-(2-dimethylaminoethyl)-2-(3-fluoro-4-methoxyphenyl)-8-(4-fluorophenoxy)-2,3-dihydro-1,5-benzothiazepin-4(5H)-one A procedure similar to that described in Example 2 was repeated, except that 80 mg of (±)-cis-5-(2- dimethylaminoethyl)-2-(3-fluoro-4-methoxyphenyl)-8-(4-fluorophenoxy)-2,3-dihydro-3-hydroxy-1,5-benzothiazepin(4(5H)-one (prepared as described in Example 23) were employed, to afford 32 mg of the title compound as an amorphous solid.

Nuclear Magnetic Resonance Spectrum (CDCl$_3$) δ ppm:
1.98 (3H, singlet);
2.29 (6H, singlet);
2.0–2.8 (2H, multiplet);

3.3–4.0 (1H, multiplet);
3.89 (3H, singlet);
4.1–4.7 (1H, multiplet);
4.93 (1H, doublet, J=7 Hz);
5.18 (1H, doublet, J=7 Hz);
6.7–7.6 (10H, multiplet).

In a manner similar to that described in Example 2, the title compound described above was converted into its hydrochloride.

EXAMPLE 25

(±)-cis-5-(2-Dimethylaminoethyl)-2,3-dihydro-3-hydroxy-2-(4-methoxyphenyl)-8-(3-methylphenoxy)-1,5-benzothiazeoin-4(5H)-one

25(a) Methyl 3-[2-amino-5-(3-methylphenoxy)phenyl]thio-2-hydroxy-3-(4-methoxyphenyl)propionate A procedure similar to that described in Example 1(a) was repeated, except that 5.16 g of 2-amino-5-(3methylphenoxy)benzenethiol and 4.64 g of (±)-methyl 3-(4-methoxyphenyl)glycidate were employed, to afford 1.79 g of the title compound as crystals, melting at 112–115° C.

Nuclear Magnetic Resonance Spectrum (CDCl$_3$) δ ppm:
2.27 (3H, singlet);
3.61 (3H, singlet);
3.72 (3H, singlet);
3.80–4 50 (5H, multiplet);
6.47–7.47 (11H, multiplet).

25(b) 3-[2-Amino-5-(3-methylphenoxy)phenyl]thio-2-hydroxy-3-(4-methoxyphenyl)propionic acid A procedure similar to that described in Example 1(b) was repeated, except that 1.90 g of methyl 3-[2-amino-5-(3-methylphenoxy)phenyl]thio-2-hydroxy-3-(4-methoxyphenyl)propionate [prepared as described in step (a) above] were employed, to afford 1.79 g of the title compound as crystals, melting at 163–165° C.

25(c) (±)-cis-2,3-Dihydro-3-hydroxy-2-(4-methoxyphenyl)-8-(3-methylphenoxy)-1,5-benzothiazepin-4(5H)-one A procedure similar to that described in Example 1(c) was repeated, that 1.70 g of 3-[2-amino-5- (3-methylphenoxy)phenyl]thio-2-hydroxy-3-(4-methoxyphenyl)propionic acid [prepared as described in step (b) above] were employed, to afford 1.10 g of the title compound as crystals, melting at 201–202° C.

Nuclear Magnetic Resonance Spectrum (CDCl$_3$+hexadeuterated dimethyl sulfoxide) δ ppm:
2,31 (3H, singlet);
3.24 (1H, singlet);
3.76 (3H, singlet);
4.40 (1H, doublet, J=6 Hz);
5.02 (1H, doublet, J=6 Hz);
6.67–7.70 (11H, multiplet);
10.16 (1H, singlet).

25(d) (±)-cis-5-(2-Dimethylaminoethyl)-2,3-dihydro-3-hydroxy-2-(4-methoxyphenyl)-8-(3-methylphenoxy)-1,5-benzothiazepin-4(5H)-one A procedure similar to that described in Example 1(d) was repeated, except that 0 5 g of (±)-cis-2,3-dihydro-3-hydroxy-2-(4-methoxyphenyl)-8-(3-methylphenoxy)-1,5-benzothiazepin-4(5H)-one [prepared as described in step (c) above] were employed, to afford 0.52 g of the title compound as a syrup.

Nuclear Magnetic Resonance Spectrum (CDCl$_3$) δ ppm:
2.29 (6H, singlet);
2.05–3.20 (3H, multiplet);
3.35–4.05 (1H, multiplet);
3.78 (3H, singlet);
4.05–4.75 (1H, multiplet);
4.32 (1H, doublet, J=7 Hz);
4.87 (1H, doublet, J=7 Hz);
6.50–7.90 (11H, multiplet).

EXAMPLE 26

(±)-cis-3-Acetoxy-5-(2-dimethylaminoethyl)-2,3-dihydro-2-(4-methoxyphenyl)-8-(3-methylphenoxy)-1,5-banzothiazpin-4(5H)-one A procedure similar to that described in Example 2 was repeated, except that 0.52 g of (±)-cis-5-(2- dimethylaminoethyl)-2,3-dihydro-3-hydroxy-2-(4-methoxyphenyl)-8-(3-methylphenoxy)-1,5-benzothiazepin-4(5H)-one (prepared as described in Example 25) were employed, to afford 0.23 g of the title compound as a gum.

Nuclear Magnetic Resonance Spectrum (CDCl$_3$) δ ppm:
1.90 (3H, singlet);
2.28 (6H, singlet);
2.36 (3H, singlet);
2.10–3.20 (2H, multiplet);
3.30–4.00 (1H, multiplet);
3.78 (3H, singlet);
4.10–4.75 (1H, multiplet);
4.96 (1H, doublet, J=7 Hz);
5.22 (1H, doublet, J=7 Hz);
6.60–7.65 (11H, multiplet).

In a manner similar to that described in Example 2, the above compound was converted into its hydrochloride, melting at 195–198° C., by treatment with a 4N solution of hydrogen chloride in dioxane.

EXAMPLE 27

(±)-cis-5-(2-Dimethylaminoethyl)-2,3-dihydro-3-hydroxy-8-(4-methoxyphenoxy)-2-(4-methoxyphenyl)-1,5-benzothiaz-epin-4(5H)-one

27(a) Methyl 3-[2-amino-5-4-methoxyphenoxy)phenyl]thio-2-hydroxy-3-(4-methoxyphenyl)propionate A procedure similar to that described in Example 1(a) was repeated, except that 7.67 g of 2-amino-5-(4-methoxyphenoxy)benzenethiol and 2.68 g of (±)-methyl 3-(4-methoxyphenyl)glycidate were employed, to afford 1.76 g of the title compound as a paste.

Nuclear Magnetic Resonance Spectrum (CDCl$_3$) δ ppm:
3.40–4.90 (5H, multiplet);
3.62 (3H, singlet);
3.77 (6H, singlet);
6.40–7.50 (11H, multiplet).

27(b) 3-[2-Amino-5-(4-methoxyphenoxy)phenyl]thio-2-hydroxy-3-(4-methoxyphenyl)propionic acid A procedure similar to that described in Example 1(b) was repeated, except that 1.76 g of methyl 3-[2-amino-5-

(4-methoxyphenoxy)phenyl]thio-2-hydroxy-3-(4-methoxyphenyl)propionate [prepared as described in step (a) above] were employed, to give 442 mg of the title compound.

27(c) (±)-cis-2,3-Dihydro-3-hydroxy-8-(4-methoxyphenoxy)-2-(4-methoxyphenyl)-1,5-benzothiazepin-4(5H)-one A procedure similar to that described in Example 1(c) was repeated, except that 0.42 g of 3-[2-amino-5-(4-methoxyphenoxy)phenyl]thio-2-hydroxy- 3-(4-methoxyphenyl)propionic acid [prepared as described in step (b) above] were employed, to afford 0.32 g of the title compound as colorless needles, melting at 213-214° C.
Nuclear Magnetic Resonance Spectrum (CDCl$_3$) δ ppm:
3.00 (1H, broad);
3.77 (6H, singlet);
4.50 (1H, multiplet);
5.07 (1H, doublet, J=7 Hz);
6.75-7.65 (11H, multiplet);
8.53 (1H, singlet).

27(d) (±)-cis-5-(2-Dimethylaminoethyl)-2,3-dihydro-3-hydroxy-8-(4-methoxyphenoxy)-2-(4-methoxyphenyl)-1,5-benzothlazepin-4(5H)-one A procedure similar to that described in Example 1(d) was repeated, except that 0.3 g of (±)-cis-2,3- dihydro-3-hydroxy-8-(4-methoxyphenoxy)-2-(4-methoxyphenyl)-1,5-benzothiazepin-4(5H)-one [prepared as described in step (c) above] were employed, to afford 0.16 g of the title compound as an amorphous solid.
Nuclear Magnetic Resonance Spectrum (CDCl$_3$) δ ppm:
2.10-3.15 (2H, multiplet);
2.28 (6H, singlet);
2.83 (1H, singlet);
3.80 (6H, singlet);
3.35-4.00 (1H, multiplet);
4.15-4.75 (1H, multiplet);
4.30 (1H, doublet, J=7 Hz);
4.85 (1H, doublet, J=7 Hz);
6.00-7.70 (11H, multiplet).

EXAMPLE 28

(±)-cis-3-Acetoxy-5-(2-dimethylaminoethyl)-2,3-dihydro-8-(4-methoxyphenoxy)-2-(4-methoxyphenyl)-1,5-benzothlazepin-4-(5H)-one A procedure similar to that described in Example 2 was repeated, except that 160 mg of (±)-cis-5-(2-dimethylaminoethyl)-2,3-dihydro-3-hydroxy-8-(4-methoxyphenoxy)-2-(4-methoxyphenyl)-1,5-benzothiazepin-4(5H)-one (prepared as described in Example 27) were employed, to afford 109 mg of the title compound.
Nuclear Magnetic Resonance Spectrum (CDCl$_3$) δ ppm:
1.88 (3H, singlet);
2.10-3.00 (2H, multiplet);
2.26 (6H, singlet);
3.40-3.95 (1H, multiplet);
3.80 (6H, singlet);
4.15-4.75 (1H, multiplet);
4.95 (1H, doublet, J=7 Hz);
5.20 (1H, doublet, J=7 Hz);
6.80-7.65 (11H, multiplet).

Following a procedure similar to that described in Example 2, this compound was converted into its hydrochloride, melting at 180-182° C.

EXAMPLE 29

(±)-cis-8-(4-Chlorophenoxy)-5-(2-dimethylaminoethyl)-2,3-dihydro-3-hydroxy-2-(4-methoxyphenyl)-1,5-benzothiazpin-4-(5H)-one 29(a) Methyl 3-[2-amino-5-(4-chlorophenoxy)phenyl]thio-2-hydroxy-3-(4-methoxyphenyl)propionate A procedure similar to that described in Example 1(a) was repeated, except that 8.00 g of 2-amino-5- (4-chlorophenoxy)benzenethiol and 6.02 g of (±)-methyl 3-(4-methoxyphenyl)glycidate were employed, to afford 6.30 g of the title compound as a paste.

29(b) 3-[2-Amino-5-(4-chlorophenoxy)phenyl]thio-2-hydroxy-3-(4-methoxyphenyl)propionic acid A procedure similar to that described in Example 1(b) was repeated, except that 6.30 g of methyl 3-[2-amino-5-(4-chlorophenoxy)phenyl]thio-2-hydroxy-3-(4-methoxyphenyl)propionate [prepared as described in step (a) above] were employed, to afford 3.48 g of the title compound as crystals, melting at 179-181° C.
Nuclear Magnetic Resonance Spectrum (CDCl$_3$+hexadeuterated dimethyl sulfoxide) δ ppm:
3.70 (3H, singlet);
4.30 (1H, doublet, J=7Hz);
4.46 (1H, doublet, J=7Hz);
6.45-7.50 (11H, multiplet).

29(c) (±)-cis-8-(4-Chlorophenoxy)-2,3-dihydro-3-hydroxy-2-(4-methoxyphenyl)-1,5-benzothiazepin-4(5H)-one A procedure similar to that described in Example 1(c) was repeated, except that 3.00 g of 3-[2-amino- 5-(4-chlorophenoxy)phenyl]thio-2-hydroxy-3-(4-methoxyphenyl)propionic acid [prepared as described in step (b) above] were employed to afford 1.80 g of the title compound as crystals, melting at 243-245° C.
Nuclear Magnetic Resonance Spectrum (CDCl$_3$) δ ppm:
3.20 (1H, singlet);
3.77 (3H, singlet);
4.38 (1H, doublet, J=7Hz);
5.06 (1H, doublet, J=7Hz);
6.70-7.60 (11H, multiplet);
10.34 (1H, singlet).

29(d) (±)-cis-8-(4-Chlorophenoxy)-5-(2-dimethylaminoethyl)-2,3-dihydro-3-hydroxy-2-(4-methoxyphenyl)-1,5-benzothiazepin-4(5H)-one A procedure similar to that described in Example 1(d) was repeated, except that 0.5 g of (±)-cis-8-(4-chlorophenoxy)-2,3-dihydro-3-hydroxy-2-(4-methoxyphenyl)- 1,5-benzothiazepin-4(5H)-one [prepared as described in step (c) above] were employed, to afford 317 mg of the title compound as an amorphous solid.
Nuclear Magnetic Resonance Spectrum (CDCl$_3$) δ ppm:
2.15-3.00 (2H, multiplet);
2.25 (6H, singlet);
2.80 (1H, singlet);
3.76 (3H, singlet);

3.40–4.75 (2H, multiplet);
4.30 (1H, doublet, J=7Hz);
4.90 (1H, doublet, J=7Hz);
6.80–7.65 (11H, multiplet).

EXAMPLE 30

(±)-cis-3-Acetoxy-8-(4-chlorophenoxy)-2,3-dihydro-5-(2-dimethylaminoethyl)-2-(4-methoxyphenyl)-1,5-benzothiazepin-4-(5H)-one A procedure similar to that described in Example 2 was repeated, except that 317 mg of (±)-cis-8-(4-chloro- phenoxy)-2,3-dihydro-5-(2-dimethylaminoethyl)-3-hydroxy- 2-(4-methoxyphenyl)-1,5-benzothiazepin-4(5H)-one (prepared as described in Example 29) were employed, to afford 289 mg of the hydrochloride of the title compound as an amorphous solid.

Nuclear Magnetic Resonance Spectrum (CDCl$_3$) δ ppm:
1.87 (3H, singlet);
2.89 (6H, singlet);
3.10–3.90 (2H, multiplet);
4.00–4.70 (2H, multiplet);
4.98 (1H, doublet, J=7Hz);
5.18 (1H, doublet, J=7Hz);
6.70–7.80 (11H, multiplet).

EXAMPLE 31

(2S, 3S)-5-(2-Dimethylaminoethyl)-2-(3-fluoro-4-methoxyphenyl)-8-(4-fluorophenoxy)-2,3-dihydro-3-hydroxy-1,5-benzothiazepin-4(5H)-one

31(a) l-Menthyl (2S, 3S)-3-[2-amino-5-(4-fluorophenoxy)phenyl]thio-3-(3-fluoro-4-methoxyphenyl)-2-hydroxypropionate A procedure similar to that described in Example 11(a) was repeated, except that, 18.6 g of l-menthyl trans-2,3-epoxy-3-(3-fluoro-4-methoxyphenyl)2-propionate (prepared as described in preparation 6) were reacted with 25.3 g of 2-amino-5-(4-fluorophenoxy)benzenethiol (prepared as described in preparation 8) in 200 ml of toluene to afford 4.52 g of the title compound as crystals, melting at 150–151° C.

Optical rotation $[\alpha]_D^{25}$ −17.8° (c=1, CHCl$_3$).
Nuclear Magnetic Resonance Spectrum (CDCl$_3$) δ ppm:
0.6–2.2 (18H, multiplet);
3.80 (3H, singlet);
4.20 (3H, broad singlet);
4.0–5.0 (3H, multiplet);
6.5–7.3 (10H, multiplet).

31(b) (2S, 3S)-3-[2-Amino-5-(4-fluorophenoxy)phenyl]thio-3-(3-fluoro-4-methoxyphenyl)-2-hydroxypropionic acid Following a procedure similar to that described in Example 11(b), 4.5 g of l-menthyl (2S, 3S)-3-[2- amino-5-(4-fluorophenoxy)phenyl]thio-3-(3-fluoro-4- methoxyphenyl)-2-hydroxypropionate [prepared as described in step (a) above] was hydrolyzed to give 1.28 g of the title compound as crystals, melting at 177–180° C.

Optical rotation $[\alpha]_D^{25}$ +146.5° (c=1, dimethylformamide).
Nuclear Magnetic Resonance Spectrum (hexadeuterated dimethyl sulfoxide) δ ppm:
3.77 (3H, singlet);
4.33 (1H, doublet, J=5.5 Hz);
4.50 (1H, doublet, J=5.5 Hz);
6.45 (4H, broad singlet);
6.5–7.4 (10H, multiplet).

31(c) (2S, 3S)-2-(3-Fluoro-4-methoxyphenyl)-8-(4-fluorophenoxy)-2,3-dihydro-3-hydroxy-1,5-benzothiazepin-4(5H)-one Following a procedure similar to that described in Example 11(c). 1.1 g of (2S, 3S)-3-[2-amino-5-(4-fluorophenoxy)phenyl]thio-3-(3-fluoro-4-methoxyphenyl)-2-hydroxypropionic acid [prepared as described in step (b) above] was cyclized intramolecularly to afford 900 mg of the title compound as crystals, melting at 222–224° C.

Optical rotation $[\alpha]_D^{25}$ +57.8° (c=1, dimethylformamide).
Nuclear Magnetic Resonance Spectrum (hexadeuterated dimethyl sulfoxide) δ ppm:
3.81 (3H, singlet);
4.33 (1H, triplet, J=7 Hz);
4.80 (1H, doublet, J=7 Hz);
5.05 (1H, doublet, J=7 Hz);
6.8–7.6 (10H, multiplet);
10.30 (1H, broad singlet).

31(d) (2S, 3S)-5-(2-Dimethylaminoethyl)-2-(3-fluoro-4-methoxyphenyl)-8-(4-fluorophenoxy)-2,3-dihydro-3-hydroxy-1,5-benzothiazepin-4(5H)-one Following a procedure similar to that described in Example 11(d), 865 mg of (2S, 3S)-2-(3-fluoro-4-methoxy- phenyl)-8-(4-fluorophenoxy)-2,3-dihydro-3-hydroxy-1,5-benzothiazepin-4(5H)-one [prepared as described in step (c) above] were alkylated with 2-dimethylaminoethyl chloride hydrochloride in 50 ml of methyl ethyl ketone to afford about 900 mg of the title compound as a syrup. The compound was used in the following reaction without further purification.

EXAMPLE 32

(2S, 3S)-3-Acetoxy-5-(2-dimethylaminoethyl)-2-(3-fluoro-4-methoxyphenyl)-8-(4-fluorophenoxy)-2,3-dihydro-1,5-benzothiazepin-4(5H)-one Following a procedure similar to that described in Example 12, 900 mg of (2S, 3S)-5-(2-dimethylaminoethyl)- 2-(3-fluoro-4-methoxyphenyl)-8-(4-fluorophenoxy)-2,3- dihydro-3-hydroxy-1,5-benzothiazepin-4(5H)-one (prepared as described in Example 31) were acetylated to afford 573 mg of the title compound as a wax.

Nuclear Magnetic Resonance Spectrum (CDCl$_3$) δ ppm:
1.98 (3H, singlet);
2.29 (6H, singlet);
2.1–3.0 (2H, multiplet);
3–4.0 (1H, multiplet);
3.87 (3H, singlet);
4.1–4.8 (1H, multiplet);
4.94 (1H, doublet, J=7 Hz);
5.18 (1H, doublet, J=7 Hz);
6.8–7.7 (10H, multiplet).

Following a procedure similar to that described in the second part of Example 14, the above compound was converted into 562 mg of its hydrochloride, melting at 128–132° C.

Optical rotation $[\alpha]_D = +60.8°$ (c=1, dimethylformamide).

Nuclear Magnetic Resonance Spectrum (hexadeuterated dimethyl sulfoxide) δ ppm:
- 1.87 (3H, singlet);
- 2.82 (6H, singlet);
- 3.0–3.8 (2H, multiplet);
- 3.87 (3H, singlet);
- 3.9–4.8 (2H, multiplet);
- 5.06 (1H, doublet, J=7 Hz);
- 5.21 (1H, doublet, J=7 Hz);
- 6.9–7.9 (10H, multiplet).

EXAMPLE 33

(2S, 3S)-5-(2-Dimethylaminoethyl)-2,3-dihydro-3-hydroxy-2-(4-methoxyphenyl)-8-(3,4-methylenedioxyphenoxy)-1,5-benzothiazepin-4(5H)-one

33(a) l-Menthyl (2S, 3S)-3-[2-amino-5-(3,4-methylenephenoxy)phenyl]thio-2-hydroxy-3-(4-methoxyphenyl)propionate Following a procedure similar to that described in Example 11(a), 20.6 g of l-menthyl trans-2,3-epoxy-3-(4-methoxyphenyl)propionate (prepared as described in Preparation 5) were reacted with 16.2 g of 2-amino-5-(3,4-methylenedioxyphenoxy)benzenethiol (prepared as described in Preparation 16) in 120 ml of toluene to afford 3.62 g of the title compound as crystals, melting at 145° C.

Optical rotation $[\alpha]_D^{25} -4.7°$ (c=1, chloroform).

Nuclear Magnetic Resonance Spectrum (CDCl$_3$) δ ppm:
- 0.6–2.2 (18H, multiplet);
- 3.72 (3H, singlet);
- 4.10 (3H, broad singlet);
- 4.38 (1H, doublet, J=4.5 Hz);
- 4.52 (1H, doublet, J=4.5 Hz);
- 5.90 (2H, singlet);
- 6.1–7.3 (10H, multiplet).

33(b) (2S, 3S)-3-[2-Amino-5-(3,4-methylenedioxyphenoxy)phenyl]thio-2-hydroxy-3-(4-methoxyphenyl)propionic acid Following a procedure similar to that described in Example 11(b), 3.52 g of l-menthyl (2S, 3S)-3-[2- amino-5-(3,4-methylenedioxyphenoxy)phenyl]thio-2-hydroxy-3-(4-methoxyphenyl)propionate [prepared as described in step (a) above] were hydrolyzed to afford 1.25 g of the title compound as crystals, melting at 112–113° C.

Optical rotation $[\alpha]_D^{25} +275.5°$ (c=1, dimethylformamide).

Nuclear Magnetic Resonance Spectrum (hexadeuterated dimethyl sulfoxide) δ ppm:
- 3.67 (3H, singlet);
- 4.24 (1H, doublet, J=6 Hz);
- 4.40 (1H, doublet, J=6 Hz);
- 5.96 (2H, singlet);
- 6.1–7.2 (10H, multiplet).

33(c) (2S, 3S)-2,3-Dihydro-3-hydroxy-2-(4-methoxyphenyl)-8-(3,4-methylenedioxyphenoxy)-1,5-benzothiazepin-4(5H)-one Following a procedure similar to that described in Example 11(c), 1.15 g of (2S, 3S)-3-[2-amino-5-(3,4-methylenedioxyphenoxy)phenyl]thio-2-hydroxy-3-(4-methoxyphenyl)propionic acid [prepared as described in step (b) above] was cyclized intramolecularly to afford 0.74 g of the title compound as crystals, melting at 188° C.

Optical rotation $[\alpha]_D^{25} +90.7°$ (c=1, dimethylformamide).

Nuclear Magnetic Resonance Spectrum (hexadeuterated dimethyl sulfoxide) δ ppm:
- 3.4 (1H, broad singlet);
- 3.74 (3H, singlet);
- 4.33 (1H, doublet, J=7.5 Hz);
- 5.04 (1H, doublet, J=7.5 Hz);
- 6.04 (2H, singlet);
- 6.4–7.45 (10H, multiplet).

33(d) (2S, 3S)-5-(2-dimethylaminoethyl)-2,3-dihydro-3-hydroxy-2-(4-methoxyphenyl)-8-(3,4-methylenedioxy- phenoxy)-1,5-benzothiazepin-4(5H)-one Following a procedure similar to that described in Example 11(d). 0.68 g of (2S, 3S)-2,3-dihydro-3-hydroxy- 2-(4-methoxyphenyl)-8-(3,4-methylenedioxyphenoxy)-1,5- benzothiazepin-4(5H)-one [prepared as described in step (c) above] was alkylated with 2-dimethylaminoethyl chloride hydrochloride to afford 0.72 g of the title compound as a gum.

Nuclear Magnetic Resonance Spectrum (CDCl$_3$) δ ppm:
- 2.28 (6H, singlet);
- 2.4–3.0 (2H, multiplet);
- 3.0 (1H, singlet);
- 3.4–3.9 (1H, multiplet);
- 3.80 (3H, singlet);
- 4.2–4.6 (1H, multiplet); 4.35 (1H, doublet, J=7 Hz);
- 4.88 (1H, doublet, J=7 Hz);
- 6.00 (2H, singlet);
- 6.5–7.55 (10H, multiplet).

EXAMPLE 34

(2S, 3S)-3-Acetoxy-5-(2-dimethylaminoethyl)-2,3-dihydro-2-(4-methoxyphenyl)-8-(3,4-methylenedioxyphenoxy)-1,5-benzothiazepin-4(5H)-one Following a procedure similar to that described in Example 12, 0.72 g of (2S, 3S)-5-(2-dimethylaminoethyl)-2,3-dihydro-3-hydroxy-2-(4-methoxyphenyl)-8-(3,4-methylenedioxyphenoxy)-1,5-benzothiazepin-4(5H)-one (prepared as described in Example 33) was acetylated to afford 0.80 g o of the title compound as an amorphous solid.

Nuclear Magnetic Resonance Spectrum (CDCl$_3$) δ ppm:
- 1.86 (3H, singlet);
- 2.24 (6H, singlet);
- 2,3–3.0 (2H, multiplet);
- 3.75 (3H, singlet);
- 3.35–4.0 (1H, multiplet);
- 4.0–4.6 (1H, multiplet);
- 4.97 (1H, doublet, J=7 Hz);
- 5.16 (1H, doublet, J=7 Hz);
- 5.95 (2H, singlet);
- 6.4–7.55 (10H, multiplet).

Following a procedure similar to that described in the second part of Example 12, 0.80 g of the above compound was converted into its fumarate, which was triturated with a small amount of a mixture of ethyl acetate and cyclohexane to give an amorphous powder. The yield was 0.87 g.

Optical rotation $[\alpha]_D^{25}$ ±57.3° (c=1, dimethylformamide).

Nuclear Magnetic Resonance Spectrum (hexadeuterated dimethyl sulfoxide) δ ppm:
 1.85 (3H, singlet);
 2.46 (6H, singlet);
 2,3–3.4 (2H, multiplet);
 3.78 (3H, singlet);
 3.5–4.7 (2H, multiplet);
 5.05 (1H, doublet, J=8 Hz);
 5.15 (1H, doublet, J=8 Hz);
 6.10 (2H, singlet);
 6.63 (2H, singlet);
 6.6–7.8 (10H, multiplet).

EXAMPLE 35

(2S, 3S)-5-(2-Diethylaminoethyl)-2,3-dihydro-3-hydroxy-2-(4-methoxyphenyl)-8-phenoxy-1,5-benzothiazepin-4(5H)-one Following a procedure similar to that described in Example 11(d), 1.0 g of (2S, 3S)-2,3-dihydro-3-hydroxy-2-(4-methoxyphenyl)-8-phenoxy-1,5-benzothiazepin-4(5H)-one [prepared as described in Example 1(c)] was alkylated with 525 mg of diethylaminoethyl chloride hydrochloride to afford 1.12 g of the title compound as a syrup.

Nuclear Magnetic Resonance Spectrum (CDCl₃) δ ppm:
 1.00 (6H, triplet, J=7 Hz);
 2.58 (4H, quartet, J=7 Hz);
 2.3–3.2 (3H, multiplet);
 3.80 (3H, singlet);
 3.5–4.0 (1H, multiplet);
 4.15–4.65 (2H, multiplet);
 4.91 (1H, doublet, J=8 Hz);
 6.8–7.6 (12H, multiplet).

EXAMPLE 36

(2S, 3S)-3-Acetoxy-5-(2-diethylaminoethyl)-2,3-dihydro-2-(4-methoxyphenyl)-8-phenoxy-1,5-benzothiazepin-4(5H)-one Following a procedure similar to that described in Example 12, 1.12 g of (2S, 3S)-5-(2-diethylaminoethyl)-2,3-dihydro-3-hydroxy-2-(4-methoxyphenyl)-8-phenoxy-1,5-benzothiazepin-4(5H)-one (prepared as described in Example 35) was acetylated to afford 1.15 g of the title compound as an amorphous solid.

Nuclear Magnetic Resonance Spectrum (CDCl₃) δ ppm:
 0.98 (6H, triplet, J=7 Hz);
 1.86 (3H, singlet);
 2.56 (4H, quartet, J=7 Hz);
 2.3–3.2 (2H, multiplet);
 3.77 (3H, singlet);
 3.45–4.0 (1H, multiplet);
 4.05–4.6 (1H, multiplet);
 4.99 (1H, doublet, J=7.5 Hz);
 5.23 (1H, doublet, J=7.5 Hz);
 6.8–7.6 (12H, multiplet).

The above compound was treated with a 4N solution of hydrogen chloride in ethyl acetate to afford the hydrochloride of the title compound as crystals, melting at 149–152° C.

Optical rotation $[\alpha]_D^{25}$ +90.8° (c=1, dimethylformamide).

Nuclear Magnetic Resonance Spectrum (hexadeuterated dimethyl sulfoxide) δ ppm:
 1.22 and 1.24 (6H, triplet, J=7.5 Hz);
 1.85 (3H, singlet);
 3.18–3.3 (5H, multiplet);
 3.3–3.5 (1H, multiplet);
 3.77 (3H, singlet);
 4.0–4.2 (1H, multiplet);
 4.3–4.45 (1H, multiplet);
 5.07 (1H, doublet, J=7.5 Hz);
 5.19 (1H, doublet, J=7.5 Hz);
 6.85–7.75 (12H, multiplet).

EXAMPLE 37

(2S, 3S)-5-(2-Dimethylaminoethyl)-8-(4-fluorobenzyl)-2,3-dihydro-3-hydroxy-2-(4-methoxyphenyl)-1,5-benzothiazepin-4(5H)-one

37(a) l-Menthyl (2S, 3S)-3-[2-amino-5-(4-fluoro-benzyl)phenyl]thio-2-hydroxy-3-(4-methoxyphenyl)propionate Following a procedure similar to that described in Example 17(a), 42.9 g of l-menthyl trans-2,3-epoxy-3-(4-methoxyphenyl)propionate (prepared as described in preparation 5) were reacted with 31.2 g of 2-amino-5-(4-fluorobenzyl)benzenethiol in 350 ml of toluene to afford 21.26 g of the title compound as crystals, melting at 149–150° C.

Optical rotation $[\alpha]_D^{25}$ +178.0° (c=1, dimethylformamide).

Nuclear Magnetic Resonance Spectrum (CDCl₃) δ ppm:
 0.65–1.7 (17H, multiplet);
 1.95–2.01 (1H, multiplet);
 3.64 (2H, singlet);
 3.76 (3H, singlet);
 4.11 (1H, doublet, J=7.5 Hz);
 4.26 (2H, broad singlet);
 4.37 (1H, doublet, J=5 Hz);
 4.51 (1H, doublet of doublets, J=5 & 7.5 Hz);
 4.73 (1H, doublet of triplets, J=4.5 & 11Hz);
 6.60–7.26 (11H, multiplet).

37(b) (2S, 3S)-3-[2-Amino-5-(4-fluorobenzyl)phenyl]thio-2-hydroxy-3-(4-methoxyphenyl)propionic acid Following a procedure similar to that described in Example 17(b), 20.65 g of l-menthyl (2S, 3S)-3-[2-amino-5-(4-fluorobenzyl)phenyl]thio-2-hydroxy-3-(4-methoxyphenyl)propionate [prepared as described in step (a) above] were hydrolyzed to afford 8.67 g of the title compound as crystals, melting at 165.5–167° C.

Optical rotation $[\alpha]_D^{25}$ +318.6° (c=1, dimethylformamide).

Nuclear Magnetic Resonance Spectrum (hexadeuterated dimethyl sulfoxide) δ ppm:
 3.57 (2H, singlet);
 3.70 (3H, singlet);
 4.25 (1H, doublet, J=5.5 Hz);
 4.32 (1H, doublet, J=5.5 Hz);
 6 56–7.14 (11H, multiplet).

37(c) (2S, 3S)-8-(4-Fluorobenzyl)-2,3-dihydro-3-hydroxy-2-(4-methoxyphenyl)-1,5-benzothiazepin-4(5H)-one Following a procedure similar to that described in Example 17(c), 8.37 g of (2S, 3S)-3-[2-amino-5-(4-fluorobenzyl)phenyl]thio-2-hydroxy-3-(4-methoxyphenyl)propionic acid [prepared as described in step (b) above] were cyclized intramolecularly to afford 7.92 g of the title compound as crystals, melting at 216–218° C.

Optical rotation $[\alpha]_D^{25} +93.7°$ (c=1, dimethylformamide).

Nuclear Magnetic Resonance Spectrum (hexadeuterated dimethyl sulfoxide) δ ppm:
3.75 (3H, singlet);
3.93 (2H, singlet);
4.27 (1H, triplet, J=7 Hz);
4.64 (1H, doublet, J=7 Hz);
5.02 (1H, doublet, J=7 Hz);
6.86–7.45 (11H, multiplet);
10.23 (3H, singlet).

37(d) (2S, 3S)-5-(2-Dimethylaminoethyl)-8-(4-fluorobenzyl)-2,3-dihydro-3-hydroxy-2-(4-methoxyphenyl)-1,5-benzothiazepin-4-(5H)-one Following a procedure similar to that described in Example 17(d), 7.62 g of (2S, 3S)-8-(4-fluorobenzyl)-2,3-dihydro-3-hydroxy-2-(4-methoxyphenyl)-1,5-benzothiazepin-4(5H)-one [prepared as described in step (c) above] were alkylated; with 3.22 g of 2-dimethylaminoethyl chloride hydrochloride to afford 8.44 g of the title compound as a foamy solid.

Optical rotation $[\alpha]_D^{25} +108.8°$ (c=1, chloroform).

Nuclear Magnetic Resonance Spectrum (CDCl₃) δ ppm:
2.24 (6H, singlet);
2.2–3.0 (3H, multiplet);
3.4–4.0 (1H, multiplet);
3.77 (3H, singlet);
3.93 (2H, singlet);
4.2–4.7 (2H, multiplet);
4.86 (1H, doublet, J=7.5 Hz);
6.9–7.5 (11H, multiplet).

EXAMPLE 38

(2S, 3S)-3-Acetoxy-5-(2-dimethylaminoethyl)-8-(4-fluorobenzyl)-2,3-dihydro-2-(4-methoxyphenyl)-1,5-benzothiazepin-4(5H)-one Following a procedure similar to that described in Example 18, 8.44 g of (2S, 3S)-5-(2-dimethylaminoethyl)-8-(4-fluorobenzyl)-2,3-dihydro-3-hydroxy-2-(4-methoxy- phenyl)-1,5-benzoihiazepin-4(5H)-one (prepared as described in Example 37) were acetylated to afford 8.52 g of the title compound as crystals melting at 154–155.5° C.

Optical rotation $[\alpha]_D^{25} +82.1°$ (c=1, dimethylformamide).

Nuclear Magnetic Resonance Spectrum (CDCl₃) δ ppm:
1.89 (3H, singlet);
2.27 (6H, singlet);
2.39–2.49 (1H, multiplet);
2.64–2.73 (1H, multiplet);
3.63–3.73 (1H, multiplet);
3.82 (3H, singlet);
3.96 (2H, singlet);
4.33–4.44 (1H, multiplet);
4.99 (1H, doublet, J=7.5 Hz);
5.15 (1H, doublet J=7.5 Hz);
6.67–7.48 (11H, multiplet).

Following a procedure similar to that described in Example 18, 499 mg of the compound described above were treated with hydrogen chloride in ethyl acetate to afford 466 mg of its hydrochloride as crystals, melting at 190–193° C.

Optical rotation $[\alpha]_D^{25} +80.9°$ (c=1, dimethylformamide).

Nuclear Magnetic Resonance Spectrum (hexadeuterated dimethyl sulfoxide) δ ppm:
1.82 (3H, singlet);
2.82 (6H, singlet);
3.08–3.18 (1H, multiplet);
3.32–3.42 (1H, multiplet);
3.77 (3H, singlet);
4.01 (2H, singlet);
4.01–4.09 (1H, multiplet);
4.31–4.37 (1H, multiplet);
4.97 (1H, doublet, J=8 Hz);
5.14 (1H, doublet, J=8 Hz);
6.89–7.62 (11H, multiplet).

Following a procedure similar to that described in Example 18, the compound described above was converted into its L-tartarate, melting at 95–97° C. (softening)

Optical rotation $[\alpha]_D^{25} +63.0°$ (c=1, dimethylformamide).

Nuclear Magnetic Resonance Spectrum (hexadeuterated dimethyl sulfoxide) δ ppm:
1.81 (3H singlet);
2.30 (6H, singlet);
2.4–2.55 (1H, multiplet);
2.68–2.80 (1H, multiplet);
3.7–3.83 (1H, multiplet);
3.77 (3H, singlet);
3.99 (2H, singlet);
4.20 (2H, singlet);
4.20–4.30 (1H, multiplet):
4.96 (1H, doublet. J=8 Hz);
5.11 (1H, doublet, J=8 Hz);
6.89–7.62 (11H, multiplet).

EXAMPLE 39

(2S, 3S)-5-(2-Dimethylaminoethyl)-2,3-dihydro-3-hydroxy-2-(4-methoxyphenyl)-8-[(5-methyl-2-thienyl)methyl]-1,5- benzothiazepin-4(5H)-one

39(a) l-Menthyl (2S, 3S)-3-[2-amino-5-[(5-methyl-2-thienyl)methyl]phenyl]thio-2-hydroxy-3-(4-methoxyphenyl)propionate Following a procedure similar to that described in Example 17(a), 52.35 g of l-menthyl trans-2,3-epoxy-3-(4-methoxyphenyl)propionate (prepared as described in Preparation 5) were reacted with 38.44 g of 2-amino-5-(5-methyl-2-thienyl)methylbenzenethiol in 450 ml of toluene to afford 12.75 g of the title compound as crystals, melting at 148–150° C.

Optical rotation $[\alpha]_D^{25} +150.1°$ (c=1, dimethylformamide).

Nuclear Magnetic Resonance Spectrum (CDCl₃) δ ppm:
0.65–2.1 (18H, multiplet);
2.31 (3H singlet);
3.76 (5H, singlet);
4.04 (1H, doublet, J=7.5 Hz);
4.23 (2H, broad singlet);
4.36 (1H, doublet, J=4.5 Hz)
4.51 (1H, doublet of doublets, J=4.5 & 7.5 Hz):
4.73 (1H, doublet of triplets, J=4.5 & 11Hz);
6.39–7.26 (9H, multiplet).

39(b) (2S, 3S)-3-2-Amino-5-[(5-methyl-2-thienyl)methyl]-phenyl]thio-2-hydroxy-3-(4-methoxyphenyl)propionic acid Following a procedure similar to that described in Example 17(b), 12.69 g of l-menthyl (2S, 3S)-3- [2-amino-5-[(5-methyl-2-thienyl)methyl]phenyl]- thio-2-hydroxy-3-(4-methoxyphenyl)propionate [prepared as described in step (a) above] were hydrolyzed to afford 5.36 g of the title compound as crystals, melting at 146-147.5° C. (with decomposition).

Optical rotation $[\alpha]_D^{25} +280.7°$ (c=1, dimethylformamide).

Nuclear Magnetic Resonance Spectrum (hexadeuterated dimethyl sulfoxide) δ ppm:
2.33 (3H, singlet);
3.67 (2H, singlet);
3.70 (3H, singlet);
4.25 (1H, doublet, J=5.5 Hz);
4.32 (1H, doublet, J=5.5 Hz);
6.35-7.14 (9H, multiplet).

39(c) (2S, 3S)-2,3-Dihydro-3-hydroxy-2-(4-methoxyphenyl)-8-[(5-methyl-2-thienyl)methyl]-1,5-benzothiazepin-4(5H)-one Following a procedure simliar to that described in Example 17(c), 5.3 g of (2S 3S)-3-]2-amino-5-[(5-methyl-2-thienyl)methyl]phenyl]thio-2-hydroxy-3-(4-methoxyphenyl)propionic acid [prepared as described in step (b) above] were cyclized intramolecularly to afford 2.76 g of the title compound as crystals, which colored at 150° C. and decomposed at 192-195° C.

Optical rotation $[\alpha]_D^{25}+98.9°$ C. (c=1, dimethylformamide).

Nuclear Magnetic Resonance Spectrum (hexadeuterated dimethyl sulfoxide) δ ppm:
2.36 (3H, singlet);
3.75 (3H, singlet);
4.05 (2H, singlet);
4.27 (1H, triplet J=6.5 Hz);
4.67 (1H, doublet. J=6.5 Hz);
5.03 (1H, doublet J=6.5 Hz);
6.61-7.46 (9H multiplet);
10.24 (1H, singlet).

39(d) (2S, 3S)-5-(2-Dimethylaminoethyl)-2,3-dihydro-3-hydroxy-2-(4-methoxyphenyl)-8-[(5-methyl-2-thienyl)methyl]-1,5-benzothiazepin-4(5H)-one Following a procedure similar to that described in Example 17(d), 2.7 g of (2S, 3S)-2,3-dihydro-3-hydroxy-2-(4-methoxyphenyl)-8-[(5-methyl-2-thienyl)methyl]-1,5- benzothiazepin-4(5H) one [prepared as described in step (c) above] were alkylated with 1.13 g of 2-dimethylaminoethyl chloride hydrochloride to afford 3.1 g of the title compound as a foamy solid.

Optical rotation $[\alpha]_D^{25}+103.7°$ (c=1, chloroform).

Nuclear Magnetic Resonance Spectrum (CDCl₃) δ ppm:
2.24 (6H, singlet);
2.40 (3H singlet);
2.2-3.0 (3H, multiplet);
3.4-4.0 (1H, multiplet);
3.77 (3H, singlet);
4.05 (2H, singlet);
4.0-4.7 (2H, multiplet);
4.86 (1H, doublet. J=7.5 Hz); 6.6-7.6 (9H, multiplet).

EXAMPLE 40

(2S, 3S)-3-Acetoxy-5-(2-dimethylaminoethyl)-2,3-dihydro-2-(4-methoxyphenyl)-8-[(5-methyl-2-thienyl)methyl]-1,5-benzothiazepin-4-(5H)-one Following a procedure similar to that described in Example 18, 3.1 g of (2S, 3S)-5-(2-dimethylaminoethyl)-2,3-dihydro-3-hydroxy-2-(4-methoxyphenyl)-8-[(5-methyl- 2-thienyl)methyl]-1,5-benzothiazepin-4(5H)-one (prepared as described in Example 39) were acetylated to afford 3.29 g of the title compound as crystals, melting at 131-134° C.

Optical rotation $[\alpha]_D^{25} 63.5°$ (c=1, chloroform).

Nuclear Magnetic Resonance Spectrum (CDCl₃) δ ppm:
1.86 (3H, singlet);
2.26 (6H, singlet);
2.41 (3H, singlet);
2.2-3.1 (2H, multiplet);
3.4-4.0 (1H, multiplet);
3.78 (3H, singlet);
4.04 (2H, singlet);
4.0-4.6 (1H, multiplet);
4.95 (1H, doublet, J=7 Hz);
5.14 (1H, doublet, J=7 Hz);
6.6-7.55 (9H, multiplet).

Following a procedure similar to that described in the second part of Example 18, 3.0 g of the compound described above were treated with hydrogen chloride in ethyl acetate to afford 3.10 g of the hydrochloride as an amorphous poWder.

Optical rotation $[\alpha]_D^{25}+74.1°$ (c=1, dimethylformamide).

Nuclear Magnetic Resonance Spectrum (CDCl₃) δ ppm:
1.83 (3H, singlet);
2.38 (3H, singlet);
2.79 (6H, singlet);
3.04-3.17 (1H, multiplet);
3.3-3.45 (1H, multiplet);
3.77 (3H, singlet);
4.14 (2H, singlet);
4.08-4.17 (1H multiplet);
4.36-4.45 (1H, multiplet);
4.98 (1H, doublet, J=7.5 Hz);
5.15 (1H, doublet, J=7.5 Hz);
6.64-7.65 (9H, multiplet).

PREPARATION 1

2-Amino-6-phenoxybenzothiazole 20.5 g of ammonium thiocyanate were added to a solution of 25 g of 4-phenoxyaniline in 250 ml of acetic acid, and the mixture was stirred, whilst cooling. While the internal temperature was maintained at 12 to 18° C., 6.95 ml of bromine was added dropwise to the mixture. After completion of the dropwise addition, the mixture was stirred for 2 hours, after which the solvent was removed by evaporation under reduced pressure. 300ml of ethyl acetate and 200 ml of water were added to the residue, and the resulting mixture was neutralized with sodium bicarbonate. The ethyl acetate layer was separated, washed with an aqueous solution of sodium chloride, and then dehydrated over anhydrous magnesium sulfate after which it was concentrated by evaporation under reduced pressure. The solid obtained was triturated in diisopropyl ether, and filtered to give 21.34 g of the title compound, melting at 171–172° C.

Nuclear Magnetic Resonance Spectrum (CDCl$_3$+hexadeuterated acetone) δ ppm:
5 9–7.0, (2H, broad peak);
6.8–7.8, (8H, multiplet).

PREPARATION 2

2-Amino-5-phenoxybenzenethiol 14 ml of ethylene glycol were added to a solution of 42.3 g of caustic potash dissolved in 49 ml of water, and after the air in the reaction vessel had been replaced by nitrogen, 10.57 g of 2-amino-6-phenoxybenzothiazole were added. While blowing nitrogen through the reaction mixture, the reaction was carried out on an oil bath at 135° C. for 2 hours. At the end of this time, the reaction mixture was cooled, 105 ml of toluene were added, and the mixture was ,neutralized by the addition of 42.3 ml of acetic acid. The toluene layer was separated, and the aqueous layer was once again extracted with toluene. The combined toluene extracts were washed with an aqueous solution of sodium bicarbonate, with water, and with an aqueous solution of sodium chloride, in that order, after which they were dried over anhydrous magnesium sulfate. The resulting solution was then concentrated by evaporation under reduced pressure, and the residue Was dried, to give 9.6 g of the title compound as a solid. This compound was used for the next reaction without further purification.

PREPARATION 3

2-Amino-6-phenylthiobenzothiazole

Following a procedure similar to that described in preparation 1, but using 12.0 g of 4-phenylthioaniline, 11.7 g of the title compound, melting at 180–182° C., were obtained.

Nuclear Magnetic Resonance Spectrum (hexadeuterated dimethyl sulfoxide) δ ppm:
7.05–7.40, (7H, multiplet);
7.58, (2H, broad singlet);
7.70, (1H, multiplet).

PREPARATION 4

2-Amino-5-phenylthiobenzenethiol

Following a procedure similar to that described in preparation 2, but using 5.0 g of 2-amino-6-phenylthiobenzothiazole, 4.5 g of the title compound were obtained as liquid. This compound was used in the next step without further purification.

PREPARATION 5 l-Menthyl trans-2,3-epoxy-3-(4-methoxyphenyl)propionate 5.8 g of a 55% W/W suspension of sodium hydride in mineral oil were added to a solution of 23.2 g of l-menthyl chloroacetate and 13.6 g of p-anisaldehyde dissolved in 200 ml of anhydrous tetrahydrofuran, and the mixture was stirred at 35° C. for 5 hours. At the end of this time 80 ml of a saturated aqueous solution of ammonium sulfate were added dropwise over 30 minutes to the resulting mixture, and then ethyl acetate and water were added thereto. The ethyl acetate layer was separated and dried over anhydrous anhydrous magnesium sulfate. The ethyl acetate was removed by evaporation under reduced pressure, and the liquid residue was purified by silica gel column chromatography using a 20 : 1 by volume mixture of ethyl acetate and hexane as the eluent to afford 18.0 g of the title compound.

Nuclear Magnetic Resonance Spectrum (CDCl$_3$) δ ppm:
0.7–2.2 (18H, multiplet);
3.44 (1H, multiplet);
3.79 (3H, singlet);
4.00 (1H, doublet J=2 Hz);
4 6–5.05 (1H, multiplet);
6.8–7.3 (4H. multiplet).

PREPARATION 6 l-Menthyl trans-2,3-epoxy-3-(3-fluoro-4-methoxyphenyl)propionate 7.4 g of a 55% w/w suspension of sodium hydridge in mineral oil were added to a solution of 36 g of l-menthyl chloroacetate and 13.1 g of 3-fluoro-4-methoxybenzaldehyde Optical rotation $[\alpha]_D^{25}$ +93.7° (c=1, dissolved in 350 ml of tetrahydrofuran, and the mixture was stirred at 30° C. for 7 hours. At the end of this time, 100 ml of a saturated aqueous solution of ammonium sulfate were slowly added dropwise to the reaction mixture, followed by an aqueous solution of sodium chloride, after which the mixture was stirred. The resulting mixture was left to stand and then the tetrahydrofuran layer was separated and dried over anhydrous anhydrous magnesium sulfate. The solvent was then removed under reduced pressure, after which the resulting oil was purified by column chromatography through silica gel using a 9:1 by volume mixture of hexane and ethyl acetate as the eluent, to afford 28.3 g of the title compound as a colorless viscous liquid.

Nuclear Magnetic Resonance Spectrum (CDCl$_3$) δ ppm:
1.4–2.4 (18H, multiplet);
3.40 (1H, doublet, J=2 Hz);
3.89 (3H, singlet);
3.97 (1H, doublet, J=2 Hz);
4.4–5.2 (1H, multiplet);
6.7–7.3 (3H, multiplet).

PREPARATION 7

2-Amino-6-(4-fluorophenoxy)benzothiazole 13 ml of acetic acid containing 6.5 ml of bromine were added dropwise at 13 to 15° C. to a solution of 25.6 g of 4-(4-fluorophenoxy)aniline and 19.2 g of ammonium thiocyanate in 185 ml of acetic acid. After completion of the addition, the mixture was stirred at room temperature for 1 hour and then the solvent was distilled off under reduced pressure. The residue was mixed with 300 ml of ethyl acetate and 200 ml of water, and the mixture was neutralized by adding powered potassium carbonate. The ethyl acetate layer was then separated and dried over anhydrous magnesium sulfate, and then the residue was concentrated by evaporation under reduced pressure. The crystalline residue was washed with diisopropyl ether to afford 26.7 g of the title compound, melting at 126–128° C.

Nuclear Magnetic Resonance Spectrum (CDCl$_3$) δ ppm:
5.52 (2H, broad singlet);
6.9–7.5 (7H, multiplet).

PREPARATION 8

2-Amino-5-(4-fluorophenoxy)benzenethiol 22 g of 2-amino-6-(4-fluorophenoxy)benzothiazole (prepared as described in preparation 7) were added to a mixture of a solution of 90 g of potassium hydroxide in 100 ml of water and 28 ml of ethylene glycol, and the mixture was stirred for 2 hours on an oil bath kept at 130° C under an atmosphere of nitrogen. After the mixture had been cooled to room temperature, 90 ml of acetic acid was added dropwise to the resulting homogenous solution to deposit a precipitate: this was extracted with toluene. The toluene extract was dried over anhydrous magnesium sulfate and concentrated by evaporation under reduced pressure, to afford 16 g of the title compound as a pale yellow solid.

PREPARATION 9

2-Amino-6-(3-methylphenoxy)benzothiazole

Following a procedure similar to that described in Preparation 1, 13.78 g of the title compound were obtained as light brown powdery crystals, melting at 91-98° C., from 13.5 g of 4-(3-methylphenoxy)aniline.

Nuclear Magnetic Resonance Spectrum (CDCl$_3$) δ ppm:
2.30 (3H, singlet);
5.32 (2H, broad);
6.55-7.70 (7H, multiplet).

PREPARATION 10

2-Amino-5-(3-methylphenoxy)benzenethiol

Following a procedure similar to that described in preparation 2, 5.16 g of the title compound were obtained as a pale yellow past from 6.00 g of 2-amino-6-(3-methylphenoxy)benzothiazole (prepared as described in preparation 9).

This compound was used in the following reaction without further purification.

PREPARATION 11

2-Amino-6-(4-methoxyphenoxy)benzothiazole

Following a procedure similar to that described in Preparation 1, 13.50 g of the title compound were obtained as light brown fine crystals, melting at 165-167° C., from 15.00 g of 4-(4-methoxyphenoxy)aniline.

PREPARATION 12

2-Amino-5-(4-methoxyphenoxy)benzenethiol

Following a procedure similar to that described in Preparation 2, 7.67 g of the title compound were obtained as a pale yellow paste from 7.00 g of 2-amino-6-(4-methoxyphenoxy)benzothiazole (prepared as described in preparation 11).

This compound was used in the following reaction without further purification.

PREPARATION 13

2-Amino-6-(4-chlorophenoxy)benzothiazole

Following a procedure similar to that described in Preparation 1, 8.15 g of the title compound were obtained as pale yellow needles melting at 157-160° C. from 9.47 g of 4-(4-chlorophenoxy)aniline.

PREPARATION 14

2-Amino-5-(4-chlorophenoxy)benzenethiol

Following a procedure similar to that described in Preparation 2, 8.00 g of the title compound were obtained as a yellow paste from 8.00 g of 2-amino-6-(4-chlorophenoxy)benzothiazole (prepared as described in preparation 13).

This compound was used in the following reaction without further purification.

PREPARATION 15

2-Amino-6-(3,4-methylenedioxyphenoxy)benzothiazole

Following a procedure similar to that described in Preparation 1, the title compound, melting at 154-157° C. was synthesized from 4-(3,4-methylenedioxyphenoxy)aniline.

Nuclear Magnetic Resonance Spectrum (CDCl$_3$+hexadeuterated dimethyl sulfoxide) δ ppm:
4.00 (2H, broad singlet);
5.94 (2H, singlet);
6.3-7.45 (6H, multiplet).

PREPARATION 16

2-Amino-5-(3,4-methylenedioxyphenoxy)benzenethiol

Following a procedure similar to that described in Preparation 2, 2-amino-6-(3,4-methylenedioxyphenoxy)benzothiazole (prepared as described in Preparation 15) was hydrolyzed With an alkali to afford the title compound as a yellow oil.

This compound was used in the following reaction without further purification.

PREPARATION 17

2-Amino-6-benzylbenzothiazole 11.2 ml of bromine were added dropWise to a solution of 39.7 g of 4-benzylaniline and 33 g of ammonium thiocyanate in 400 ml of acetic acid at a temperature of from 12 to 18° C. After completion of the addition, the mixture was stirred at room temperature for 2 hours and then the solvent was distilled off. The residue was mixed with 600 ml of ethyl acetate and 300 ml of water and the mixture was neutralized by the addition of potassium carbonate powder The ethyl acetate layer was separated, washed with an aqueous solution of sodium chloride, dried over anhydrous magnesium sulfate and concentrated by evaporation under reduced pressure. The residual solid was recrystallized from ethyl acetate to give 37.6 g of the title compound melting at 173-175° C.

Nuclear Magnetic Resonance Spectrum (CDCl$_3$) δ ppm:
4.00 (2H, singlet);
5.4 (2H, broad singlet):
7.1-7.55 (8H, multiplet).

PREPARATION 18

2-Amino-5-benzylbenzenethiol

A solution of 103 g of potassium hydroxide in 125 ml of water was mixed with 62.5 ml of ethylene glycol and 25 g of 2-amino-6-benzylbenzothiazole was added to the mixture under an atmosphere of nitrogen. The mixture was stirred whilst heating it on an oil bath kept at 135° C. for 7 hours. After it had been allowed to cool, the mixture was diluted with 250 ml of toluene and 105 ml of acetic acid were added dropwise to it. The toluene layer was separated off, and the aqueous solution remaining was again extracted with toluene. The combined toluene extracts were washed with an aqueous solution of sodium bicarbonate, with water and with an aqueous solution of sodium chloride, after which the resulting solution was dried over anhydrous magnesium sulfate. Distillation of the solvent afforded 21.0 g of the title compound as a syrup. This product crystallized on standing and was used in the following reaction without further purification.

PREPARATION 19

2-Amino-6-(2-thienyl)methylbenzothiazole

Following a procedure similar to that described in preparation 17, 25 g of the title compound, melting at 188–191° C. was prepared from 33 g of 4-(2-thienyl)methylaniline.

Nuclear Magnetic Resonance Spectrum (hexadeuterated dimethyl sulfoxide) δ ppm:
4.12 (2H, singlet);
6.84–7.50 (6H, multiplet).

PREPARATION 20

2-Amino-5-(2-thienyl)methylbenzenethiol

Following a procedure similar to that described in Preparation 18, 8.5 g of the title compound were prepared from 9.3 g of 2-amino-6-(2-thienyl)methylbenzothiazole (prepared as described in preparation 19). This product was used in the following reaction without further purification.

PREPARATION 21

2-Amino-6-(4-fluorobenzyl)benzothiazole

Following a procedure similar to that described in Preparation 17, 33.8 g of the title compound melting at 162–164° C. were prepared from 37.6 g of 4-(4-fluorobenzyl)aniline.

Nuclear Magnetic Resonance Spectrum (hexadeuterated dimethyl sulfoxide) δ ppm:
3.31 (2H, singlet);
7.04–7.48 (7H, multiplet).

PREPARATION 22

2-Amino-5-(4-fluorobenzyl)benzenethiol

Following a procedure similar to that described in preparation 18, 31.3 9 of the title compound were prepared as a yellow syrup from 33.4 g of 2-amino-5(2-phenyl)methylbenzenethiol (prepared as described in preparation 21). This product was used in the following reaction without further purification.

PREPARATION 23

2-Amino-6-(5-methyl-2-thienyl)methylbenzothiazole

Following a procedure similar to that described in Preparation 17, 41.8 g of the title compound, melting at 179–181° C., were prepared from 45.1 g 4-(5-methyl-2-thienyl)methylaniline.

Nuclear Magnetic Resonance Spectrum (hexadeuterated dimethyl sulfoxide) δ ppm:
2.36 (3H, singlet);
4.05 (2H, singlet);
7.0–7.5 (5H, multiplet).

PREPARATION 24

2-Amino-5-(5-methyl-2-thienyl)methylbenzenethiol

Following a procedure similar to that described in Preparation 18, 38.4 g of the title compound were prepared as a yellow syrup from 41.3 g of 2-amino-6-(5-methyl-2-thienyl)methylbenzothiazole (prepared as described in Preparation 23). This product was used in the following reaction without further purification.

BIOLOGICAL ACTIVITY

The calcium channel blocking activity and antihypertensive activity of the compounds of the present invention were evaluated as follows:

(1) Calcium channel blocking action

The taenia coli excised from a male guinea pig weighing from 250 to 300 g was cut into a length of 6 to 7 mm and suspended in an organ bath filled with Tylord's solution (sodium chloride 97 mM, potassium chloride 40 mM, sodium hydrogen carbonate 11.9 mM, disodium hydrogen phosphate 0.4 mM, glucose 5.5 mM; pH 7.1). The bath solution contained no calcium ions and was aerated with a mixture of 95% oxygen and 5% carbon dioxide by volume. To this solution were added 10 and 30 mM solutions of calcium chloride at 30 minute intervals to obtain a final concentration of 0.4 mM. The tension which developed 1n the taenia coli was measured by an isometric transducer. The organ bath was then washed twice or more with Tylord's solution containing no calcium ions after which it was allowed to equilibrate for 30 minutes. After the muscle had stabilised, test compound dissolved in physiological saline was added to the bath to a final concentration of $10^{-8}$ g/ml, and the bath was incubated for 30 minutes. 30 and 100 mM solutions of calcium chloride were again added to the bath, and the developed tension was measured. From the magnitude of the calcium-induced contraction before and after the test drug had been added the inhibitory rate was calculated using the following formula:

$$\text{Percent inhibition of contraction} = \frac{(Co - Ct)}{Co} \times 100$$

where:
Co = contraction induced by calcium ion before a test drug was added: and
Ct = contraction induced by calcium ion after the test drug had been added.

In addition to the compounds of the invention, we also carried out the same test with the following compounds of the prior art: (±)-diltiazem, (±)-diltiazem, (±)-8-chlorodiltiazem (8-Cl-diltiazem). (±)-8-methoxydiltiazem (8-MeO-diltiazem) and (±)-8-benzyloxydiltiazem (8-BzO-diltiazem).

The results are shown in Table 5. In the Table, the compounds of the invention are identified by the number of the one of the foregoing Examples in which the compound was prepared. The prior art compounds are identified by the abbreviated generic names shown above in parentheses.

TABLE 5

| Compound of Example | Contraction inhibition (%) |
| --- | --- |
| 2 | 58 |
| 4 | 84 |

TABLE 5-continued

| Compound of Example | Contraction inhibition (%) |
|---|---|
| 6 | 53 |
| 12 | 86 |
| 14 | 94 |
| 16 | 80 |
| 18 | 77 |
| 20 | 57 |
| 22 | 52 |
| 24 | 93 |
| 28 | 59 |
| 30 | 56 |
| 32 | 100 |
| 34 | 88 |
| 36 | 80 |
| 38 | 69 |
| (+)-diltiazem | 20 |
| (±)-diltiazem | 11 |
| (±)-8-Cl-diltiazem | 56 |
| (±)-8-MeO-diltiazem | 67 |
| (±)-8-BzO-diltiazem | 55 |

All of the compounds except for that of Example 34 were employed as the hydrochlorides; that of Example 34 was employed as the fumarate.

(2) Antiypertensive action in SHR

Male SHR (spontaneously hypertensive rats), 23 to 30 weeks old, were anesthesized with sodium pentobarbital 50 mg/kg intraperitoneal administration), and a polyethylene cannula was inserted through the left femoral artery into the abdominal aorta. The other end of the cannula was led out of the body and fixed at the back of the neck. One week after the operation, when the animal had recovered from the stress of the surgery, the other end of the cannula was connected to a blood pressure measuring device, which was constructed according to the directions of Laffan et al. [Laffan, P.J., Peterson A., Hitch S,W. and Jeunelot C., Cardiovascular Res. 6. 319-324 (1972)], but with slight modifications. The blood pressure and heart rate of the conscious and unstained SHR were measured. After the blood pressure and the heart rate had stabilised for more than one hour, the test drug was administered by savage. The test drug was dissolved in a 50g agueous dimethyl sulfoxide solution and administered at the dose shown in Table 6. After administration of the test sample, the blood pressure and the heart rate were measured every 15 minutes over a period of 24 hours. The maximum decrease in blood pressure and the half-time of the blood pressure lowering activity thus determined are shown in Table 6.

All of the test compounds were employed as the hydrochlorides.

TABLE 6

| Compound of Example | Dose (mg/kg) | Maximum hypotension (%) | Half-time of hypotension action (hours) |
|---|---|---|---|
| 2 | 30 | −34 | 13.9 |
| 4 | 30 | −36 | 16.0 |
| 12 | 5 | −38 | 11.8 |
| 14 | 10 | −37 | 12.7 |
| 16 | 3 | −21 | 9.4 |
| 18 | 10 | −32 | 13.8 |
| 20 | 10 | −24 | 8.5 |
| 32 | 10 | −41 | 13.8 |
| 36 | 10 | −29 | 8.2 |
| 38 | 10 | −32 | 11.8 |
| (+)-diltiazem | 10 | −15 | 3.3 |
| (±)-diltiazem | 30 | −17 | 3.8 |
| (±)-8-Cl-diltiazem | 30 | −32 | 6.1 |

TABLE 6-continued

| Compound of Example | Dose (mg/kg) | Maximum hypotension (%) | Half-time of hypotension action (hours) |
|---|---|---|---|
| (±)-8-MeO-diltiazem | 30 | −35 | 5.8 |
| (±)-8-BzO-diltiazem | 30 | −19 | 7.7 |

We claim:

1. A compound of formula (I):

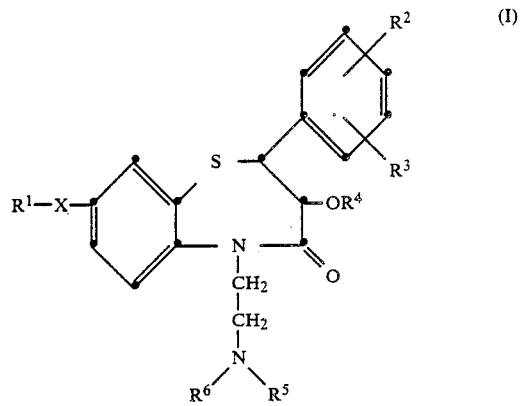

in which:

R$^1$ represents a C$_6$-C$_{10}$ carbocyclic aryl group, a substituted C$_6$-C$_{10}$ carbocyclic aryl group having at least one substituent selected from the group consisting of substituents (a), defined below an aromatic heterocyclic group selected from the group consisting of thienyl, furyl, benzofuranyl, isobenzofuranyl, pyrrolyl, pyrazolyl, oxazolyl, thiazolyl, isothiazolyl, isoxazolyl, triazolyl, imidazolyl, thiadiazolyl, pyridyl, pyrazinyl, pyrimidyl, pyridazinyl, indolyl, isoindolyl, quinolyl, isoquinolyl, phthalazinyl, quinoxalinyl and cinnolinyl groups, said heterocylic group being unsubstituted or having at least one substituent selected from the group consisting of substituents (a), defined below, or said unsubstituted heterocyclic group or substituted heterocyclic group fused to a benzene ring;

substituents (a):

C$_1$-C$_6$ alkyl groups, C$_1$-C$_6$ alkoxy groups, halogen atoms, phenyl groups, phenoxy groups, C$_1$-C$_6$ alkylthio groups, phenylthio groups, C$_1$-C$_6$ haloalkyl groups, hydroxy groups, cyano groups, nitro groups and aliphatic chains containing from 1 to 3 carbon atoms and 0, 1 or 2 oxygen atoms;

R$^2$ and R$^3$ are independently selected from the group consisting of hydrogen atoms, C$_1$-C$_6$ alkyl groups, C$_1$-C$_6$ alkoxy groups, halogen atoms, phenyl groups, phenoxy groups, C$_1$-C$_6$ alkylthio groups, phenylthio groups, C$_1$-C$_6$ haloalkyl groups, cyano groups and nitro groups, or R$^2$ and R$^3$ together represent an aliphatic chain containing from 1 to 3 carbon atoms and 0, 1 or 2 oxygen atoms;

R$^4$ represents a hydrogen atom, a C$_1$-C$_6$ aliphatic carboxylic acyl groups, a (C$_3$-C$_6$ cycloalkyl)-carbonyl group, a (C$_3$-C$_6$ cycloalkoxy)carbonyl group, aC$_7$-C$_{11}$ carbocyclic aromatic carboxylic acyl group, a C$_7$-C$_{11}$ carbocyclic aromatic carboxylic acyl group having at least one substituent selected from the group consisting of C$_1$-C$_6$ alkyl groups, C$_1$-C$_6$ alkoxy groups and halogen atoms, a $C_2-C_7$ alkoxycarbonyl group and a benzyloxycarbonyl group;

$R^5$ and $R^6$ are independently selected from the group consisting of $C_1-C_6$ alkyl groups; and X represents an oxygen atom, a sulfur atom or a methylene ($-CH_2-$) group;

and pharmaceutically acceptable salts thereof.

2. The compound of claim 1, wherein:

$R^1$ represents a phenyl group, a substituted phenyl group having at least one substituent selected from the group consisting of substituent ($a^1$), defined below, an aromatic heterocyclic group selected from the group consisting of thienyl, furyl, benzofuranyl, isobenzofuranyl, pyrrolyl, pyrazolyl, oxazolyl, thiazolyl, isothiazolyl, isoxazolyl, triazolyl, imidazolyl, thiadiazolyl, pyridyl, pyraxinyl, pyrimidyl, pyridazinyl, indolyl, isoindolyl, quinolyl, isoquinolyl, phthalazinyl, quinoxalinyl and cinnolinyl groups, said heterocylic group being unsubstituted or and having at least one substituent selected from the group consisting of substituents ($a^2$);

substituents ($a^1$):

$C_1-C_4$ alkyl groups, $C_1-C_4$ alkoxy groups and halogen atoms;

substituents ($a^2$):

$C_1-C_4$ alkyl groups and halogen atoms.

3. The compound of claim 1, wherein $R^2$ and $R^3$ are independently selected from the group consisting of hydrogen atoms, $C_1-C_4$ alkyl groups, $C_1-C_4$ alkoxy groups and halogen atoms, or $R^2$ and $R^3$ together represent an aliphatic chain containing from 1 to 3 carbon atoms and 1 or 2 oxygen atoms.

4. The compound of claim 1, wherein $R^4$ represents a hydrogen atom, a $C_2-C_6$ aliphatic carboxylic acyl group, a ($C_3-C_6$ cycloalkyl)carbonyl group, a ($C_3-C_6$ cycloalkoxy)carbonyl group, a $C_7-C_{11}$ arylcarbonyl group, a substituted $C_7-C_{11}$ arylcarbonyl group having at least one $C_1-C_4$ alkyl substituent, or a $C_2-C_5$ alkoxycarbonyl group.

5. The compound of claim 1, wherein $R^5$ and $R^6$ are independently selected from the group consisting of $C_1-C_4$ alkyl groups.

6. The compound of claim 1, wherein: $R^1$ represents a phenyl group, a substituted phenyl group having at least one substituent selected from the group consisting of substituents ($a^1$), defined below, an aromatic heterocyclic group selected from the group consisting of thienyl, furyl, benzofuranyl, isobenzofuranyl, pyrrolyl, pyrazolyl, oxazolyl, thiazolyl, isothiazolyl, isoxazolyl, triazolyl, imidazolyl, thiadiazolyl, pyridyl, pyrazinyl, pyrimidyl, pyridazinyl, indolyl, isoindolyl, quinolyl, isoquinolyl, phthalazinyl, quinoxalinyl and cinnolinyl groups, said heterocylic group being unsubstituted or having at least one substituent selected from the group consisting of substituents ($a^2$);

substituents ($a^1$):

$C_1-C_4$ alkyl group, $C_1-C_4$ alkoxy groups and halogen atoms;

substituents ($a^2$):

$C_1-C_4$ alkyl groups and halogen atoms;

$R^2$ and $R^3$ are independently selected from the group consisting of hydrogen atoms, $C_1-C_4$ alkyl groups, $C_1-C_4$ alkoxy group and halogen atoms, or $R^2$ and $R^3$ together represent an aliphatic chain containing from 1 to 3 carbon atoms and 1 or 2 oxygen atoms;

$R^4$ represents a hydrogen atom, a $C_2-C_6$ aliphatic carboxylic acyl group, a ($C_3-C_6$ cycloalkyl)-carbonyl group, a ($C_3-C_6$ cycloalkoxy)carbonyl group, a $C_7-C_{11}$ arylcarbonyl group, a substituted $C_7-C_{11}$ arylcarbonyl group having at least one $C_1-C_4$ alkyl substituent, or a $C_2-C_5$ alkoxycarbonyl group;

$R^5$ and $R^6$ are independently selected from the group consisting of $C_1-C_4$ alkyl groups; and X represents an oxygen atom, a sulfur atom or a methylene group.

7. The compound of claim 1, wherein:

$R^1$ represents:

a phenyl group, a substituted phenyl group having at least one substituent selected from the group consisting of substituents ($a^1$), defined below, or an aromatic heterocyclic group selected from the group consisting of thienyl, furyl, isoxazolyl, oxazolyl, thiazolyl and thiadiazolyl groups, said heterocyclic group being unsubstituted or havving at least one $C_1-C_4$ alkyl substituents;

substituents ($a^1$):

$C_1-C_4$ alkyl groups, $C_1-C_4$ alkoxy groups and halogen atoms;

$R^2$ and $R^3$ are independently selected from the group consisting of hydrogen atoms, $C_1-C_4$ alkyl groups. $C_1-C_4$ alkoxy groups and halogen atoms, or $R^2$ and $R^3$ together represent an aliphatic chain containing from 1 to 3 carbon atoms and 1 or 2 oxygen atoms;

$R^4$ represents a hydrogen atom, a $C_2-C_6$ aliphatic carboxylic acyl group, a ($C_3-C_6$ cycloalkyl)carbonyl group, a ($C_3-C_6$ cycloalkoxy)carbonyl group, a benzoyl group, a substituted benzoyl group having at least one $C_1-C_4$ alkyl substituent, or a $C_2-C_5$ alkoxycarbonyl group;

$R^5$ and $R^6$ are independently selected from the group consisting of $C_1-C_4$ alkyl groups; and X represents an oxygen atom, a sulfur atom or a methylene group.

8. The compound of claim 1, wherein;

$R^1$ represents:

a phenyl group, a substituted phenyl group having at least one substituent selected from the group consisting of substituents ($a^3$), defined below, or an aromatic heterocyclic group selected from the group consisting of thienyl, turyl, oxazolyl, thiazolyl and thiadiazolyl groups, said heterocyclic group being unsubstituted or having at least one methyl substituent;

substituents ($a^3$):

methyl groups, methoxy groups, fluoro atoms and chloro atoms;

$R^2$ and $R^3$ are independently selected from the group consisting of hydrogen atoms, methyl groups, methoxy groups, ethoxy groups, fluorine atoms and chlorine atoms, or $R^2$ and $R^3$ together represent an group of formula $-O-CH_2-O-$;

$R^4$ represents a hydrogen atom, an acetyl group, a propionyl group a cyclopropanecarbonyl group, a cyclopropoxycarbonyl group, a benzoyl group, a toluoyl group, a methoxycarbonyl group or an ethoxycarbonyl group;

$R^5$ and $R^6$ are independently selected from the consisting of methyl and ethyl groups; and X represents an oxygen atom or a methylene group.

9. The compound of claim 1 selected from the group consisting of 5-(2-dimethylaminoethyl)-2,3-dihydro-3-hydroxy-2-(4-methoxyphenyl)-8-phenoxy-1,5-benzothiazepin-4(5H)-one and pharmaceutically acceptable salts thereof.

10. The compound of claim 1 selected from the group consisting of 3-acetoxy-5-(2-dimethylaminoethyl)-2,3-dihydro-2-(4-methoxyphenyl)-8-phenoxy-1,5-benzothiazepin- 4(5H)-one and pharmaceutically acceptable salts thereof.

11. The compound of claim 1, selected from the group consisting of 5-(2-dimethylaminoethyl)-2-(3-fluoro-4- methoxyphenyl)-2,3-dihydro-3-hydroxy-8-phenoxy-1,5-benzo- thiazepin-4(5H1-one and pharmaceutically acceptable salts thereof.

12. The compound of claim 1 selected from the group consisting of 3-acetoxy-5-(2-dimethylaminoethyl)-2-(3-fluoro-4-methoxyphenyl)-2,3-dihydro-8-phenoxy-1,5-benzo- thiazepin-4(5H)-one and pharmaceutically acceptable salts thereof.

13. The compound of claim 1, selected from the group consisting of 5-(2-dimethylaminoethyl)-2,3-dihydro-3- hydroxy-2-(3,4-methylenedioxyphenyl)-8-phenoxy-1,5-benzo- thiazepin-4(5H)-one and pharmaceutically acceptable salts thereof.

14. The compound of claim 1 selected from the group consisting of 3-acetoxy-5-(2-dimethylaminoethyl)-2,3-dihydro-2-(3,4-methylenedioxyphenyl)-8-phenoxy-1,5-benzothiazepin-(5H)-one and pharmaceutically acceptable thereof.

15. The compound of claim 1, selected from the group consisting of 3-acetoxy-5-(2-dimethylaminoethyl)-8-(4- fluorophenoxy)-2,3-dihydro-2-(4-methoxyphenyl)-1,5-benzo- thiazepin-4(5H)-one and pharmaceutically acceptable salts thereof.

16. The compound of claim 1, selected from the group consisting of 5-(2-dimethylaminoethyl)-B-(4- fluoro- phenoxy)-2,3-dihydro-3-hydroxy-2-(4-methoxyphenyl)-1,5- benzothiazepin-4(5H)-one and pharmaceutically acceptable salts thereof.

17. The compound of claim 1, selected from the group consisting of 5-(2-dimethylaminoethyl)-2-(3-fluoro-4- methoxyphenyl)-8-(4-fluorophenoxy)-2,3-dihydro-3-hydroxy- 1,5-benzothiazepin-4(5H)-one and pharmaceutically acceptable salts thereof.

18. The compound of claim 1 selected from the group consisting of 3-acetoxy-5-(2-dimethylaminoethyl)-2-(3-fluoro-4-methoxyphenyl)-8-(4-fluorophenoxy)-2,3-dihydro- 1,5-benzothiazepin-4(5H)-one and pharmaceutically acceptable salts thereof.

19. The compound of claim 1 selected from the group consisting of 8-benzyl-5-(2-dimethylaminoethyl)-2,3-dihydro-3-hydroxy-2-(4-methoxyphenyl)-1,5-benzothiazepin- 4(5H)-one and pharmaceutically acceptable salts thereof.

20. The compound of claim 1 selected from the group consisting of 3-acetoxy-8-benzyl-5-(2-dimethylaminoethyl)-2,3-dihydro-2-(4-methoxyphenyl)-1,5-benzothiazepin-4(5H)-one and pharmaceutically acceptable salts thereof.

21. The compound of claim 1, selected from the group consisting of 8-benzyl-5-(2-dimethylaminoethyl)-2-(3- fluoro-4-methoxyphenyl)-2,3-dihydro-3-hydroxy-1 -benzo- thiazepin-4(5H)-one and pharmaceutically acceptable salts thereof.

22. The compound of claim 1, selected from the group consisting of 3-acetoxy-8-benzyl-5-(2-dimethylamino- ethyl)-2-(3-fluoro-4-methoxyphenyl)-2,3-dihydro-1,5- benzothiazepin-4(5H)-one and pharmaceutically acceptable salts thereof.

23. The compound of claim 1, selected from the group consisting of 3-acetoxy-5-(2-dimethylaminoethyl)-8-(4- fluorobenzyl)-2-(4-methoxyphenyl)-2,3-dihydro-1,5- benzothiazepin-4(5H)-one and pharmaceutically acceptable salts thereof.

24. The compound of claim 1, selected from the group consisting of 5-(2-dimethylaminoethyl)-8-(4-fluoro- benzyl)-2 3-dihydro-3-hydroxy-2-(4-methoxyphenyl)-1,5- benzothiazepin-4(5H)-one and pharmaceutically acceptable salts thereof.

25. The compound of claim 1, selected from the group consisting of 5-(2-dimethylaminoethyl)-2,3-dihydro-3- hydroxy-2-(4-methoxyphenyl)-8-(2-thienylmethyl)-1,5- benzothiazepin-4(5H)-one and pharmaceutically acceptable salts thereof.

26. The compound of claim 1 selected from the group consisting of 3-acetoxy-5-(2-dimethylaminoethyl)-2,3-dihydro-2-(4-methoxyphenyl)-8-(2-thienylmethyl)-1,5-benzothiazepin-4(5H)-one and pharmaceutically acceptable salts thereof.

27. The compound of claim 1, selected from the group consisting of 5-(2-dimethylaminoethyl)-8-(2-furyl- methyl)-2,3-dihydro-3-hydroxy-2-(4-methoxyphenyl)-1,5- benzothiazepin-4(5H)-one and pharmaceutically acceptable salts thereof.

28. The compound of claim 1 selected from the group consisting of 3-acetoxy-5-(2-dimethylaminoethyl)-8-(2-furylmethyl)-2,3-dihydro-2-(4-methoxyphenyl)-1,5-benzo- thiazepin-4(5H)-one and pharmaceutically acceptable salts thereof.

29. A pharmaceutical composition for the treatment or prophylaxis of cardiovascular diseases and disorders, which comprises an effective amount of a calcium channel blocker in admixture with a pharmaceutically acceptable carrier or diluent, wherein the calcium channel blocker is at least one compound selected from the group consisting of compounds of formula (I) and pharmaceutically acceptable salts thereof, as claimed in claim 1.

30. The composition of claim 29, wherein:
$R^1$ represents:
   a phenyl group,
   a substituted phenyl group having at least one substituent selected from the group consisting of substituents ($a^1$), defined below, or
   an aromatic heterocyclic group selected from the group consisting of thienyl, furyl, isoxazolyl, oxazolyl thiazolyl and thiadiazolyl groups, said heterocyclic group being unsubstituted or having at least one $C_1$–$C_4$ alkyl substituent;
substituents ($a^1$):
   $C_1$–$C_4$ alkyl groups, $C_1$–$C_4$ alkoxy groups and halogen atoms;
$R^2$ and $R^3$ are independently selected from the group consisting of hydrogen atoms, $C_1$–$C_4$ alkyl groups, $C_1$–$C_4$ alkoxy groups and halogen atoms, or $R^2$ and $R^3$ together represent an aliphatic chain containing from 1 to 3 carbon atoms and 1 or 2 oxygen atoms;
$R^4$ represents a hydrogen atom, a $C_2$–$C_6$ aliphatic carboxylic acyl group, a ($C_3$–$C_6$ cycloalkyl)carbonyl group, a ($C_3$–$C_6$ cycloalkoxy)carbonyl group, a benzoyl group, a substituted benzoyl group having at least one $C_1$–$C_4$ alkyl substituent, or a $C_2$–$C_5$ alkoxycarbonyl group;
$R^5$ and $R^6$ independently selected from the group consisting of $C_1$–$C_4$ alkyl groups; and
X represents an oxygen atom, a sulfur atom or a methylene group.

31. The composition of claim 29, wherein:
R¹ represents:
a phenyl group,
a substituted phenyl group having at least one substituent selected from the group consisting of substituents (a³), defined below, or
an aromatic heterocyclic group selected from the group consisting of thienyl, furyl, oxazolyl, thiazolyl and thiadiazolyl 9groups, said heterocyclic group being unsubstituted or having at least one methyl substituent;
substituents (a³):
methyl groups, methoxy groups, fluoro atoms and chloro atoms:
R² and R³ are independently selected from the group consisting of hydrogen atoms, methyl groups, methoxy groups, ethoxy groups, fluorine atoms and chlorine atoms, or R² and R³ together represent an group of formula —O—CH₂—O—;
R⁴ represents a hydrogen atom, an acetyl group, a propionyl group, a cyclopropanecarbonyl group, a cyclopropoxycarbonyl group, a benzoyl group, a toluoyl group, a methoxycarbonyl group or an ethoxycarbonyl group;
R⁵ and R⁶ are independently selected from the group consisting of methyl and ethyl groups; and
X represents an oxygen atom or a methylene group.

32. The composition of claim 29, wherein said calcium channel blocker is selected from the group consisting of:
5-(2-dimethylaminoethyl)-2,3-dihydro-3-hydroxy- 2-(4-methoxyphenyl)-8-phenoxy-1,5-benzothiazepin-4(5H)-one:
3-acetoxy-5-(2-dimethylaminoethyl)-2 3-dihydro- 2-(4-methoxyphenyl)-8-phenoxy-1,5-benzothiazepin-4(5H)one;
5-(2-dimethylaminoethyl)-2-(3-fluoro-4-methoxy- phenyl)-2,3-dihydro-3-hydroxy-8-phenoxy-1,5-benzothiazepin-4(5H)-one;
3-acetoxy-5-(2-dimethylaminoethyl)-2-(3-fluoro- 4-methoxyphenyl)-2,3-dihydro-8-phenoxy-1,5-benzothiazepin-4(5H)-one;
5-(2-dimethylaminoethyl)-2,3-dihydro-3-hydroxy- 2-(3,4-methylenedioxyphenyl)-8-phenoxy-1,5-benzothiazepin-4(5H)-one;
3-acetoxy—(2-dimethylaminoethyl)-2,3-dihydro- 2-(3,4-methylenedioxyphenyl)-8-phenoxy-1,5-benzothiazepin-(5H)-one;
3-acetoxy-5-(2-dimethylaminoethyl)-8-(4-fluoro- phenoxy)-2,3-dihydro-2-(4-methoxyphenyl)-1,5-benzothiazepin-4(5H)-one:
5-(2-dimethylaminoethyl)--(4-fluorophenoxy)- 2,3-dihydro-3-hydroxy-2-(4-methoxyphenyl)-1,5-benzothiazepin-4(5H)-one; 5-(2-dimethylaminoethyl)-2-(3-fluoro-4-methoxy- phenyl)-8-(4-fluorophenoxy)-2,3-dihydro-3-hydroxy-1,5-benzothiazepin-4(5H)-one;
3-acetoxy-5-(2-dimethylaminoethyl)-2-(3-fluoro- 4-methoxyphenyl)-8-(4-fluorophenoxy)-2,3-dihydro-1,5-benzothiazepin-4(5H)-one:
8-benzyl-5-(2-dimethylaminoethyl)-2,3-dihydro-3- hydroxy-2-(4-methoxyphenyl)-1,5-benzothiazepin-4(5H)-one;
3-acetoxy-8-benzyl-5-(2-dimethylaminoethyl)-2,3- dihydro-2-(4-methoxyphenyl)-1,5-benzothiazepin-4(5H)-one;
8-benzyl-5-(2-dimethylaminoethyl)-2-(3-fluoro- 4-methoxyphenyl)-2,3-dihydro-3-hydroxy-1,5-benzothiazepin-4(5H)-one;
3-acetoxy-8-benzyl-5-(2-dimethylaminoethyl)-2-(3-fluoro-4-methoxyphenyl)-2 3-dihydro-1 5-benzothiazepin-4(5H)-one:
3-acetoxy-5-(2-dimethylaminoethyl)-8-(4-fluorobenzyl)- 2,3-dihydro-2-(4-methoxyphenyl)-1 5-benzothiazepin-4(5H)-one;
5-(2-dimethylaminoethyl)-8-(4-fluorobenzyl)-2,3-dihydro- 3-hydroxy-2-(4-methoxyphenyl)-1,5-benzothiazepin-4(5H)-one;
5-(2-dimethylaminoethyl)-2,3-dihydro-3-hydroxy- 2-(4-methoxyphenyl)-8-(2-thienylmethyl)-1,5-benzothiazepin-4(5H)-one;
3-acetoxy-5-(2-dimethylaminoethyl)-2,3-dihydro- 2-(4-methoxyphenyl)-8-(2-thienylmethyl)-1,5-benzothiazepin-4(5H)-one;
5-(2-dimethylaminoethyl)-8-(2-furylmethyl)-2,3-dihydro-3-hydroxy-2-(4-methoxyphenyl)-1,5-benzothiazepin-4(5H)one;
3-acetoxy-5-(2-dimethylaminoethyl)-8-(2-furyl- methyl)-2,3-dihydro-2-(4-methoxyphenyl)-1,5-benzothiazepin-4(5H)-one;
and pharmaceutically acceptable salts thereof.

33. A method for the treatment or prophylaxis of cardiovascular diseases and disorders, which comprises administering to a susceptible animal an effective amount of a calcium channel blocker, Wherein the calcium channel blocker is at least one compound selected from the group consisting of compounds of formula (I) and pharmaceutically acceptable salts thereof, as claimed in claim 1.

34. The method of claim 33, wherein:
R¹ represents:
a phenyl group,
a substituted phenyl group having at least one substituent selected from the group consisting of substituents (a¹), defined below or
an aromatic heterocyclic group selected from the group consisting of thienyl furyl isoxazolyl. oxazolyl, thiazolyl and thiadiazolyl groups said heterocyclic group being unsubstituted or having at least one $C_1$–$C_4$ alkyl substituent;
substituents (¹a ):
$C_1$–$C_4$ alkyl groups $C_1$–$C_4$ alkoxy groups and halogen atoms:
R² and R³ are independently selected from the group consisting of hydrogen atoms, $C_1$–$C_4$ alkyl groups. $C_1$–$C_4$ alkoxy groups and halogen atoms, or R² and R³ together represent an aliphatic chain containing from 1 to 3 carbon atoms and 1 or 2 oxygen atoms;
R⁴ represents a hydrogen atom, a $C_2$–$C_6$ aliphatic carboxylic acyl group a ($C_3$–$C_6$ cycloalkyl)carbonyl group, a ($C_3$–$C_6$ cycloalkoxy)carbonyl group, a benzoyl group, a substituted benzoyl group having at least one $C_1$–$C_4$ alkyl substituent, or a $C_2$–$C_5$ alkoxycarbonyl group;
R⁵ and R⁶ are independently selected from the group consisting of $C_1$–$C_4$ alkyl groups; and
X represents an oxygen atom, a sulfur atom or a methylene group.

35. The method of claim 33, wherein:
R¹ represents:
a phenyl group,
a substituted phenyl group having at least one substituent selected from the group consisting of substituents (a³), defined below, or
an aromatic heterocyclic group selected from the group consisting of thienyl, furyl, oxazolyl. thiazolyl and thiadiazolyl groups, said heterocyclic group being unsubstituted or having at least one methyl substituent;

substituents (a³):
  methyl groups, methoxy groups, fluoro atoms and chloro atoms;

$R^2$ and $R^3$ are independently selected from the group consisting of hydrogen atoms, methyl groups, methoxy groups, ethoxy groups fluorine atoms and chlorine atoms, or $R^2$ and $R^3$ together represent an group of formula —O—CH$_2$—O—;

$R^4$ represents a hydrogen atom, an acetyl group, a propionyl group, a cyclopropanecarbonyl group, a cyclopropoxycarbonyl group, a benzoyl group, a toluoyl group, a methoxycarbonyl group or an ethoxycarbonyl group;

$R^5$ and $R^6$ are independently selected from the group consisting of methyl and ethyl groups; and X represents an oxygen atom or a methylene group.

36. The method of claim 33, wherein said calcium channel blocker is selected from the group consisting of:

5-(2-dimethylaminoethyl)-2,3-dihydro-3-hydroxy- 2-(4-methoxyphenyl)-8-phenoxy-1,5-benzothiazepin-4(5H)-one;

3-acetoxy-5-(2-dimethylaminoethyl)-2,3-dihydro- 2-(4-methoxyphenyl)-8-phenoxy-1,5-benzothiazepin-4(5H)-one;

5-(2-dimethylaminoethyl)-2-(3-fluoro-4-methoxy- phenyl)-2,3-dihydro-3-hydroxy-8-phenoxy-1,5-benzothiazepin-4(5H)-one:

3-acetoxy-5-(2-dimethylaminoethyl)-2-(3-fluoro- 4-methoxyphenyl)-2,3-dihydro-8-phenoxy-1,5-benzothiazepin-4(5H)-one:

5-(2-dimethylaminoethyl)-2,3-dihydro-3-hydroxy- 2-(3,4-methylenedioxyphenyl)-8-phenoxy-1,5-benzothiazepin-4(5H)-one;

3-acetoxy-5-(2-dimethylaminoethyl)-2,3-dihydro- 2-(3,4-methylenedioxyphenyl)-8-phenoxy-1,5-benzothiazepin-(5H)-one:

3-acetoxy-5-(2-dimethylaminoethyl)-8-(4-fluoro- phenoxy)-2,3-dihydro-2-(4-methoxyphenyl)-1,5-benzothiazepin-4(5H)-one:

5-(2-dimethylaminoethyl)-8-(4-fluorophenoxy)- 2,3-dihydro-3-hydroxy-2-(4-methoxyphenyl)-1,5-benzothiazepin-4(5H)-one;

5-(2-dimethylaminoethyl)-2-(3-fluoro-4-methoxy- phenyl)-8-(4-fluorophenoxy)-2,3-dihydro-3-hydroxy-1,5-benzothiazepin-4(5H)-one;

3-acetoxy-5-(2-dimethylaminoethyl)-2-(3-fluoro- 4-methoxyphenyl)-8-(4-fluorophenoxy)-2,3-dihydro-1,5-benzothiazepin-4(5H)-one;

8-benzyl-5-(2-dimethylaminoethyl)-2,3-dihydro-3- hydroxy-2-(4-methoxyphenyl)-1,5-benzothiazepin-4(5H)-one;

3-acetoxy-8-benzyl-b-(2-dimethylaminoethyl)-2,3- dihydro-2-(4-methoxyphenyl)-1,5-benzothiazepin-4(5H)-one:

8-benzyl-5-(2-dimethylaminoethyl)-2-(3-fluoro- 4-methoxyphenyl)-2,3-dihydro-3-hydroxy-1,5-benzothiazepin-4(5H)-one;

3-acetoxy-8-benzyl-5-(2-dimethylaminoethyl)-2-(3- fluoro-4-methoxyphenyl)-2,3-dihydro-1,5-benzothiazepin-4(5H)-one 3-acetoxy-5-(2-dimethylaminoethyl)-8-(4-fluoroben- zyl)- 2,3-dihydro-2-(4-methoxyphenyl)-1,5-benzothiazepin-4(5H)-one:

5-(2-dimethylaminoethyl)-8-(4-fluorobenzyl)-2,3-dihy- dro- 3-hydroxy-2-(4-methoxyphenyl)-1,5-benzothiazepin-4(5H)-one:

5-(2-dimethylaminoethyl)-2,3-dihydro-3-hydroxy- 2-(4-methoxyphenyl)-8-(2-thienylmethyl)-1,5-benzothiazepin-4(5H)-one;

3-acetoxy-5-(2-dimethylaminoethyl)-2,3-dihydro- 2-(4-methoxyphenyl)-8-(2-thienylmethyl)-1,5-benzothiazepin-4(5H)-one;

5-(2-dimethylaminoethyl)-8-(2-furylmethyl)-2,3-dihy- dro- 3-hydroxy-2-(4-methoxyphenyl)-1,5-benzothiazepin-4(5H)-one;

3-acetoxy-5-(2-dimethylaminoethyl)-8-(2-furyl- methyl)2,3-dihydro-2-(4-methoxyphenyl)-1,5-benzothiazepin-4(5H)-one:

and pharmaceutically acceptable salts thereof.

37. The compound of claim 1, wherein $R^1$ represents a phenyl group.

38. The compound of claim 1, wherein $R^1$ represents a phenyl, 4-thiazolyl, 2-furyl, 2-thienyl, 4-oxazolyl or 1,3,4-thiadiazol-2-yl group.

39. The composition of claim 29, wherein $R^1$ represents a phenyl group.

40. The composition of claim 29, wherein $R^1$ represents a phenyl, 4-thiazolyl, 2-furyl, 2-thienyl, 4-oxazolyl or 1,3,4-thiadiazol-2-yl group.

41. The method of claim 33, wherein $R^1$ represents a phenyl group.

42. The method of claim 33, wherein $R^1$ represents a phenyl, 4-thiazolyl, 2-furyl, 2-thienyl, 4-oxazolyl or 1,3,4-thiadiazol-2-yl group.

* * * * *